US012591974B2

(12) United States Patent
Divaraniya et al.

(10) Patent No.: US 12,591,974 B2
(45) Date of Patent: Mar. 31, 2026

(54) METHODS, DEVICES, AND SYSTEMS FOR DETECTING ANALYTE LEVELS

(71) Applicant: OOVA, INC., New York, NY (US)

(72) Inventors: Aparna Divaraniya, New York, NY (US); Jerome Scelza, New York, NY (US)

(73) Assignee: OOVA, INC., New York, NY (US)

( * ) Notice: Subject to any disclaimer, the term of this patent is extended or adjusted under 35 U.S.C. 154(b) by 334 days.

(21) Appl. No.: 17/255,028

(22) PCT Filed: Jun. 20, 2019

(86) PCT No.: PCT/US2019/038173
§ 371 (c)(1),
(2) Date: Dec. 22, 2020

(87) PCT Pub. No.: WO2019/246361
PCT Pub. Date: Dec. 26, 2019

(65) Prior Publication Data
US 2021/0264604 A1 Aug. 26, 2021

Related U.S. Application Data

(60) Provisional application No. 62/688,970, filed on Jun. 22, 2018.

(51) Int. Cl.
*G06T 7/00* (2017.01)
*G01N 21/78* (2006.01)
(Continued)

(52) U.S. Cl.
CPC ........... *G06T 7/0016* (2013.01); *G01N 21/78* (2013.01); *G01N 21/8483* (2013.01);
(Continued)

(58) Field of Classification Search
CPC ..................... G06T 7/0016; G06T 7/90; G06T 2207/20081; G01N 21/78; G01N 21/8483;
(Continued)

(56) References Cited

U.S. PATENT DOCUMENTS

2010/0183225 A1* 7/2010 Vantaram ................ G06T 7/168
382/173
2010/0312137 A1* 12/2010 Gilmour .............. G01N 33/689
600/551
(Continued)

FOREIGN PATENT DOCUMENTS

EP 2781910 A1 9/2014
GB 2569803 A 7/2019
(Continued)

OTHER PUBLICATIONS

Exam Report issued in Great Britain Patent Application No. GB2100420.5 on Feb. 4, 2022.
(Continued)

*Primary Examiner* — Chad A Newton
(74) *Attorney, Agent, or Firm* — Wilson Sonsini Goodrich & Rosati

(57) ABSTRACT

The present disclosure describes a method of quantifying analyte levels using gold nanoparticles. The present disclosure also describes a device to quantify analyte levels using gold nanoparticles and image processing of pixels isolated from a single vector. The methods, devices, and systems of the disclosure can be used to quantify analytes such as luteinizing hormone, progesterone, estradiol, or testosterone.

24 Claims, 77 Drawing Sheets

(51) Int. Cl.

| | | |
|---|---|---|
| *G01N 21/84* | (2006.01) | |
| *G01N 33/543* | (2006.01) | |
| *G01N 33/74* | (2006.01) | |
| *G01N 33/76* | (2006.01) | |
| *G06T 7/90* | (2017.01) | |
| *G16H 10/40* | (2018.01) | |
| *G16H 15/00* | (2018.01) | |
| *G16H 50/30* | (2018.01) | |

(52) U.S. Cl.
CPC ..... *G01N 33/54388* (2021.08); *G01N 33/743* (2013.01); *G01N 33/76* (2013.01); *G06T 7/90* (2017.01); *G16H 10/40* (2018.01); *G16H 15/00* (2018.01); *G16H 50/30* (2018.01); *G01N 2201/0221* (2013.01); *G01N 2800/36* (2013.01); *G06T 2207/20081* (2013.01)

(58) Field of Classification Search
CPC .......... G01N 33/54388; G01N 33/743; G01N 33/76; G01N 2201/0221; G01N 2800/36; G16H 10/40; G16H 15/00; G16H 50/30
See application file for complete search history.

(56) References Cited

U.S. PATENT DOCUMENTS

| | | | | |
|---|---|---|---|---|
| 2013/0130404 | A1* | 5/2013 | Mehra .............. | G01N 33/54393 |
| | | | | 422/69 |
| 2013/0273563 | A1 | 10/2013 | Ehrenkranz | |

| | | | | |
|---|---|---|---|---|
| 2014/0377770 | A1 | 12/2014 | Bischof et al. | |
| 2015/0065372 | A1 | 3/2015 | Amir et al. | |
| 2015/0094227 | A1 | 4/2015 | Mccarthy et al. | |
| 2015/0359458 | A1 | 12/2015 | Erickson et al. | |
| 2016/0080548 | A1 | 3/2016 | Erickson et al. | |
| 2017/0301108 | A1* | 10/2017 | Estrada ..................... | G06T 7/74 |
| 2017/0323441 | A1 | 11/2017 | Shah et al. | |
| 2018/0106804 | A1* | 4/2018 | Pulitzer ................ | G06T 7/0014 |
| 2018/0321251 | A1 | 11/2018 | Beckley | |
| 2018/0322941 | A1* | 11/2018 | Krishnan .............. | G16H 40/63 |
| 2018/0372717 | A1* | 12/2018 | Tu .................... | G01N 35/00732 |

FOREIGN PATENT DOCUMENTS

| | | |
|---|---|---|
| WO | WO-2017058827 A1 | 4/2017 |
| WO | WO-2019133920 A1 | 7/2019 |

OTHER PUBLICATIONS

PCT International Search Report and Written Opinion dated Sep. 13, 2019 for PCT/US19/38173.

Search Report issued in European Patent Application No. 19823616.8 on Jan. 25, 2022.

Second Exam Report issued in Great Britain Patent Application No. GB2100420.5 on May 31, 2022.

\* cited by examiner

Holder →

Handle →

Disposable Cartridge →

A

B

C

| | [LH] (mIU/mL) | Avg | Std Dev | %CV | Image |
|---|---|---|---|---|---|
| Blank (50mM Tris) | 0 | 121 | 29 | 24% | |
| ELISA Standards | 0 | 252 | 24 | 10% | |
| | 10 | 5890 | 188 | 3% | |
| | 20 | 8737 | 239 | 3% | |
| | 40 | 11666 | 366 | 3% | |
| | 100 | 14783 | 310 | 2% | |
| | 200 | 15725 | 186 | 1% | |

FIG. 41

| [PdG] spiked into U6 (µg/mL) | Axxin Peak Value | | Image |
| | Test Line | Control Line | |
|---|---|---|---|
| 0 | 11240 | 6410 | |
| | 11340 | 6010 | |
| 0.15625 | 9300 | 5670 | |
| | 10040 | 7500 | |
| 0.3125 | 8750 | 7600 | |
| | 8840 | 7880 | |
| 0.625 | 7580 | 8880 | |
| | 6140 | 7140 | |
| 1.25 | 6420 | 9550 | |
| | 6130 | 9470 | |
| 2.5 | 3540 | 9550 | |
| | 2870 | 8870 | |
| 5 | 1880 | 9420 | |
| | 1550 | 8000 | |

FIG. 44

| Strip Image | Sample | Value | | Strip Image | Sample | Value |
|---|---|---|---|---|---|---|
| | F1 | 4720 | | | F11 | 13100 |
| | | 3830 | | | | 12220 |
| | | 4100 | | | | 12400 |
| | | 3620 | | | | 11670 |
| | F2 | 6180 | | | F12 | |
| | | 6640 | | | | 10740 |
| | | 6590 | | | | 10910 |
| | | 6550 | | | | 11180 |
| | F3 | 3810 | | | F13 | |
| | | 4470 | | | | 5470 |
| | | 4220 | | | | 4520 |
| | | 3660 | | | | 5670 |
| | F4 | 6710 | | | F14 | 12210 |
| | | 6270 | | | | 12850 |
| | | 6210 | | | | 12690 |
| | | 6800 | | | | 12060 |
| | F5 | 6690 | | | F15 | 5420 |
| | | 6560 | | | | 4910 |
| | | 6630 | | | | 4810 |
| | | 7220 | | | | 4440 |
| | F6 | 980 | | | F16 | 4130 |
| | | 1110 | | | | 5120 |
| | | 1110 | | | | 4370 |
| | | 980 | | | | 4160 |
| | F7 | 1100 | | | F17 | 3590 |
| | | 890 | | | | 3460 |
| | | 750 | | | | 2660 |
| | | 880 | | | | 2810 |
| | F8 | 14100 | | | F18 | 9110 |
| | | 14100 | | | | 10590 |
| | | 13530 | | | | 8990 |
| | | 12540 | | | | 11490 |
| | F9 | 12140 | | | F19 | 8040 |
| | | 11980 | | | | 7390 |
| | | 11190 | | | | 8210 |
| | | 11850 | | | | 8040 |
| | F10 | 4640 | | | F20 | 4960 |
| | | 5620 | | | | 4430 |
| | | 5620 | | | | 3640 |
| | | 5050 | | | | |

FIG. 45

| LH Gold OD | LH TL conc (mg/mL) | Negative (0LH, 0PdG) | | Spiked (100LH, 1.25PdG) | |
|---|---|---|---|---|---|
| | | Image | Peak Value | Image | Peak Value |
| OD4 | 1 | | 600 | | 3440 |
| | 2 | | 790 | | 3940 |
| OD8 | 1 | | 730 | | 3860 |
| | 2 | | 950 | | 4590 |
| OD12 | 1 | | 870 | | 3920 |
| | 2 | | 930 | | 4970 |

FIG. 52

| LH conc (mIU/mL) | Previous conjugate 4/4 prep | | | New conjugate 4/4 prep | | |
|---|---|---|---|---|---|---|
| | Image | LH | Peak | Image | LH | Peak |
| 0 | | | 440 | | | 680 |
| 0 | | | 390 | | | 630 |
| 10 | | | 710 | | | 1060 |
| 10 | | | 700 | | | 1280 |
| 25 | | | 1230 | | | 1910 |
| 25 | | | 1320 | | | 1870 |
| 50 | | | 2360 | | | 3040 |
| 50 | | | 2420 | | | 2990 |

FIG. 53

| Note | Spotted Contents | | Urine Volume | Images | | Peak Value | (LH25)/(LH0) |
|---|---|---|---|---|---|---|---|
| | Conj | RB | | [LH] | Whole Strip | | |
| 15min read | Full | 8µL RB | 80µL | 0 | | 540 | 2.4 |
| | | | | 25 | | 1310 | |
| | | 4µL RB + 4µL CD | | 0 | | 1140 | 0.8 |
| | | | | 25 | | 880 | |
| | | 8µL CD | | 0 | | 770 | 1.5 |
| | | | | 25 | | 1130 | |
| | 1/2 | 8µL RB | | 0 | | 430 | 3.4 |
| | | | | 25 | | 1480 | |
| | 1/3 | 8µL RB | | 0 | | 470 | 3.3 |
| | | | | 25 | | 1540 | |
| | | | 100µL | 0 | | 410 | 3.7 |
| | | | | 25 | | 1510 | |
| | | 8µL CD | 80µL | 0 | | 460 | 2.9 |
| | | | | 25 | | 1330 | |
| | | | 100µL | 0 | | 460 | 2.9 |
| | | | | 25 | | 1340 | |
| | | 4µL RB + 4µL CD | 80µL | 0 | | 440 | 2.6 |
| | | | | 25 | | 1160 | |
| | | 8µL RB + 8µL CD | | 0 | | 420 | 3.5 |
| | | | | 25 | | 1470 | |
| Wash at 15min | Full | 8µL RB | 80µL | 0 | | 660 | 3.2 |
| | | | | 25 | | 2200 | |
| 30min read | 1/2 | | | 0 | | 550 | 3.7 |
| | | | | 25 | | 2050 | |
| | 1/3 | | | 0 | | 600 | 3.1 |
| | | | | 25 | | 1880 | |

FIG. 55

| Low conc duplex conj | Vol | 20 | | | |
|---|---|---|---|---|---|
| | Parameter | Sugars + Casein | LH | PdG | Water |
| | Type | Conc | Conc | Conc | Remainder |
| | Final | 0.5 | 3 | 2 | - |
| | Init | 2 | 42.3 | 46.3 | - |
| | Vol (µL) | 5.0 | 1.4 | 0.9 | 12.7 |

| High conc duplex conj | Vol | 20 | | | |
|---|---|---|---|---|---|
| | Parameter | Sugars + Casein | LH | PdG | Water |
| | Type | Conc | Conc | Conc | Remainder |
| | Final | 0.5 | 6 | 3 | - |
| | Init | 2 | 42.3 | 46.3 | - |
| | Vol (µL) | 5.0 | 2.8 | 1.3 | 10.9 |

FIG. 56

Figure 57:
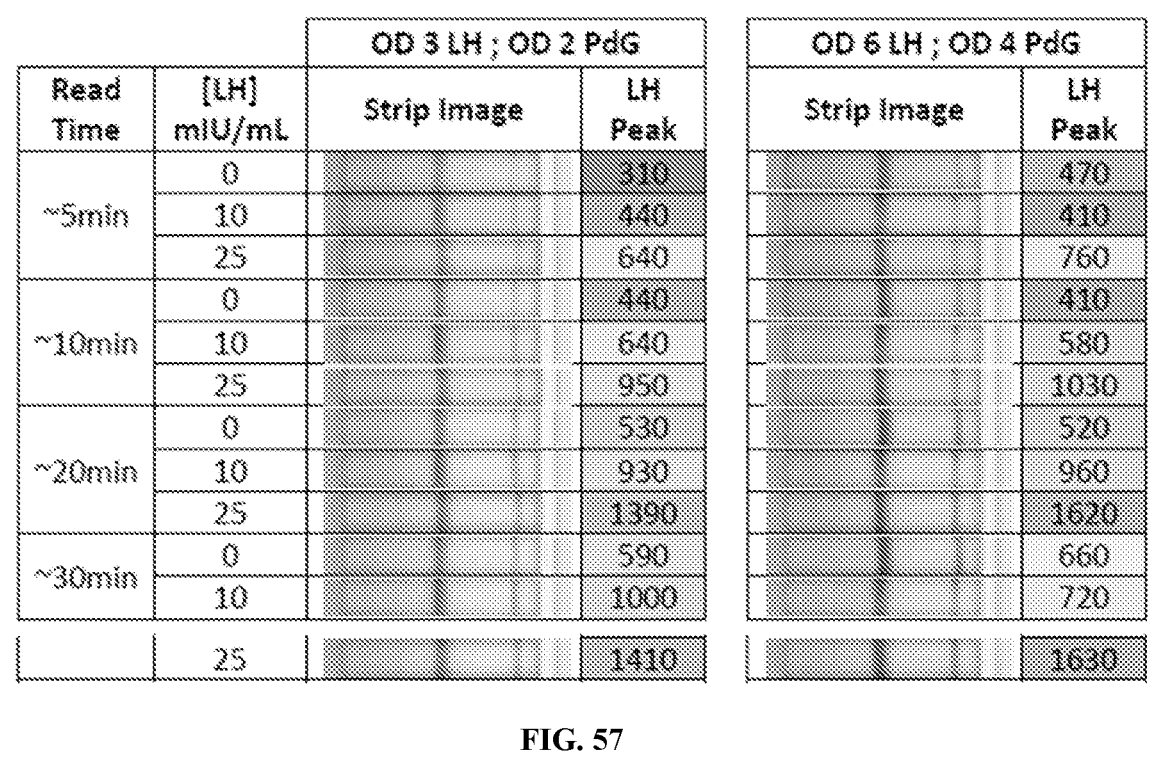

| Read Time | [LH] mIU/mL | OD 3 LH ; OD 2 PdG | | OD 6 LH ; OD 4 PdG | |
| --- | --- | --- | --- | --- | --- |
| | | Strip Image | LH Peak | Strip Image | LH Peak |
| ~5min | 0 | | 310 | | 470 |
| | 10 | | 440 | | 410 |
| | 25 | | 640 | | 760 |
| ~10min | 0 | | 440 | | 410 |
| | 10 | | 640 | | 580 |
| | 25 | | 950 | | 1030 |
| ~20min | 0 | | 530 | | 520 |
| | 10 | | 930 | | 960 |
| | 25 | | 1390 | | 1620 |
| ~30min | 0 | | 590 | | 660 |
| | 10 | | 1000 | | 720 |
| | 25 | | 1410 | | 1630 |

| Low conc duplex conj | Vol | 40 | | | |
| --- | --- | --- | --- | --- | --- |
| | Parameter | Sugars + Casein | LH | PdG | Water |
| | Type | Conc | Conc | Conc | Remainder |
| | Final | 0.5 | 3 | 2 | - |
| | Init | 2 | 42.3 | 46.3 | - |
| | Vol (μL) | 10.0 | 2.8 | 1.7 | 25.4 |

| Low conc duplex conj with NEW Ab4-Au-8 conjugates (see OD number for PdG) | Vol | 32 | | | |
| --- | --- | --- | --- | --- | --- |
| | Parameter | Sugars + Casein | LH | PdG | Water |
| | Type | Conc | Conc | Conc | Remainder |
| | Final | 0.5 | 3 | 2 | - |
| | Init | 2 | 42.3 | 25.26 | - |
| | Vol (μL) | 8.0 | 2.3 | 2.5 | 19.2 |

FIG. 58

| [LH] spiked (mIU/mL) | Previous PdG Conj | New PdG Conj |
|:---:|:---:|:---:|
| 0 | | |
| 1 | | |
| 2 | | |
| 4 | | |

FIG. 59

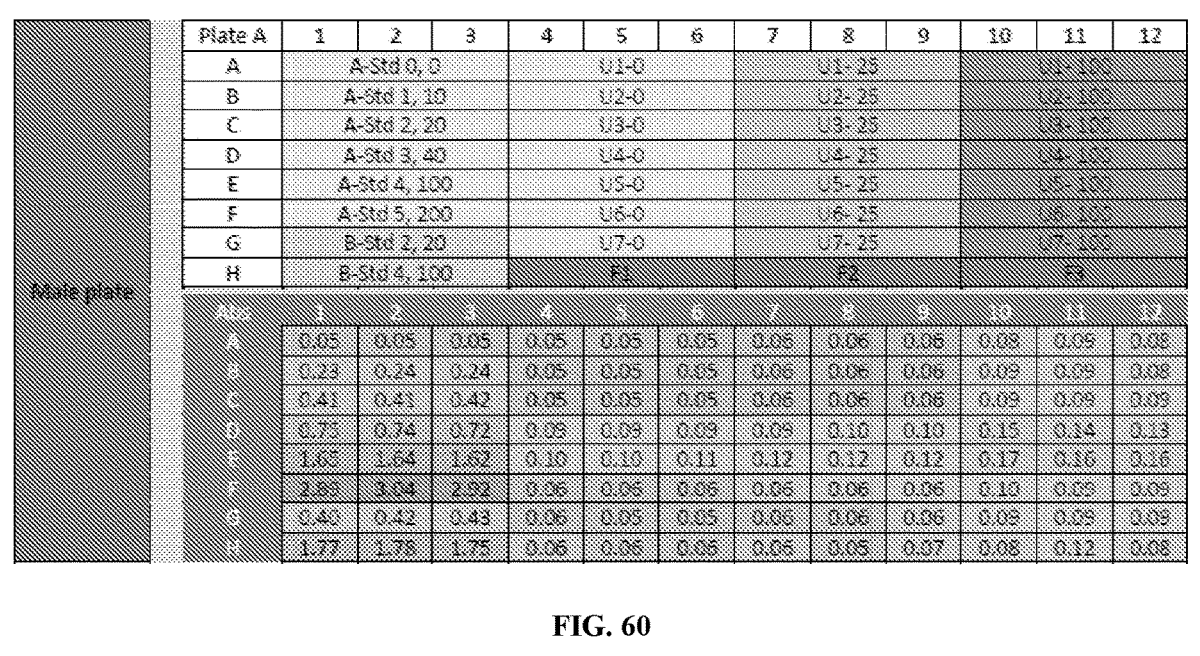

| Plate A | 1 | 2 | 3 | 4 | 5 | 6 | 7 | 8 | 9 | 10 | 11 | 12 |
|---|---|---|---|---|---|---|---|---|---|---|---|---|
| A | A-Std 0, 0 | | | U1-0 | | | U1-25 | | | | | |
| B | A-Std 1, 10 | | | U2-0 | | | U2-25 | | | | | |
| C | A-Std 2, 20 | | | U3-0 | | | U3-25 | | | | | |
| D | A-Std 3, 40 | | | U4-0 | | | U4-25 | | | | | |
| E | A-Std 4, 100 | | | U5-0 | | | U5-25 | | | | | |
| F | A-Std 5, 200 | | | U6-0 | | | U6-25 | | | | | |
| G | B-Std 3, 20 | | | U7-0 | | | U7-25 | | | | | |
| H | B-Std 4, 100 | | | R1 | | | R2 | | | | | |

|  |  |  |  |  |  |  |  |  |  |  |  |  |
|---|---|---|---|---|---|---|---|---|---|---|---|---|
|  | 0.05 | 0.05 | 0.05 | 0.05 | 0.05 | 0.05 | 0.05 | 0.06 | 0.06 | 0.09 | 0.09 | 0.09 |
|  | 0.23 | 0.24 | 0.24 | 0.05 | 0.05 | 0.05 | 0.06 | 0.06 | 0.06 | 0.09 | 0.09 | 0.09 |
|  | 0.41 | 0.41 | 0.42 | 0.05 | 0.05 | 0.05 | 0.06 | 0.06 | 0.08 | 0.09 | 0.09 | 0.09 |
|  | 0.73 | 0.74 | 0.72 | 0.08 | 0.09 | 0.09 | 0.09 | 0.10 | 0.10 | 0.15 | 0.14 | 0.13 |
|  | 1.85 | 1.84 | 1.82 | 0.10 | 0.10 | 0.11 | 0.12 | 0.12 | 0.12 | 0.17 | 0.16 | 0.16 |
|  | 2.83 | 3.04 | 2.82 | 0.05 | 0.05 | 0.05 | 0.06 | 0.06 | 0.06 | 0.10 | 0.09 | 0.09 |
|  | 0.40 | 0.41 | 0.43 | 0.06 | 0.06 | 0.05 | 0.06 | 0.06 | 0.06 | 0.08 | 0.08 | 0.09 |
|  | 1.77 | 1.78 | 1.75 | 0.05 | 0.05 | 0.05 | 0.05 | 0.05 | 0.07 | 0.08 | 0.12 | 0.08 |

FIG. 60

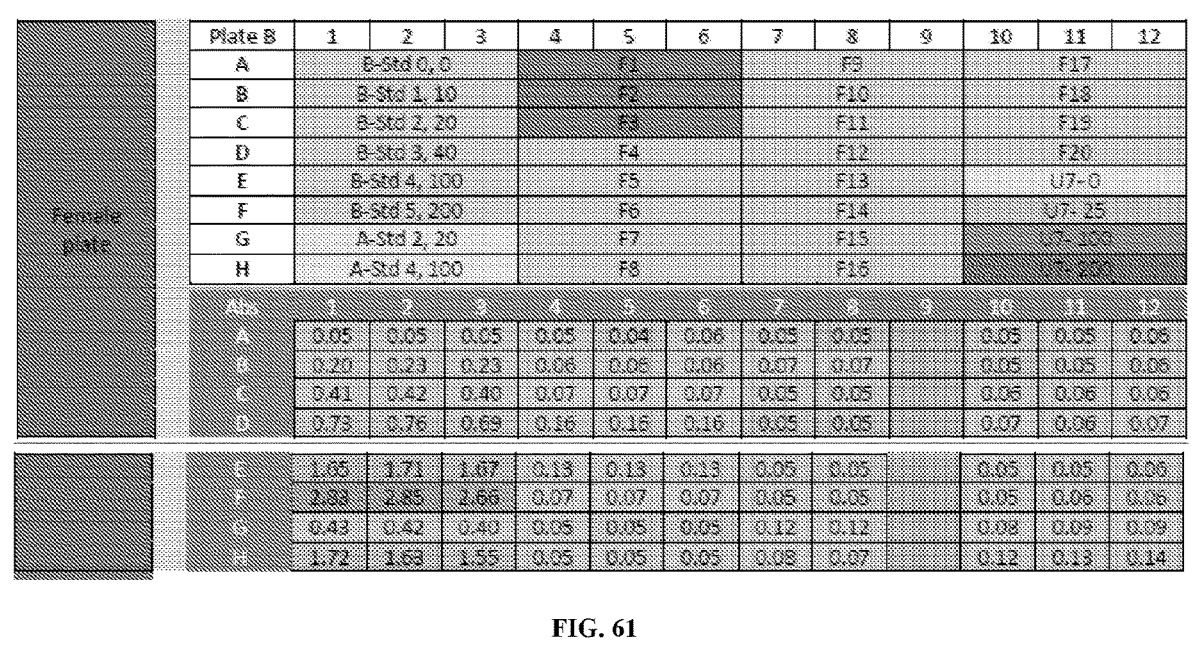

| Plate B | 1 | 2 | 3 | 4 | 5 | 6 | 7 | 8 | 9 | 10 | 11 | 12 |
|---|---|---|---|---|---|---|---|---|---|---|---|---|
| A | B-Std 0, 0 | | | | | | | F9 | | | F17 | |
| B | B-Std 1, 10 | | | | F2 | | | F10 | | | F18 | |
| C | B-Std 2, 20 | | | | F3 | | | F11 | | | F19 | |
| D | B-Std 3, 40 | | | F4 | | | | F12 | | | F20 | |
| E | B-Std 4, 100 | | | F5 | | | | F13 | | | U7-0 | |
| F | B-Std 5, 200 | | | F6 | | | | F14 | | | U7-25 | |
| G | A-Std 2, 20 | | | F7 | | | | F15 | | | | |
| H | A-Std 4, 100 | | | F8 | | | | F16 | | | | |

| | 1 | 2 | 3 | 4 | 5 | 6 | 7 | 8 | 9 | 10 | 11 | 12 |
|---|---|---|---|---|---|---|---|---|---|---|---|---|
| | 0.05 | 0.05 | 0.05 | 0.05 | 0.04 | 0.06 | 0.05 | 0.05 | | 0.05 | 0.05 | 0.05 |
| | 0.20 | 0.23 | 0.23 | 0.06 | 0.06 | 0.06 | 0.07 | 0.07 | | 0.05 | 0.05 | 0.06 |
| | 0.41 | 0.42 | 0.40 | 0.07 | 0.07 | 0.07 | 0.05 | 0.05 | | 0.06 | 0.06 | 0.06 |
| | 0.73 | 0.76 | 0.69 | 0.16 | 0.16 | 0.16 | 0.05 | 0.05 | | 0.07 | 0.08 | 0.07 |

| | 1 | 2 | 3 | 4 | 5 | 6 | 7 | 8 | 9 | 10 | 11 | 12 |
|---|---|---|---|---|---|---|---|---|---|---|---|---|
| | 1.85 | 1.71 | 1.67 | 0.13 | 0.13 | 0.13 | 0.05 | 0.05 | | 0.05 | 0.05 | 0.05 |
| | 2.89 | 2.85 | 2.66 | 0.07 | 0.07 | 0.07 | 0.05 | 0.05 | | 0.05 | 0.06 | 0.06 |
| | 0.43 | 0.42 | 0.42 | 0.05 | 0.05 | 0.05 | 0.12 | 0.12 | | 0.09 | 0.09 | 0.09 |
| | 1.72 | 1.63 | 1.55 | 0.05 | 0.05 | 0.05 | 0.08 | 0.07 | | 0.13 | 0.13 | 0.14 |

FIG. 61

| Plate 1 | 1 | 2 | 3 | 4 | 5 | 6 | 7 | 8 | 9 | 10 | 11 | 12 |
|---|---|---|---|---|---|---|---|---|---|---|---|---|
| A | Std 0- 0 | | | Urine A- 0 | | | Urine B- 0 | | | Urine C- 0 | | |
| B | Std 1- 10 | | | Urine A- 2 | | | Urine B- 2 | | | Urine C- 2 | | |
| C | Std 2- 20 | | | Urine A- 5 | | | Urine B- 5 | | | Urine C- 5 | | |
| D | Std 3- 40 | | | Urine A- 15 | | | Urine B- 15 | | | Urine C- 15 | | |
| E | Std 4- 100 | | | Urine A- 40 | | | Urine B- 40 | | | Urine C- 40 | | |
| F | Std 5- 200 | | | Urine A- 70 | | | Urine B- 70 | | | Urine C- 70 | | |
| G | Urine D- 10 (screening) | | | Urine A- 100 | | | Urine B- 100 | | | Urine C- 100 | | |
| H | Urine D- 70 (screening) | | | Urine A- 200 | | | Urine B- 200 | | | Urine C- 200 | | |

FIG. 62

| Plate | 1 | 2 | 3 | 4 | 5 | 6 | 7 | 8 | 9 | 10 | 11 | 12 |
|---|---|---|---|---|---|---|---|---|---|---|---|---|
| A | 0.05 | 0.05 | 0.06 | 0.05 | 0.05 | 0.05 | 0.09 | 0.06 | 0.06 | 0.05 | 0.05 | 0.05 |
| B | 0.12 | 0.12 | 0.11 | 0.05 | 0.05 | 0.05 | 0.06 | 0.07 | 0.07 | 0.05 | 0.06 | 0.06 |
| C | 0.19 | 0.19 | 0.19 | 0.06 | 0.06 | 0.06 | 0.07 | 0.07 | 0.07 | 0.06 | 0.06 | 0.06 |
| D | 0.34 | 0.32 | 0.33 | 0.09 | 0.08 | 0.09 | 0.09 | 0.10 | 0.09 | 0.08 | 0.08 | 0.08 |
| E | 0.84 | 0.78 | 0.78 | 0.15 | 0.16 | 0.16 | 0.15 | 0.15 | 0.15 | 0.11 | 0.09 | 0.12 |
| F | 1.60 | 1.55 | 1.45 | 0.25 | 0.25 | 0.25 | 0.22 | 0.22 | 0.21 | 0.14 | 0.16 | 0.17 |
| G | 0.08 | 0.07 | 0.08 | 0.34 | 0.34 | 0.35 | 0.31 | 0.33 | 0.30 | 0.21 | 0.18 | 0.22 |
| H | 0.21 | 0.19 | 0.20 | 0.59 | 0.61 | 0.62 | 0.57 | 0.60 | 0.66 | 0.42 | 0.37 | 0.28 |

FIG. 63

| Std # | [LH] (mIU/mL) | Male Plate | | | | Female Plate | | | |
|---|---|---|---|---|---|---|---|---|---|
| | | Avg | Reps | | | Avg | Rep | | |
| 0 | 0 | 0.05 | 0.05 | 0.05 | 0.05 | 0.05 | 0.05 | 0.05 | 0.05 |
| 1 | 10 | 0.24 | 0.23 | 0.24 | 0.24 | 0.22 | 0.20 | 0.23 | 0.23 |
| 2 | 20 | 0.41 | 0.41 | 0.41 | 0.42 | 0.41 | 0.41 | 0.42 | 0.40 |
| 3 | 40 | 0.74 | 0.75 | 0.74 | 0.72 | 0.73 | 0.73 | 0.76 | 0.69 |
| 4 | 100 | 1.64 | 1.65 | 1.64 | 1.62 | 1.67 | 1.65 | 1.71 | 1.67 |
| 5 | 200 | 2.95 | 2.89 | 3.04 | 2.92 | 2.78 | 2.83 | 2.85 | 2.66 |

Standard curves from Male and Female plates $y = 0.0144x + 0.1351$
$R^2 = 0.9973$ $y = 0.01371x + 0.13211$
$R^2 = 0.99122$ ● Male Stds
● Female Stds

[LH] (mIU/mL)

Abs

| Set | Strip Image | LH | PdG | Sample | LH Values | | PdG Values | | |
|---|---|---|---|---|---|---|---|---|---|
| | | | | | Duplex Cass | LH ELISA | Duplex Cass | PdG ELISA | PdG-only Cass (previous data) |
| ELISA standards | | | | S0 | 710 | 0.05 | 12850 | | |
| | | | | S1 | 8990 | 0.22 | 14570 | | |
| | | | | S2 | 11780 | 0.41 | 13620 | | |
| | | | | S3 | 14160 | 0.73 | 13690 | | |
| | | | | S4 | 16510 | 1.67 | 12680 | | |
| | | | | S5 | 17680 | 2.78 | 14150 | | |
| Female samples | | | | F1 | 650 | 0.05 | 1050 | 0.34 | 4068 |
| | | | | F2 | 650 | 0.06 | 1620 | 0.49 | 6490 |
| | | | | F3 | 1250 | 0.07 | 990 | 0.45 | 4040 |
| | | | | F4 | 6710 | 0.16 | 3040 | 0.51 | 6498 |
| | | | | F5 | 4050 | 0.13 | 2130 | 0.60 | 6775 |
| | | | | F6 | 1500 | 0.07 | 420 | 0.27 | 1085 |
| | | | | F7 | 510 | 0.05 | 8240 | 1.10 | 12490 |
| | | | | F8 | 280 | 0.05 | 8140 | 1.15 | 13568 |
| | | | | F9 | 450 | 0.05 | 7750 | 0.97 | 11790 |
| | | | | F10 | 1920 | 0.07 | 1090 | 0.48 | 5233 |
| | | | | F11 | 390 | 0.05 | 7430 | 0.58 | 12346 |
| | | | | F12 | 250 | 0.05 | 8570 | 0.91 | 10943 |
| | | | | F13 | 490 | 0.05 | 1460 | 0.46 | 5220 |
| | | | | F14 | 610 | 0.05 | 6950 | 0.84 | 12455 |
| | | | | F15 | 3910 | 0.13 | 990 | 0.39 | 4895 |
| | | | | F16 | 1040 | 0.07 | 1070 | 0.43 | 4445 |
| | | | | F17 | 510 | 0.05 | 930 | 0.40 | 3130 |
| | | | | F18 | 640 | 0.05 | 4810 | 0.70 | 9779 |
| | | | | F19 | 820 | 0.06 | 3899 | 0.67 | 7920 |
| | | | | F20 | 1010 | 0.06 | 1170 | 0.40 | 4343 |

FIG. 65

| Sample ID | CL Peak | PdG Peak | LH Peak | Sample ID | CL Peak | PdG Peak | LH Peak |
|---|---|---|---|---|---|---|---|
| F1 | 8060 | 1000 | 540 | F11 | 6250 | 8090 | 500 |
| | | | | | 5510 | 7580 | 420 |
| | 8510 | 950 | 620 | | 5450 | 7600 | 530 |
| | 8460 | 870 | 580 | | | | |
| F2 | 8250 | 1360 | 590 | F12 | 3150 | 5280 | 530 |
| | 7880 | 1620 | 650 | | 5570 | 7240 | 310 |
| | 8050 | 2090 | 700 | | 4740 | 6130 | 360 |
| | 7860 | 1770 | 500 | | 4510 | 6570 | 430 |
| F3 | 8150 | 1080 | 1030 | F13 | 7005 | 1590 | 520 |
| | 7780 | 570 | 1260 | | 6240 | 1270 | 450 |
| | 8140 | 570 | 1290 | | 7170 | 1540 | 390 |
| | 7680 | 920 | 980 | | 8440 | 2030 | 960 |
| F4 | 8140 | 1540 | 6210 | F14 | 7560 | 9110 | 360 |
| | 6690 | 1240 | 6690 | | 6250 | 7110 | 540 |
| | 7020 | 1390 | 8480 | | 6510 | 7440 | 440 |
| | 8020 | 2970 | 6150 | | 6630 | 8250 | 390 |
| F5 | 7200 | 1810 | 3570 | F15 | 7360 | 1430 | 3190 |
| | | | | | 7070 | 1520 | 3580 |
| | 8230 | 2090 | 4040 | | 8040 | 1960 | 3860 |
| | 7770 | 1760 | 3980 | | 7300 | 1510 | 3310 |
| F6 | 8480 | 240 | 1240 | F16 | 8010 | 1410 | 860 |
| | 7770 | 570 | 1140 | | 7240 | 1220 | 910 |
| | 7880 | 270 | 1220 | | 7570 | 980 | 1080 |
| | 8920 | 240 | 1210 | | 8100 | 1140 | 1060 |
| F7 | 6120 | 8040 | 490 | F17 | 8610 | 1000 | 550 |
| | 5010 | 8320 | 710 | | 8300 | 1130 | 430 |
| | 5340 | 7880 | 450 | | 7500 | 740 | 540 |
| | 6060 | 8970 | 340 | | 8460 | 1060 | 570 |
| F8 | 2840 | 9780 | 390 | F18 | 6090 | 4790 | 660 |
| | 3480 | 8270 | 580 | | 7650 | 6550 | 610 |
| | 3420 | 10460 | 300 | | 6660 | 5570 | 540 |
| | 3660 | 10420 | 380 | | 6550 | 5220 | 610 |
| F9 | 4740 | 8850 | 380 | F19 | 5550 | 2640 | 1080 |
| | 4250 | 8530 | 335 | | 7250 | 3800 | 990 |
| | 4500 | 8930 | 385 | | 6580 | 5130 | 1040 |
| | 5050 | 8970 | 380 | | 8100 | 3440 | 1070 |
| F10 | 7270 | 1130 | 1830 | F20 | 7850 | 950 | 990 |
| | 7640 | 1620 | 1460 | | 8650 | 1230 | 990 |
| | 5810 | 1370 | 2080 | | 8050 | 1180 | 950 |
| | | | | | 7790 | 1220 | 990 |

FIG. 67

| Sample - LH Conc | Replicates | | Averages | |
|---|---|---|---|---|
| | PdG Peak | LH Peak | Avg of 4 PdG TLs | Avg of 2 LH TLs |
| U1-0 | 5970 | 380 | 5408 | 420 |
| | 5680 | 480 | | |
| U1-100 | 4960 | 530 | | 530 |
| | | | | |
| U2-0 | 8410 | 360 | 8065 | 360 |
| | 7740 | 360 | | |
| U2-100 | 7210 | 310 | | 375 |
| | 7850 | 440 | | |
| U3-0 | 5750 | 690 | 5905 | 610 |
| | 5180 | 530 | | |
| U3-100 | 5560 | 2120 | | 1810 |
| | 7130 | 1500 | | |
| U4-0 | 1250 | 2200 | 950 | 1825 |
| | 550 | 1450 | | |
| U4-100 | 1170 | 2460 | | 2665 |
| | 830 | 2870 | | |
| U5-0 | 2630 | 1830 | 2848 | 1875 |
| | 2370 | 1920 | | |
| U5-100 | 2850 | 3230 | | 3370 |
| | 3540 | 3510 | | |
| U6-0 | 7530 | 800 | 6383 | 760 |
| | 5750 | 720 | | |
| U6-100 | 6420 | 1650 | | 1600 |
| | 5830 | 1550 | | |
| U7-0 | 6670 | 630 | 6815 | 625 |
| | 6650 | 620 | | |
| U7-100 | 7420 | 1570 | | 1685 |
| | 6520 | 1800 | | |

FIG. 68

| Sample | PdG Avg | Unspiked LH (0mIU/mL) | Spiked LH (100mIU/mL) |
|--------|---------|------------------------|------------------------|
| U1 | 5408 | 420 | 530 |
| U2 | 8065 | 360 | 375 |
| U3 | 5905 | 610 | 1610 |
| U4 | 950 | 1825 | 2665 |
| U5 | 2848 | 1975 | 3370 |
| U6 | 6383 | 760 | 1600 |
| U7 | 6815 | 625 | 1685 |
| U8 | 7257 | 557 | |
| U9 | 6490 | 673 | |
| U10 | 4780 | 1340 | |
| U11 | 6860 | 917 | |

FIG. 69

| Sample | Spiked LH (mIU/mL) | LH TL | Avg |
|---|---|---|---|
| U6 | 0 | 800 | 760 |
| | | 720 | |
| | 100 | 1650 | 1600 |
| | | 1550 | |
| | 200 | 4140 | 3973 |
| | | 3730 | |
| | | 4050 | |

| Sample | Spiked LH (mIU/mL) | LH TL | Avg |
|---|---|---|---|
| U7 | 0 | 630 | 673 |
| | | 620 | |
| | | 770 | |
| | 10 | 510 | 550 |
| | | 590 | |
| | | 550 | |
| | 20 | 890 | 807 |
| | | 760 | |
| | | 770 | |
| | 50 | 1090 | 967 |
| | | 1000 | |
| | | 810 | |
| | 75 | 1230 | 1220 |
| | | 1250 | |
| | | 1180 | |
| | 100 | 1570 | 1733 |
| | | 1800 | |
| | | 1830 | |

FIG. 70

Figure 72:
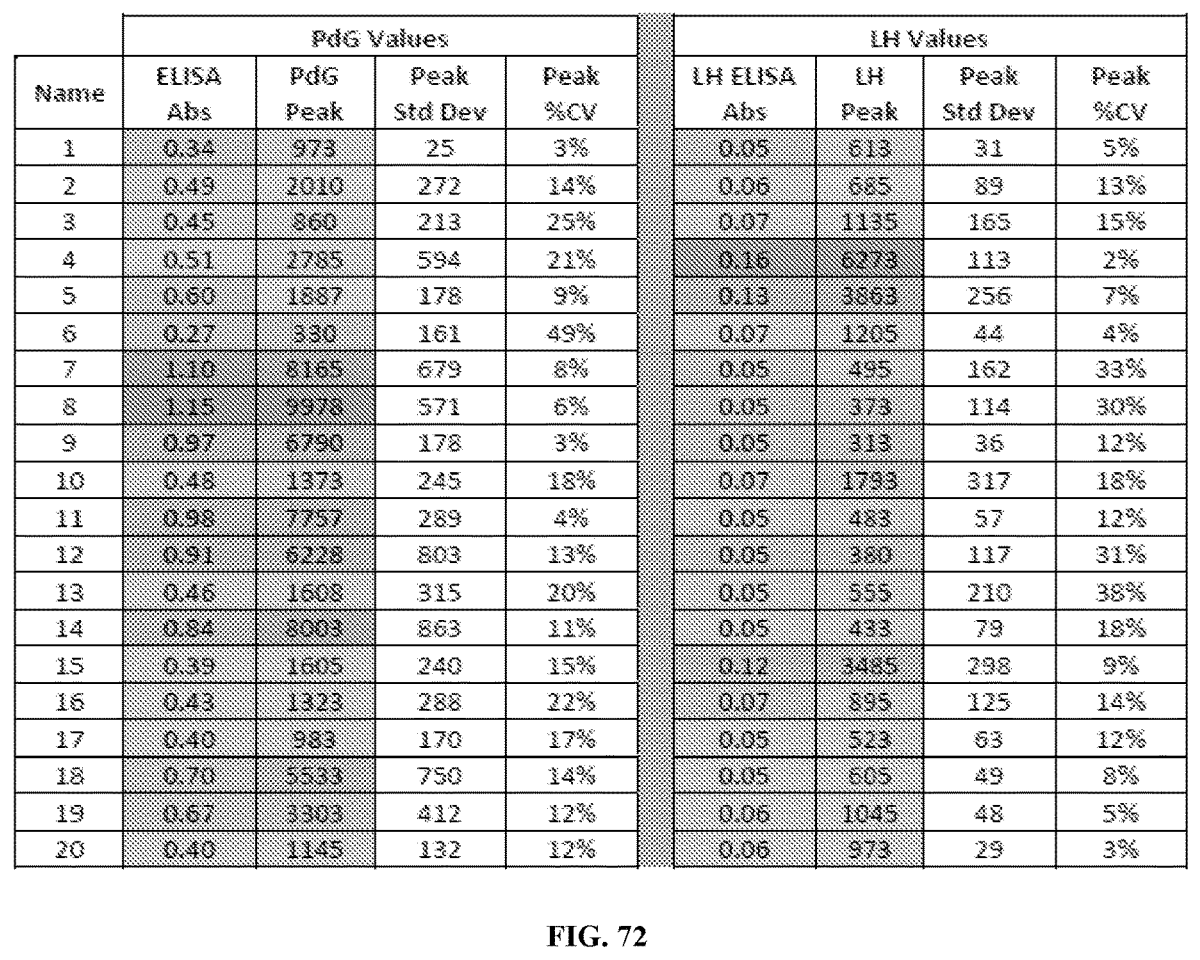

| Name | PdG Values | | | | LH Values | | | |
| --- | --- | --- | --- | --- | --- | --- | --- | --- |
| | ELISA Abs | PdG Peak | Peak Std Dev | Peak %CV | LH ELISA Abs | LH Peak | Peak Std Dev | Peak %CV |
| 1 | 0.34 | 973 | 25 | 3% | 0.05 | 613 | 31 | 5% |
| 2 | 0.49 | 2010 | 272 | 14% | 0.06 | 665 | 89 | 13% |
| 3 | 0.45 | 860 | 213 | 25% | 0.07 | 1135 | 165 | 15% |
| 4 | 0.51 | 2785 | 594 | 21% | 0.16 | 6273 | 113 | 2% |
| 5 | 0.60 | 1887 | 178 | 9% | 0.13 | 3863 | 256 | 7% |
| 6 | 0.27 | 330 | 161 | 49% | 0.07 | 1205 | 44 | 4% |
| 7 | 1.10 | 8165 | 679 | 8% | 0.05 | 495 | 162 | 33% |
| 8 | 1.15 | 9978 | 571 | 6% | 0.05 | 373 | 114 | 30% |
| 9 | 0.97 | 6790 | 178 | 3% | 0.05 | 313 | 36 | 12% |
| 10 | 0.48 | 1373 | 245 | 18% | 0.07 | 1793 | 317 | 18% |
| 11 | 0.98 | 7757 | 289 | 4% | 0.05 | 483 | 57 | 12% |
| 12 | 0.91 | 6228 | 803 | 13% | 0.05 | 380 | 117 | 31% |
| 13 | 0.46 | 1608 | 315 | 20% | 0.05 | 555 | 210 | 38% |
| 14 | 0.84 | 8003 | 863 | 11% | 0.05 | 433 | 79 | 18% |
| 15 | 0.39 | 1605 | 240 | 15% | 0.12 | 3485 | 298 | 9% |
| 16 | 0.43 | 1323 | 288 | 22% | 0.07 | 895 | 125 | 14% |
| 17 | 0.40 | 983 | 170 | 17% | 0.05 | 523 | 63 | 12% |
| 18 | 0.70 | 5533 | 750 | 14% | 0.05 | 605 | 49 | 8% |
| 19 | 0.67 | 3303 | 412 | 12% | 0.06 | 1045 | 48 | 5% |
| 20 | 0.40 | 1145 | 132 | 12% | 0.06 | 973 | 29 | 3% |

Sync and visualize results

Analysis of test strip

Provide urine sample on test strip

Scan strip via smartphone

METHODS, DEVICES, AND SYSTEMS FOR DETECTING ANALYTE LEVELS

CROSS REFERENCE

This present application is a National Stage Entry of International Application No. PCT/US2019/038173, filed Jun. 20, 2019, which claims the benefit of U.S. Provisional Application No. 62/688,970, filed Jun. 22, 2018, each of which is incorporated herein by reference in its entirety.

BACKGROUND

Existing at-home methods of monitoring the ovulatory cycle of a woman are limited to three primary types: paper-based urine test strips, basal body temperature readers, and saliva test strips. The existing at-home methods of monitoring the ovulatory cycle of a woman do not successfully inform a woman of when she is ovulating.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

The present disclosure provides a computer-implemented method comprising processing pixel intensities in a hue, saturation, value, or lightness color space of an image of an indicator associated with a health status of a subject, thereby quantifying said indicator, and providing a report on said health status.

The present disclosure also provides a computer-implemented system comprising a digital processing device comprising at least one processor, an operating system configured to perform executable instructions, a memory, and a computer program including instructions executable by the digital processing device to quantify an analyte using an image processing algorithm, said algorithm being configured to process pixel intensities of a hue, saturation, value, or lightness color space of an image of said analyte, and said analyte is indicative of an ovulation status of a subject.

The present disclosure provides a non-transitory computer-readable storage media encoded with a computer program including instructions executable by a processor to quantify an analyte, wherein said instructions process pixel intensities of a hue, saturation, value, or lightness color space of an image of an analyte, wherein said analyte is indicative of an ovulation status of a subject.

The present disclosure also provides a substrate (e.g., a lateral flow device) comprising particles comprising a first analyte capture agent, a test area comprising a second analyte capture agent, a control area comprising a control agent, and an orientation element.

The present disclosure provides a kit comprising two more lateral flow devices, wherein each lateral flow device independently comprises particles comprising a first analyte capture agent, a test area comprising a second analyte capture agent, a control area comprising a control agent, and an orientation element.

The present disclosure provides a system comprising:
a) a lateral flow device; and
b) a computer-implemented system comprising a digital processing device comprising at least one processor, an operating system configured to perform executable instructions, a memory, and a computer program including instructions executable by the digital processing device to quantify an analyte using an image processing algorithm, said algorithm being configured to process pixel intensities of a hue, saturation, value, or lightness color space of an image of said analyte, and said analyte is indicative of an ovulation status of a subject.

The present disclosure also provides a method of manufacturing said lateral flow device comprising particles comprising a first analyte capture agent, a test area comprising a second analyte capture agent, a control area comprising a control agent, and an orientation element, wherein said orientation element is used to normalize said control area of a batch of said lateral flow device.

The present disclosure provides a computer implemented method comprising: (a) capturing, by a camera of a mobile telecommunications device, an image of a detection region on a substrate in contact with a biological sample from a subject, wherein the detection region comprises a detector that undergoes a change in a visible property of the detection region in response to contact with an analyte in the biological sample, wherein the analyte is associated with a health profile of the subject; (b) processing, by a processor of the mobile telecommunications device, pixel intensities of the image of the detection region on the substrate in contact with the biological sample, thereby quantifying an amount of the analyte in the detection region on the substrate to determine a concentration of the analyte in the biological sample, wherein the pixel intensities correspond to the visible property of the detector; and (c) providing, by the processor of the mobile telecommunications device, a report on the health profile of the subject based on the concentration of the analyte.

The present disclosure also provides a computer program product comprising a non-transitory computer-readable medium having computer-executable code encoded therein, the computer-executable code adapted to be executed to implement a method comprising: (a) (a) providing an analyte processing and reporting system of a mobile telecommunications device, wherein the analyte processing and reporting system comprises: (i) an optical sensor module; (ii) a quantification module; and (iii) a visualization module; (b) capturing, by the optical sensor module, an image of a detection region on a substrate in contact with a biological sample from a subject, wherein the detection region comprises a detector that undergoes a change in a visible property of the detection region in response to contact with an analyte in the biological sample, wherein the analyte is associated with a health profile of the subject; (c) processing, by the quantification module, pixel intensities of the image of the detection region on the substrate in contact with the biological sample, thereby quantifying an amount of the analyte in the detection region on the substrate to determine a concentration of the analyte in the biological sample, wherein the pixel intensities correspond to the visible property of the detector; and (d) providing, by the visualization module, a report on the health profile of the subject based on the concentration of the analyte in the biological sample.

BRIEF DESCRIPTION OF THE DRAWINGS

FIG. 26 BOTTOM PANEL shows the results for the image intensities along the vector depicted in FIG. 26 TOP PANEL.

FIG. 36 shows a schematic of the strip described in EXAMPLE 5 part a.

FIG. 41 shows Axxin peak values and strip images for a blank sample and ELISA standards.

FIG. 44 shows Axxin values and images for strips used to make a lateral flow assay (LFA) standard curve.

FIG. 45 shows Axxin generated values and images of cassettes run with samples F1-F20.

FIG. 52 shows test line (TL) images and Axxin peak value measurements of strips run with different amounts of LH gold and, LH, and PdG present.

FIG. 53 shows a comparison of test strips images and Axxin peak values from test strips run with new vs. previous conjugate preparations.

FIG. 55 shows images and Axxin peak value reading of strips run under various conditions.

FIG. 56 shows a description of gold conjugate preparations.

FIG. 57 shows images and Axxin peak values from strips read at various times under various conditions.

FIG. 58 shows a description of gold conjugate preparations.

FIG. 59 shows a comparison of two different preparations of Ab4-Au-8 gold conjugates run with samples spiked with different amounts of LH.

FIG. 60 shows the plate layout and absorbance values as determined by ELISA for LH for male urine samples.

FIG. 61 shows the plate layout and absorbance values as determined by ELISA for LH for female urine samples.

FIG. 62 shows the plate set up for the experimental results represented in FIG. 63.

FIG. 63 shows absorbance values measured by ELISA for LH.

FIG. 65 shows a comparison of LH and PdG Axxin peak values vs. absorbance values measured by ELISA.

FIG. 67 shows Axxin control line (CL) values, PdG peak values, and LH peak values for twenty female urine samples tested with LH/PdG duplex cassettes.

FIG. 68 shows Axxin PdG and LH peak values for spiked and unspiked male urine samples.

FIG. 69 shows a summary of Axxin peak values obtained for male urine samples that were unspiked or spiked with LH.

FIG. 70 shows Axxin peak values of male urine samples spiked with various concentrations of LH.

FIG. 72 shows a comparison Axxin peak values obtained with LH/PdG cassettes compared with corresponding ELISA absorbance values.

FIG. 75 shows a comparison of peak value measurements obtained with an Axxin reader and a developed custom lateral flow immunoassay strip reader.

DETAILED DESCRIPTION OF THE INVENTION

A. Introduction

Figure 1A:
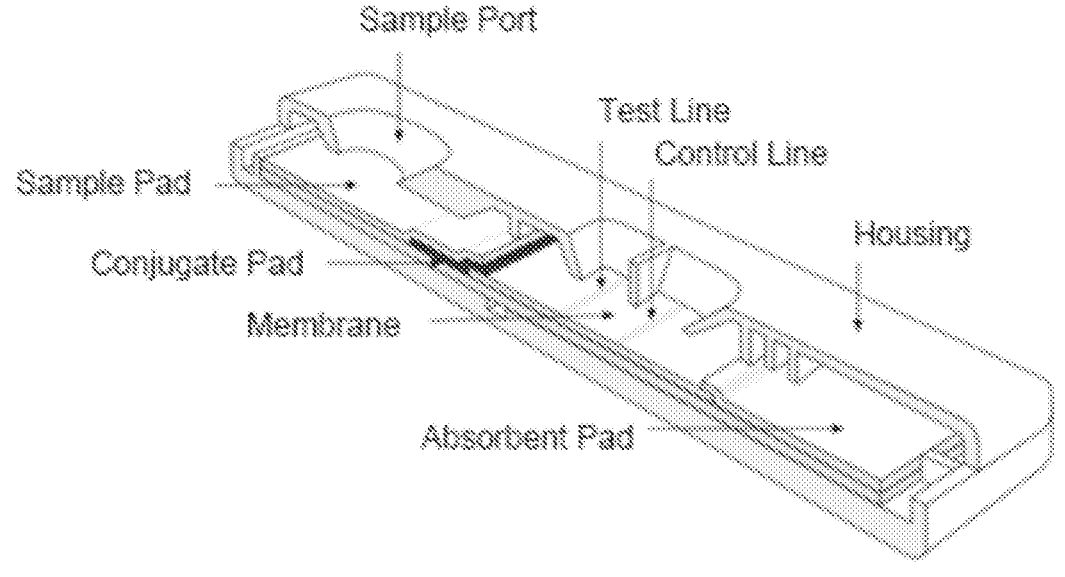
FIG. 1A illustrates the traditional components of a lateral flow device.

The amount of an analyte in a biological sample can be indicative of a health status of a subject. For example, the amount of an analyte can be indicative of a subject's fertility status, pregnancy, medication adherence, cancer, neurological disorder, inflammatory disorder, or infectious disease state, or of a prenatal disease or newborn health status. Quantification of an analyte (e.g., a hormone) requires collection of a biological sample (e.g., urine or blood), and often requires one or more visits to a physician's office.

Current methods of obtaining measurements of hormones require blood tests, are qualitative, and/or produce binary results based on a comparison against pre-determined thresholds. Additionally, current methods of qualitative hormone measurements fail to detect hormone imbalances, and in the case of conventional tests, do not accommodate women with irregular cycles, do not track a woman's personalized hormone curve, and are unable to simultaneously track multiple hormones.

The present disclosure describes methods, devices, and systems for accurately quantifying an analyte in a biological sample obtained from a subject to determine a subject's health status. A device of the disclosure can be used to quantify the amount of one or more analytes. Additionally, the methods, devices, and systems of the disclosure can eliminate the need for frequent clinic visits and/or blood tests. The methods, devices, and systems of the disclosure can also allow the visualization of analyte data via an intuitive app on a smart phone.

The present disclosure describes a computer-implemented method comprising processing pixel intensities in a hue, saturation, value, or lightness color space of an image of an indicator associated with a health status of a subject, thereby quantifying the indicator and providing a report on the subject's health status. Further, the present disclosure describes a computer-implemented system comprising a digital processing device comprising at least one processor, an operating system configured to perform executable instructions, a memory, and a computer program including instructions executable by the digital processing device to quantify an analyte using an image processing algorithm, the algorithm being configured to process pixel intensities of a hue, saturation, value, or lightness color space of an image of the analyte, and the analyte is indicative of a health status of a subject.

The present disclosure also describes non-transitory computer-readable storage media encoded with a computer program including instructions executable by a processor to quantify an analyte, wherein the instructions process pixel intensities of a hue, saturation, value, or lightness color space of an image of an analyte, wherein the analyte is indicative of an ovulation status of a subject. The present disclosure describes a kit comprising two or more substrates (e.g., lateral flow devices) described herein.

The present disclosure further describes a system comprising: a) a substrate (e.g., lateral flow device); and b) a computer-implemented system comprising a digital processing device comprising at least one processor, an operating system configured to perform executable instructions, a memory, and a computer program including instructions executable by the digital processing device to quantify an analyte using an image processing algorithm, the algorithm being configured to process pixel intensities of a hue, saturation, value, or lightness color space of an image of the analyte, and the analyte is indicative of a health status of a subject.

B. Devices a. Quantitative Next Generation Test Strip

Substrates (e.g., lateral flow devices), also known as lateral flow immunochromatographic assays or lateral flow strips, are devices that detect the presence or absence of a target analyte in a sample without the need for specialized and costly equipment. Lateral flow devices are typically used for medical diagnostics for home testing, point-of-care (POC) testing, or laboratory use. Lateral flow devices are also rapid and inexpensive diagnostic tests with long shelf lives that do not require refrigerated storage. A well-known application of a lateral flow device is the home pregnancy test and the home ovulation test.

A lateral flow device can be assembled with several key components: 1) a sample pad for application of a sample; 2) a conjugate pad containing dried colored particles; 3) a membrane striped with a test and control line; and 4) a wicking pad. The sample is placed on the sample pad (backing). The conjugate pad is where the sample interacts with the embedded particles to detect analytes of interest. The intensity of a test line is correlated to the amount of hormone present. FIG. 1A illustrates the traditional components of a lateral flow device.

Lateral flow devices are based on a series of capillary beds, such as pieces of porous paper, microstructured polymer, or sintered polymers. The materials have the capacity to transport a fluid, such as urine, spontaneously. The lateral flow device can be made of an absorbent material, such as nitrocellulose.

The sample pad of a lateral flow device acts as a sponge and holds a biological sample fluid, such as urine, blood, serum, or saliva. In some embodiments, the sample fluid is urine. The sample pad of a lateral flow device can also hold a non-biological sample, such as a food product containing an allergen.

A method or device of the disclosure comprises, prior to processing, contacting the lateral flow device with a bioprocessing sample comprising a target analyte. A subject can use a urine sample that is collected as a stream or contained in a cup with a lateral flow device. A method or device of the disclosure can also use a running buffer, or function without a running buffer. Additionally, a method or device of the disclosure can use a sample that has been treated or processed, or can use an untreated or unprocessed sample.

Once soaked, the fluid migrates to the conjugate pad, where a conjugate is stored. The conjugate pad can contain a dried format of bio-active particles in a salt-sugar matrix that contains materials to guarantee an optimized chemical reaction between the target molecule (e.g., antigen) and its chemical partner (e.g., antibody) that has been immobilized on the particle's surface.

Figure 1B:
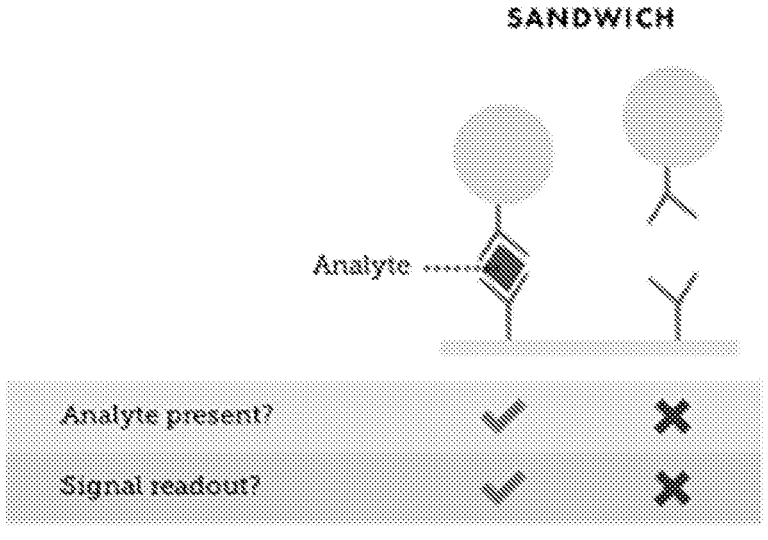
FIG. 1B illustrates a schematic of a sandwich assay.

Sandwich assays can be employed to detect relatively large analytes. If the analyte has at least two distinct binding sites, a sandwich assay can be developed where an antibody to one binding site is conjugated to a nanoparticle, and an antibody to another binding site is used for the test line. If the analyte is present in a sample, the analyte becomes the "meat" of the sandwich and binds the nanoparticle conjugate to the test line, yielding a positive signal. The sandwich format results in a signal intensity that is proportional to the amount of the analyte present in the sample. FIG. 1B illustrates a schematic of a sandwich assay. A sandwich assay utilizes a free-flowing antibody mixed with the sample and a fixed antibody, embedded the test line and the control line. The sandwich assay method allows for maximum binding of analytes present in the sample.

Sandwich assays can use various antibodies to detect the presence of an analyte. For example, antibodies that can be used in sandwich assays include antibodies against bilirubin, testosterone, follicle stimulating hormone (FSH), anti-mullerian hormone (AMH), estrogen, acylglycines, beta-carotene, cholesterol, creatinine, fructose, glucose, glutaric acid, histamine, insulin, lactate, pyruvate, urea, uric acid, gluten, gliadin, ketones, inositol, beta-2-microglobulin (B2M), calcitonin, fibrin, fibrinogen, C-reactive protein (CRP), *Chlamydia trachomatis, Neisseria gonorrhea, Borrelia burgdorferi, Mycoplasma pneumoniae, Mycobacterium tuberculosis, Bordetella pertussis*, and amyloid beta protein.

Colored particles can be used to indicate whether a test is positive or negative. The ruby red colored line in lateral flow strips arises from the binding of spherical gold nanoparticles (e.g., 40 nm spherical gold nanoparticles) via a conjugated antibody. The optical plasmon resonance of the gold nanoparticles strongly absorbs green and blue light. In the most common configuration, a colored line at the test location indicates a positive test and presence of the analyte. A second line at the control location can serve as a positive control and indicate that the test was valid. Colored particles can be plasmonic metal particles with tailored optical signatures. The colored particles can be nanoparticles, such as gold nanoparticles. The colored particles can also be gold particles, such as colloidal gold particles. Additionally, the colored beads can be cellulose nano-beads. Colloidal gold particles can be bound to a first analyte capture agent, such as an antibody that specifically binds to the analyte.

A lateral flow device of the present disclosure can comprise particles comprising a first analyte capture agent, a test area comprising a second analyte capture agent, a control area comprising a control agent, and an orientation element. The test area and control area can be within the orientation element, and the particles can be gold particles (e.g., colloidal gold particles). The first and second analyte capture agents can be antibodies that specifically bind to the analytes. The control agent can specifically bind to the first analyte capture agent, and can be an antibody. The particles can be a) contacted with a biological sample comprising an analyte in the test area, wherein the biological sample is contacted with the particles under conditions that permit binding between the particles and the analyte; and b) contacted with the control agent in the control area, wherein the particles are contacted with the control agent under conditions that permit binding between the particles and the control agent.

The lateral flow device of the disclosure can comprise a test area and a control area. The test area can comprise a second analyte capture agent. For example, the second analyte capture agent can be an antibody that specifically binds to the analyte. The control area can comprise a control agent that specifically binds to the first analyte capture agent. For example, the control agent can be an antibody that specifically binds to the first analyte capture agent. A test area of a lateral flow device can comprise captured analyte-bound particles, and a control area of the lateral flow device can comprise capture analyte-unbound particles.

The lateral flow device of the disclosure can comprise multiple test areas and/or multiple control areas. A test area can have one region or multiple regions comprising the same or different capture agents. For example, a test area can comprise a first region with a first capture agent for a first analyte, and a second region with a second capture agent for a second analyte.

The lateral flow device of the disclosure can further comprise an orientation element. The orientation element can be a film with an image that doubles as a sample protectant and window for the lateral flow device. The orientation element can also be used to normalize the control area of a batch of lateral flow test strips. The orientation element can comprise information, such as information on a batch number or a code that indicates a sample's batch ID, control line histogram, color sampling, membrane sample, biomarkers, and an intensity model. The orientation element can contain up to 2,953 bytes of information. When a user scans the strip, the orientation element can be used to focus on the correct region of interest, and the code can be attached to information associated with the specific batch of lateral flow test strips (e.g., batch number, batch ID, control line histogram, color sampling, membrane sample, biomarkers, or an intensity model). For example, the orientation element can contain information that allows a computer program to normalize signals between batches to account for inter-batch variability (e.g. in manufacturing). The orientation element can be used to locate the test area and the control area of the lateral flow device. In some embodiments, the test area and control area can be located within the orientation element.

A lateral flow device of the disclosure can be used to quantify more than one analyte. For example, a lateral flow device of the disclosure can be used to quantify 2, 3, 4, 5, 6, 7, 8, 9, or 10 analytes. In some embodiments, a lateral flow device of the disclosure can be used to quantify 2 analytes. In some embodiments, a lateral flow device of the disclosure can be used to quantify 3 analytes. In some embodiments, a lateral flow device of the disclosure can be used to quantify 4 analytes. In some embodiments, a lateral flow device of the disclosure can be used to quantify 5 analytes. In some embodiments, a lateral flow device of the disclosure can be used to quantify 6 analytes.

A device of the disclosure can have an analysis time that provides a fast and convenient readout to a user. For example, an analysis time can be under about 6 minutes, about 5 minutes, about 4 minutes, or about 3 minutes. In some embodiments, a device of the disclosure can have an analysis time that is under about 6 minutes. In some embodiments, a device of the disclosure can have an analysis time that is under about 5 minutes. In some embodiments, a device of the disclosure can have an analysis time that is under about 4 minutes. In some embodiments, a device of the disclosure can have an analysis time that is under about 3 minutes.

A device of the disclosure can produce results that are stable, allowing a user a convenient window within which to analyze the results. For example, a device of the disclosure can produce results that are stable for at least about 1 minute, about 2 minutes, about 3 minutes, about 4 minutes, about 5 minutes, about 6 minutes, about 7 minutes, about 8 minutes, about 9 minutes, or about 10 minutes. In some embodiments, a device of the disclosure can produce results that are stable for at least about 3 minutes. In some embodiments, a device of the disclosure can produce results that are stable for at least about 5 minutes.

A method or device of the disclosure can have a minimal detection concentration that is sensitive enough to provide accurate results across a broad physiological range. For example, a method of device of the disclosure can have a minimal detection concentration that is from about 1 mIU/mL to about 20 mIU/mL. A method or device of the disclosure has a minimal detection concentration of about 1 mIU/mL, about 2 mIU/mL, about 3 mIU/mL, about 4 mIU/mL, about 5 mIU/mL, about 6 mIU/mL, about 7 mIU/mL, about 8 mIU/mL, about 9 mIU/mL, or about 10 mIU/mL. In some embodiments, a method or device of the disclosure has a minimal detection concentration of about 1 mIU/mL. In some embodiments, a method or device of the disclosure has a minimal detection concentration of about 2.5 mIU/mL. In some embodiments, a method or device of the disclosure has a minimal detection concentration of about 5 mIU/mL. Determining the concentration of the analyte in the biological sample can be based on a training set of quantified concentrations of a plurality of analytes. The training set can comprise at least about 50, 100, 200, 300, 400, 500, 600, 700, 800, 900, 1000, 2000, 3000, 4000, 5000, 6000, or more images whose analyte concentration can be quantified and/or subsequently annotated by a substrate reader. The training set can comprise at most about 6000, 5000, 4000, 3000, 2000, 1000, 900, 800, 700, 600, 500, 400, 300, 200, 100, 50, or less images whose analyte concentration can be quantified and/or subsequently annotated by a substrate reader. The substrate reader can be a desktop lateral flow assay reader (e.g., Axxin Lateral Flow Reader Model AX-2X-S). The training set can be generated during validations in a lab.

A method or device of the disclosure can have, if applicable, a limit of quantification that is about 1%±concentration of the analyte, about 2%±concentration of the analyte, about 3%±concentration of the analyte, about 4%±concentration of the analyte, about 5%±concentration of the analyte, about 6%±concentration of the analyte, about 7%±concentration of the analyte, about 8%±concentration of the analyte, about 9%±concentration of the analyte, or about 10%±concentration of the analyte. In some embodiments, a method or device of the disclosure can have a limit of quantification that is about 10%±concentration. In some embodiments, a method or device of the disclosure can have a limit of quantification that is about 7.5%±concentration. In some embodiments, a method or device of the disclosure can have a limit of quantification that is about 5%±concentration. In some embodiments, a method or device of the disclosure can have a limit of quantification that is about 2.5%±concentration.

A method or device of the disclosure can also have, if applicable, a maximum detection concentration that is about 1 mIU/mL, about 10 mIU/mL, about 20 mIU/mL, about 30 mIU/mL, about 40 mIU/mL, about 50 mIU/mL, about 60 mIU/mL, about 70 mIU/mL, about 80 mIU/mL, about 90 mIU/mL, about 100 mIU/mL, about 110 mIU/mL, about 120 mIU/mL, about 130 mIU/mL, about 140 mIU/mL, about 150 mIU/mL, about 160 mIU/mL, about 170 mIU/mL, about 180 mIU/mL, about 190 mIU/mL, or about 200 mIU/mL. In some embodiments, a method or device of the disclosure can have a maximum detection concentration that is about 1 mIU/mL. In some embodiments, a method or device of the disclosure can have a maximum detection concentration that is about 50 mIU/mL. In some embodiments, a method or device of the disclosure can have a maximum detection concentration that is about 100 mIU/mL. In some embodiments, a method or device of the disclosure can have a maximum detection concentration that is about 150 mIU/mL. In some embodiments, a method or device of the disclosure can have a maximum detection concentration that is about 200 mIU/mL.

A method or device of the disclosure can have clinical sensitivity that is comparable to results obtained using a blood test for quantification of an analyte. Sensitivity can be defined as the number of true positive results (TP) divided by the number of true positive results (TP) plus the number of false negative results (FN) multiplied by 100 to obtain a percentage (i.e., sensitivity=[(TP)/(TP+FN)]×100). A method or device of the disclosure can have clinical sensitivity that is at least about 70%, about 75%, about 80%, about 85%, about 90%, or about 95%. In some embodiments, a method or device of the disclosure can have clinical sensitivity that is at least about 70%. In some embodiments, a method or device of the disclosure can have clinical sensitivity that is at least about 80%. In some embodiments, a method or device of the disclosure can have clinical sensitivity that is at least about 90%. In some embodiments, a method or device of the disclosure can have clinical sensitivity that is at least about 95%.

A method or device of the disclosure can have specificity that is comparable to results obtained using a blood test for quantification of an analyte. Specificity can be defined as the number of true negative results (TN) divided by the number of true negative results (TN) plus the number of false positive results (FP), multiplied by 100 to obtain a percentage (i.e., specificity=[(TN)/(TN+FP)]×100). For example, a method or device of the disclosure can have specificity that is at least about 70%, about 75%, about 80%, about 85%, about 90%, or about 95%. In some embodiments, a method or device of the disclosure can have specificity that is at least about 70%. In some embodiments, a method or device of the disclosure can have specificity that is at least about 80%. In some embodiments, a method or device of the disclosure can have specificity that is at least about 90%. In some embodiments, a method or device of the disclosure can have specificity that is at least about 95%.

A device of the disclosure can be stable for a sufficient length of time to allow convenient storage of the device before use in analyzing a sample. For example, a device of the disclosure can have stability for greater than about 6 months, about 12 months, about 18 months, about 24 months, about 30 months, about 36 months, about 42 months, about 48 months, about 54 months, or about 60 months at room temperature. In some embodiments, a device of the disclosure can have stability for greater than about 6 months. In some embodiments, a device of the disclosure can have stability for greater than about 12 months.

A device of the disclosure can comprise a cartridge, a handle, and a holder. In some embodiments the cartridge is disposable. In some embodiments the cartridge is about 0.3 inches, 0.4 inches, 0.5 inches, 0.6 inches, 0.7 inches, 0.8 inches, or 0.9 inches in width by 1 inch, 2 inch, 3 inch, 4 inch, 5 inch, 6 inch, or 7 inches or more in length. In some embodiments the cartridge is of equal length and width. A cartridge can be made of any material. Non-limiting examples of materials a cartridge of the disclosure can be made out of include plastics, advanced biodegradable plastics, paper, foam, and cardboard.

A cartridge of the disclosure can hold a lateral flow immunoassay. In some embodiments a cartridge of the disclosure holds multiple immunoassays. In some embodiments a cartridge of the disclosure holds 1, 2, 3, 4, 5, 6, 7, 8, 9, 10 or more than 10 immunoassays.

Figure 2:
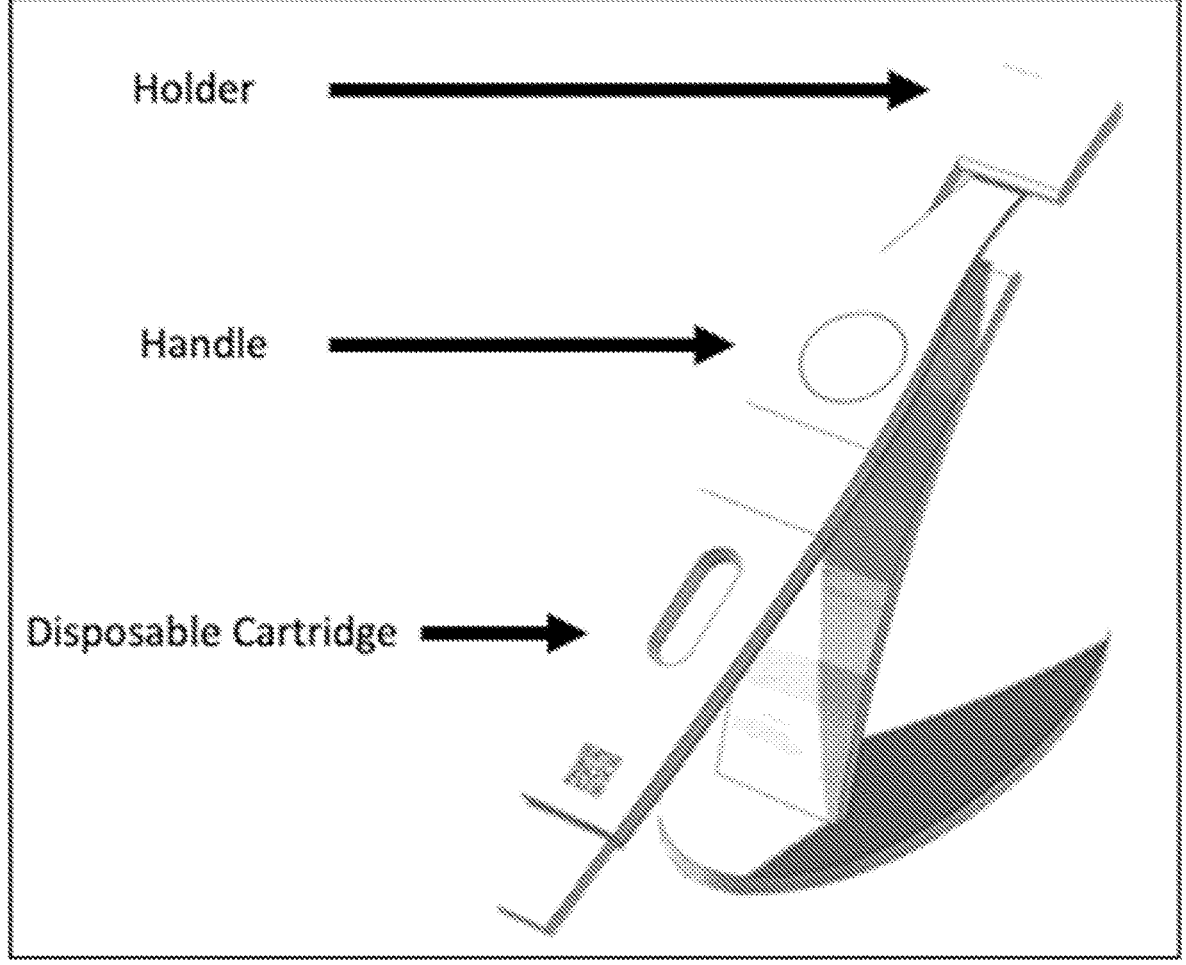
FIG. 2 shows a schematic of a device of the disclosure.

In some embodiments a handle of a device of the disclosure is reusable. In some embodiments, a user can click a new test cartridge to a handle, provide a biological sample and rest the handle/cartridge in a holder while the test populates. After a predefined time limit a user can scan the test with a device such as a smartphone and analyze the results. Upon completion of a test a user can eject the cartridge into the trash and secure the handle to the holder for further use. A schematic of a device of the disclosure is shown in FIG. 2.

b. Optical Sensor

In order to quantify an analyte on any of devices herein, one or more optical sensors is utilized. Such optical sensors interpret the intensity of the test area and the control area for a target analyte, and provide a quantitative measure of the amount of an analyte present in a sample. The optical sensor can also use an orientation element located on the lateral flow device to locate the test area and the control area. An optical sensor can comprise a high-resolution camera configured to take an image of the test area and the control area of the lateral flow device strip. For example, the optical sensor can be a countertop device, a stand-alone device, or a camera of a mobile phone. An optical sensor can be equipped to send image data to a cloud system for interpretation.

An optical sensor of the disclosure can have several components, including 1) a raw camera sensor; 2) LED lights; 3) a microcontroller; 4) an aperture; 5) a shutter; and 6) a simple optical lens. For example, an optical sensor of the disclosure can have an optical system comprising of a fluid (e.g. poly(dimethylsiloxane) (PDMS)) or solid (e.g., glass) material lens and a complementary metal-oxide semiconductor (CMOS) or a charge-coupled device (CCD) image sensor.

An optical sensor of the disclosure can be a low resolution optical sensor or a high resolution optical sensor. For example, the optical sensor can have a resolution of about 5 megapixels, about 6 megapixels, about 7 megapixels, about 8 megapixels, about 9 megapixels, about 10 megapixels, about 11 megapixels, about 12 megapixels, about 13 megapixels, about 14 megapixels, about 15 megapixels, about 16 megapixels, about 17 megapixels, about 18 megapixels, about 19 megapixels, or about 20 megapixels. In some embodiments, the optical sensor can have a resolution of about 5 megapixels. In some embodiments, the optical sensor can have a resolution of about 7 megapixels. In some embodiments, the optical sensor can have a resolution of about 12 megapixels. In some embodiments, the optical sensor can have a resolution of about 16 megapixels.

An optical sensor of the disclosure can be required to be a certain distance away from the lateral flow device of the disclosure. For example, an optical sensor of the disclosure can be required to be about 3 inches, about 3.5 inches, about 4 inches, about 4.5 inches, about 5 inches, about 5.5 inches, or about 6 inches away from a lateral flow device of the disclosure. In some embodiments, an optical sensor can be about 3 inches away from a lateral flow device. In some embodiments, an optical sensor can be about 4 inches away from a lateral flow device. In some embodiments, an optical sensor can be about 5 inches away from a lateral flow device. In some embodiments, an optical sensor can be about 6 inches away from a lateral flow device.

C. Methods of Use

A method or device of the disclosure can quantify an amount of an analyte that is associated with a health status of a subject (e.g., the status of a disease or condition). For example, a method or device of the disclosure can quantify an amount of analyte that is associated with fertility, a prenatal disease, new born health status, medication adherence status, cancer, an immune or inflammatory disorder, or a neurological disorder. A device of the disclosure can be used to quantify an analyte at two time points to determine a change in analyte quantity over time. For example, an analyte can be quantified from one day to the next (e.g., to determine a change in a cyclical hormone), before and after treatment (e.g., to determine an efficacy of treatment), or over the course of several months (e.g., to determine the progression/regression of a disease).

a. Fertility Hormones

A woman can be diagnosed as infertile when she has not been able to get pregnant after 1) one year of trying for a woman under the age of 35; or 2) six months of trying for a woman 35 years or older. Women who can get pregnant but are unable to stay pregnant can also be considered infertile. About 12.5% of women in the United States between the ages of 15-44 have difficulty getting or staying pregnant.

Pregnancy is the result of a multi-step process: 1) a woman's body must release an egg from one of her ovaries (i.e., ovulation); 2) the egg must travel through a fallopian tube toward the uterus; 3) a man's sperm must join with the egg and fertilize the egg; and 4) the fertilized egg must attach to the inside of the uterus (i.e., implantation).

Luteinizing hormone (LH) is one of the hormones produced by the pituitary gland. Ordinarily, LH is secreted at very low levels throughout a woman's menstrual cycle. Once a developing egg follicle reaches a certain size, LH secretion surges to high levels. The LH surge triggers ovulation about 24 to 36 hours later. The LH surge is important because it initiates the beginning of ovulation and a woman's fertile period. Once an egg is released, the egg is only viable for about 24 hours. Thus, identifying the fertile window is critical for a woman's ability to get pregnant. The present disclosure describes methods, devices, and systems for accurately detecting a woman's fertile days based on her individual hormone profile. The present disclosure also describes a personalized urine-based diagnostic test used to detect a woman's most fertile days by accurately measuring key fertility hormones. The methods, devices, and systems of the disclosure can be used to accurately measure four key fertility hormones and track a woman's personalized hormone curve in the privacy of her own home. The methods or devices of the present disclosure can also predict the fertile window of women with irregular cycles or hormone imbalances. The methods, devices, and systems of the disclosure can eliminate the need for frequent clinic visits and/or blood tests.

Estradiol: Shortly before ovulation, estradiol levels surge and then fall immediately after ovulation. Elevated estradiol exerts a positive effect to the brain to release LH resulting in the LH surge. The methods, devices, and systems of the disclosure can detect a surge and fall in estradiol to confirm ovulation.

Luteinizing hormone: LH is low throughout the cycle but has an acute rise or surge, triggering ovulation. Elevated LH is the final push for an egg to be released (i.e., ovulation). The methods, devices, and systems of the disclosure can detect a surge in LH to predict ovulation.

Progesterone: Progesterone levels are typically low but peak following ovulation, which is the ultimate indicator that ovulation has occurred. Elevated levels of progesterone begin to prepare the uterus for implantation of an embryo. Pregnanediol glucuronide (PdG) is a metabolite of progesterone. The methods, devices, and systems of the disclosure can detect a peak in progesterone to confirm ovulation. In some embodiments a peak in progesterone can be detected via measurement of PdG.

Human chorionic gonadotropin (hCG): hCG is produced by a developing embryo during pregnancy. The level of hCG in the urine is used to confirm pregnancy. The methods, devices, and systems of the disclosure can detect the presence of hCG to confirm pregnancy.

Follicular phase: The first part of the follicular phase is menstruation, where the uterine lining is shed if an egg was not fertilized during the previous cycle. In the second part of the follicular phase, ovarian follicles mature and get ready to release a subsequent egg. The methods, devices, and systems of the disclosure can be used during the follicular phase to measure amounts of estradiol, progesterone, and LH to confirm that a woman has not ovulated.

Ovulation phase: Estradiol stimulates the production of a large amount of LH, causing the LH surge. A mature egg is released from the ovaries into the fallopian tubes. The egg has 24 hours to be fertilized. The methods, devices, and systems of the disclosure can be used during the ovulation phase to detect a surge in LH and predict ovulation.

Secretory phase: Progesterone levels increase and induce production of estradiol. If the egg is fertilized, progesterone levels will remain high and prepare the uterus for implantation of an embryo. If the egg was not fertilized, progesterone levels will decrease to trigger menstruation. The methods, devices, and systems of the disclosure can be used during the secretory phase to measure amounts of progesterone to confirm that a woman has ovulated. The methods, devices, and systems of the disclosure can also be used at the end of the secretory phase to measure amounts of hCG to confirm the presence or absence of a pregnancy.

Figure 3:
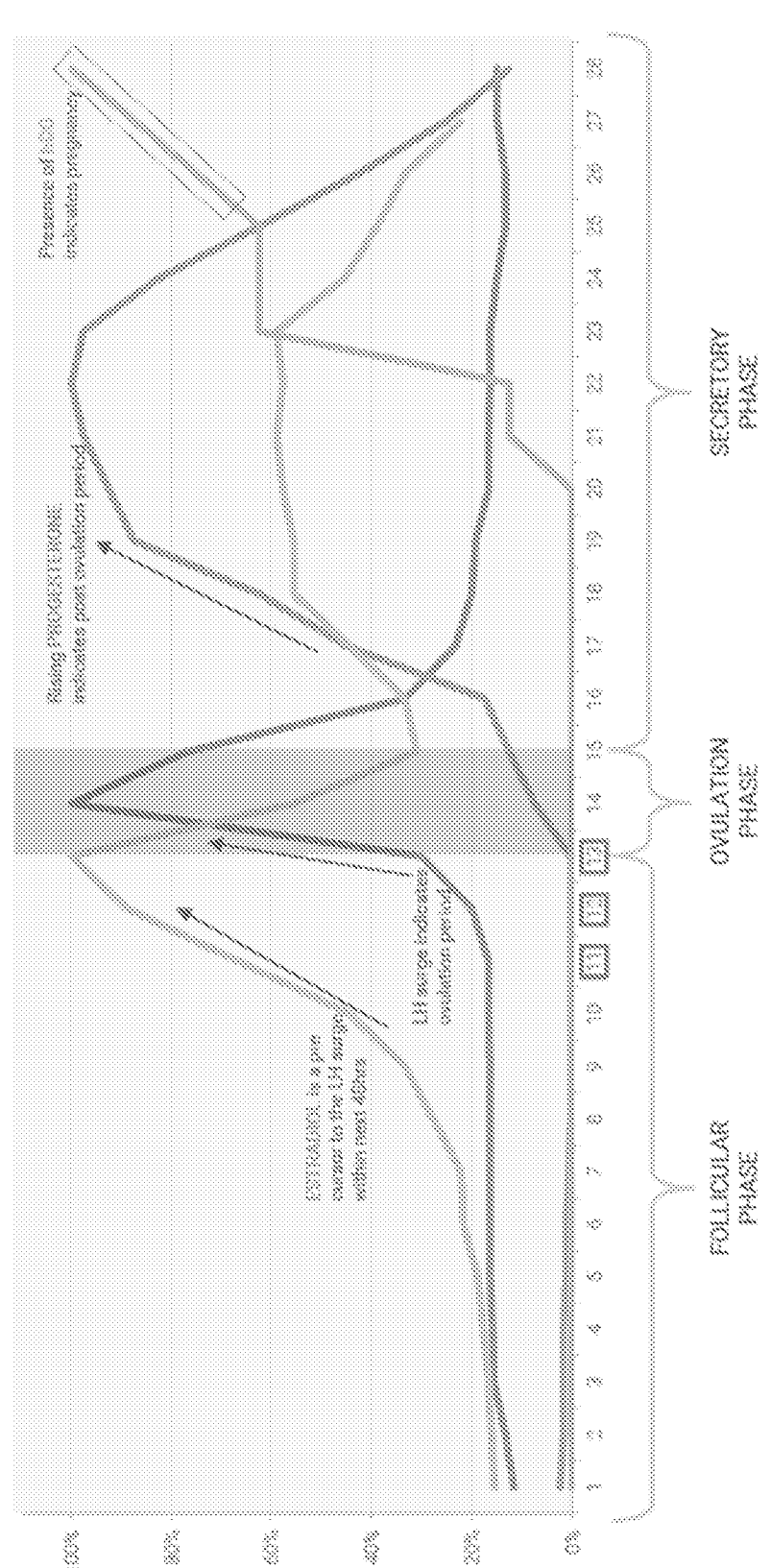
FIG. 3 illustrates changes to key hormones involved in the menstrual cycle over the three stages of the cycle.

FIG. 3 illustrates changes to the key hormones and the three stages of a menstrual cycle.

A lateral flow device of the disclosure can detect the presence or absence of fertility hormones, such as LH, progesterone, estradiol, hCG, testosterone, follicle-stimulating hormone (FSH), anti-muellerian hormone (AMH), or estrogen. In some embodiments, a lateral flow device of the disclosure targets LH. A method or device of the disclosure can be used to track a woman's menstrual cycle and predict a woman's fertile period by quantitatively measuring LH, estradiol, progesterone, and/or hCG levels. A method or device of the disclosure can also be used to predict a woman's ovulation date by quantitatively measuring LH and estradiol, confirm ovulation by quantitatively measuring progesterone levels, or confirm pregnancy by quantitatively measuring hCG levels.

A subject can use the lateral flow device of the disclosure using a urine sample for daily testing. A subject can use the lateral flow device of the disclosure every day to monitor the presence or absence of an analyte. A woman can use the lateral flow device of the disclosure daily or every two days during her menstrual cycle to monitor ovulation and/or confirm pregnancy. A woman can use the lateral flow device of the disclosure starting day 1 of her menstrual cycle, or for a period of time during her menstrual cycle, for example, between day 8 and day 28 of her menstrual cycle. In some embodiments, a woman can use the lateral flow device of the disclosure daily starting Day 10 to the day ovulation is confirmed to monitor ovulation. A woman can also use the lateral flow device of the disclosure daily after confirming pregnancy to monitor progesterone levels. For example, a subject can collect a urine sample every day, and apply the sample to a lateral flow device of the disclosure to quantify the amount of LH using antibodies against LH. The subject can quantify LH in daily urine samples starting day 1 of her menstrual cycle, or for a period of time during her menstrual cycle (e.g., Day 8-28) for a duration of 6 months to predict the timing of ovulation.

A lateral flow device of the disclosure can be used to quantify LH and be used as an ovulation test. A lateral flow device of the disclosure can be used to quantify hCG and be used as a pregnancy test or to track a woman's pregnancy. A lateral flow device of the disclosure can be used to quantify LH and hCG, and be used as an ovulation test and a pregnancy test. Further, a lateral flow device of the disclosure can be used to detect ectopic pregnancies, molar pregnancies, and non-viable pregnancies. A lateral flow device of the disclosure can be a self-contained disposable, single-use device.

b. Prenatal Disease and New Born Health Status

A method or device of the disclosure can be used to determine a health status of a subject, wherein the health status is a newborn health status. A subject's health status also can be a prenatal disease. In the case of detecting a prenatal disease, a sample (e.g., a blood sample) used with the devices, methods, and systems of the present disclosure can be taken from a pregnant woman. A method or device of the disclosure can be used to detect analytes in newborns that are indicative of amino acid disorders (e.g., phenylketonuria (PKU)), fatty acid oxidation disorders (e.g., medium chain acyl-CoA dehydrogenase deficiency (MCADD), short-chain acyl-CoA dehydrogenase deficiency (SCADD)), endocrinopathies (e.g., congenital hypothyroidism, congenital adrenal hyperplasia (CAH)), hemoglobinopathies, organic acidemias, cystic fibrosis, urea cycle disorders (e.g, citrullinemia, argininosuccinic aciduria, argininemia), lysosomal storage disorders, hearing loss, congenital heart defects, severe combined immunodeficiency disorders, Duchenne muscular dystrophy (DMD), or adrenoleukodystrophy (ALD). In some embodiments, a method or device of the disclosure can be used to quantify bilirubin from a new born's urine for the early detection of jaundice. A method or device of the disclosure can quantify thyroxin (T4), thyrotropin (TSH), or a combination of T4 and TSH to screen for congenital hypothyroidism. A method or device of the disclosure can quantify 17α-hydroxyprogesterone (17α-OHP) to screen for congenital adrenal hyperplasia.

c. Medication Adherence Status

A method or device of the disclosure can be used to quantitatively measure analytes to determine the health status of a subject, wherein the health status is a medication adherence status. For example, a method or device of the disclosure can be used to determine the medication adherence of a subject with hypertension, hypotension, antipsychotics, tuberculosis, and diabetes, or a subject on opioids.

d. Cancer

The devices and methods herein can be used to detect, screen, diagnose, monitor cancer in a subject. Cancer can be monitored, diagnosed, detected, screened, or identified using a lateral flow strip having antibodies directed to any one or more of the analytes. Exemplary types of cancer include, but are not limited to, carcinomas (malignant tumors derived from epithelial cells such as, for example, common forms of breast, prostate, lung and colon cancer), sarcomas (malignant tumors derived from connective tissue or mesenchymal cells), lymphomas (malignancies derived from hematopoietic cells), leukemias (malignancies derived from hematopoietic cells), germ cell tumors (i.e., tumors derived from totipotent cells), blastic tumors (a typically malignant tumor which resembles an immature or embryonic tissue). Tissues that can be cancerous include, but are not limited to, neural tissue, blood forming tissue, breast, skin, bone, prostate, ovaries, uterus, cervix, liver, lung, brain, larynx, gallbladder, pancreas, rectum, parathyroid, thyroid, adrenal gland, immune system, head and neck, colon, stomach, bronchi, and/or kidneys.

A device or method of the disclosure can be used to quantify the amount of beta-2-microglobulin (B2M) in a subject to detect, screen, diagnose, or monitor the progression of multiple myeloma, chronic lymphocytic leukemia, or a lymphoma. A device or method of the disclosure can also be used to quantify the amount of hCG in a subject to detect, screen, diagnose, or monitor the progression of choriocarcinomas, germ cell tumors, or molar pregnancies. Further, a device or method of the disclosure can be used to quantify the amount of calcitonin in a subject to detect, screen, diagnose, or monitor the progression of medullary thyroid cancer. A device or method of the disclosure can also be used to quantify the amount of fibrin or fibrinogen in a subject to detect, screen, diagnose, or monitor the progression of bladder cancer.

e. Immune or Inflammatory Disorder

A subject's health status can be an immune or inflammatory disorder. For example, an autoimmune disease can be detected by quantifying the amount of chromatin, dsDNA, RNP, Sm, and Sm/RNP antibodies; Jo-1, Scl-70, SS-A, and SS-B antibodies; or centromere B and ribosomal P antibodies. Immune and inflammatory disorders include, but are not limited to, autoimmune disorders, systemic lupus erythematosus, rheumatoid arthritis, autoimmune vasculitis, celiac disease, autoimmune thyroiditis, transfusion reactions, drug-induced lupus, diabetes mellitus, Type I diabetes, Type II diabetes, juvenile onset diabetes, juvenile rheumatoid arthritis, psoriatic arthritis, multiple sclerosis, immunodeficiency, allergies, asthma, psoriasis, atopic dermatitis, allergic contact dermatitis, amyotrophic lateral sclerosis, chemotherapy-induced injury, graft-vs-host diseases, bone marrow transplant rejection, ankylosing spondylitis, atopic eczema, pemphigus, Behcet's disease, myasthenia gravis, glomerulonephritis, allergic retinitis, subacute cutaneous lupus erythematosus, cutaneous lupus erythematosus, Sjogren's syndrome, autoimmune nephritis, autoimmune vasculitis, autoimmune hepatitis, autoimmune carditis, autoimmune encephalitis, autoimmune mediated hematological diseases, scleroderma, Grave's disease (GD), myasthenia gravis, multiple sclerosis (MS), ankylosing spondylitis, transplant rejection, rheumatic/autoimmune diseases, myositis, dermatomyositis, autoimmune vasculitis, idiopathic thrombocytopenic purpura, Crohn's disease, osteoarthritis, juvenile chronic arthritis, Guillain-Barre syndrome, inflammatory bowel disease, gluten-sensitive enteropathy, allergic rhinitis, atopic dermatitis, food hypersensitivity, idiopathic pulmonary fibrosis, and ulcerative colitis. In some embodiments, a device, system, or method of the disclosure can be used to detect, screen, diagnose, or monitor the progression of polycystic ovarian syndrome (PCOS) or endometriosis.

f. Neurological Conditions

The devices, methods, and systems herein can be used to monitor, diagnose, detect, screen or identify any one or more neurological conditions of a subject. A neurological disorder can be detected by quantifying the amount of any one or more of the following analytes: angiotensinogen (AGT), contactin-1, fetuin A, kallikrein-6, osteopontin (OPN), soluble superoxide dismutase 1 (SOD1), or soluble superoxide dismutase 2 (SOD2). Neurological conditions can be monitored, diagnosed, detected, screened, or identified using a lateral flow strip having antibodies directed to any one or more of the analytes. Examples of neurological conditions include, but are not limited to, encephalitis, epilepsy, hydrocephalus, thalamic diseases, meningitis, myelitis, movement disorders, essential tremor, Alzheimer's disease (early onset), Alzheimer's disease (late onset), Huntington's disease, Parkinson's disease, Parkinson syndromes, dementia, Lewy body disease, Creutzfeldt-Jakob disease, amyotrophic lateral sclerosis (ALS), cerebral palsy (CP), memory disorders, and movement disorders. In some embodiments, a device, system, or method of the disclosure can be used to quantify the amount of amyloid beta protein to detect, screen, diagnose, or monitor the progression Alzheimer's disease.

g. Infectious Disease

Any of the devices, methods, and systems herein can be used to further detect, screen, diagnose or analyze status of a subject's infectious disease, e.g., by quantifying infectious pathogens such as bacteria or viruses. An infectious disease can be monitored, diagnosed, detected, screened, or identified using a lateral flow strip having antibodies directed to any one or more of the analytes. Examples of infectious diseases include, but are not limited to, bacterial infections, viral infections, fungal infections, protozoan infections, and parasitic infections. Particular infectious diseases include hepatitis (e.g., hepatitis A, B, C, D, and E), herpes, influenza, human papillomavirus (HPV) infection, HIV infection, AIDS, anthrax, pneumonia (bacterial or viral), cellulitis, human parainfluenza, the common cold, Legionellosis, cholera, Chlamydia, chicken pox, ebola, Dengue fever, giardiasis, Lyme disease, malaria, measles, mumps, rubella, pertussis, gonorrhea, staphylococcal infection, streptococcal infection, pneumococcal infection, rabies, Helicobacter pylori infection, respiratory syncitial virus infection, Rocky Mountain spotted fever, severe acute respiratory syndrome (SARS), sepsis, tuberculosis, and West Nile disease. Examples of infectious diseases also include, but are not limited to, Chlamydia trachomitis (Chlamydia), Neisseria gonorrhea (Gonorrhea), Borrelia burgdorferi (Lyme disease), Mycoplasma pneumoniae (walking pneumonia), Mycobacterium tuberculosis (tuberculosis), and Bordetella pertussis (whooping cough).

h. Other Analytes

A method or device of the disclosure can be used to quantitatively measure other analytes associated with the general health status of a subject, such as bilirubin, testosterone, acylglycines, beta-carotene, cholesterol, creatinine, fructose, glucose, glutaric acid, histamine, insulin, lactate, pyruvate, urea, uric acid, gluten, gliadin, or ketones. A method or device of the disclosure can be used to quantitatively measure acylglycines, such as ethylmalonic acid, 2-methylsuccinic acid, glutaric acid, isobutyrylglycine, n-butylglycine, 2-methylbutyrylglycine, isovalerylglycine, n-hexanoylglycine, n-octanoylglycine, 3-phenylpropionylglycine, suberylglycine, trans-cinnamoylglycine, dodecanedioic acid (12 DCA), tetradecanedioic acid (14 DCA), or hexadecanedioic acid (16 DCA).

D. Software and Network Systems a. Software, Image Analysis, and Analyte Quantification Once an analyte of interest is retained in a test area, the sensor/camera takes one or more images of the test region. The image is then processed using computer-implemented software. The software processes pixel intensities of the image in a hue, saturation, and value (HSV) or hue, saturation, and lightness (HSL) color space, or a component thereof (e.g., value or lightness). The software utilizes the processed data to quantify an analyte associated with a health status of a subject, and optionally providing a report on the health status.

Quantification of the analyte is performed using a rule-based image processing algorithm to interpret the intensity of a test line to accurately determine the quantity of an analyte in a biological sample (e.g., fertility hormones, such as LH or hCG). The analyte, particles, or particle-bound analytes can be used as an indicator. In addition to or as an alternative to a rule-based image processing algorithm, a computer vision/learning technique can be used, in particular, in combination with object detection or recognition.

Figure 4:
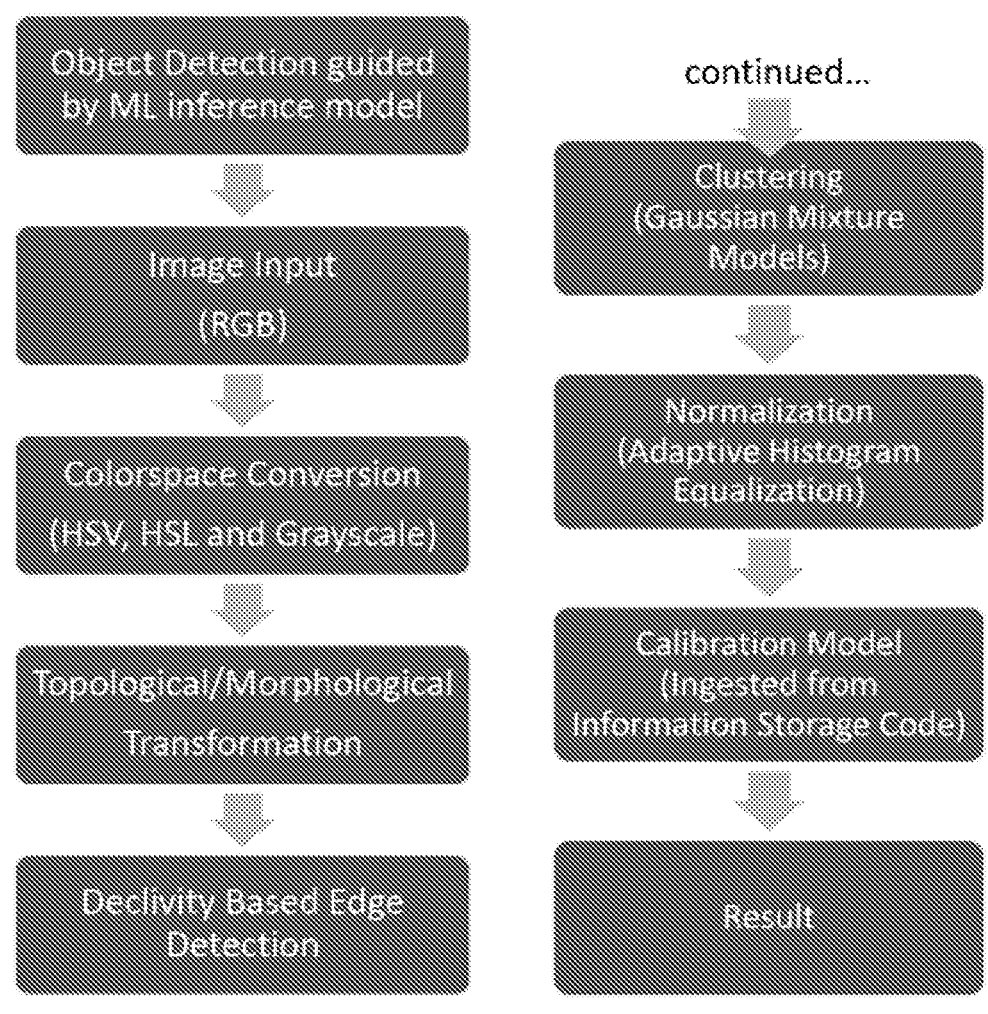
FIG. 4 illustrates the steps of processing an image to quantify an amount of a target analyte.

FIG. 4 illustrates the steps of processing an image to quantify an amount of a target analyte. Object detection is guided by a maximum-likelihood (ML) interference model. An image can be collected using RGB and subjected to: 1) a colorspace conversion (HSV, HSL, and grayscale); 2) a topological/morphological transformation; 3) declivity-based edge detection; 4) clustering using Gaussian mixture models; 5) normalization using adaptive histogram equalization; and 6) calibration using an information storage code (also used as an orientation element for the device).

A rule-based image processing algorithm that first identifies a region of interest can be used to process the image. Image processing can then capture lines of varying intensities. The color components of an image can be isolated into a single channel, and finer adjustments can be made in contrast and intensity. The hue, saturation, and value (HSV) color space can be utilized to analyze the intensity of an image. The hue, saturation, and lightness (HSL) color space can be utilized to analyze the intensity of an image. Pixel intensities of an image can be processed in the value channel. An image can be stored prior to analysis, and/or analyzed in real time without storing the image prior to analysis.

Image processing can comprise processing pixel intensities over a vector, for example, a vector spanning a control area and a vector spanning a test area of a lateral flow device. Image processing can also comprise comparing pixel intensities of the test area and the control area of a lateral flow device. The comparing can comprise normalizing pixel intensities between the test area and the control area, thereby quantifying the analyte.

The present disclosure also includes a computer-implemented system comprising a digital processing device comprising at least one processor, an operating system configured to perform executable instructions, a memory, and a computer program including instructions executable by the digital processing device to quantify an analyte using an image processing algorithm, the algorithm being configured to process pixel intensities of a hue, saturation, value, or lightness color space of an image of the analyte, and the analyte is indicative of an ovulation status of a subject. The image processing algorithm can be on a distributed computing network. The computer program can be on a mobile telephone, and the mobile telephone can comprise an optical sensor that can be used to capture an image. The pixel intensities can be processed in the value channel, and can comprise processing pixel intensities over a vector that is extracted from an image of at least a portion of a lateral flow device.

The image can comprise an image of a test area and a control area of the lateral flow device, the test area comprising captured analyte-bound particles and the control area comprising captured analyte-unbound particles. The processing can comprise processing pixel intensities over a vector spanning the control area and processing pixel intensities over a vector spanning the test area, and the processing can comprise comparing pixel intensities of the test area and the control area. The comparing of pixel intensities can also comprise normalizing the pixel intensities between the test area and the control area to quantify the target analyte.

Each image can be viewed as a matrix, and each pixel can be assigned an intensity level. The resulting matrix can then be deconstructed into a single vector of pixel intensities following a scan line. To reduce the number of data points, a signal can be scrubbed and condensed using a rolling mean that iterates on bin size until the signal fits a boundary model. Peaks can be isolated based on the scrubbed and condensed signal; the peaks of interest indicate the point at which a test line occurs. Peaks are observed normal to the scan line where there is a drastic reduction in signal intensity. If an area with a drastic reduction in signal intensity is identified, the boundary coordinates for a test line can be determined.

Peaks can be identified by first developing a function that fits the shape of a signal. A structure can be characterized using a polynomial spline. The spline can then be used to run peak sorting algorithms to identify peaks with the highest magnitude and greatest gradient. After a signal is thoroughly processed and represented, boundary conditions can be used to identify which peak is the most significant. The area below the curve at each qualified "valley" can be used to determine the largest peak. A Riemann integral followed by the Trapezoidal rule can be used to determine the largest peak. The total area across respective inflection points can be calculated, and the area below the curve can be subtracted out. Then, the gradient along rolling intervals of pixels can be calculated and stored in a list to scan and identify the maximum.

The centroid of the most significant peak identified presents the longitudinal and latitudinal center of a test line. The points that represent the start and stop of the gradient descent represent the height and width of the test line. Once a region of interest is identified, the results within the boundary can be analyzed.

The methods and systems of the present disclosure can use watershed image processing, which treats an image like a topographic map with the brightness of each point representing a pixel's height. Intensity histograms of variants of the image can be compared to a control using structural statistical tests such as Chi-square, intersection, and Bhattacharyya distance tests.

The methods and systems of the present disclosure can be used to quantify an analyte at a first time point and a second time point. The first time point and the second time point can be about 24 or fewer hours apart. The first time point and the second time point can be about 48 or fewer hours apart. The method or system can comprise quantifying an analyte once a day. A method or system of the present disclosure can be used to quantify an analyte once a day starting at the end of a woman's menstrual cycle to the beginning of her next menstrual cycle, for example, a period of 20 days. The method or system can comprise quantifying an analyte once a day for a period of at least 3 months, at least 4 months, at least 5 months, at least 6 months, at least 7 months, at least 8 months, at least 9 months, at least 10 months, at least 11 months, or at least 12 months. The method can comprise quantifying an analyte once a day for a period of at least 1 year, at least 2 years, at least 3 years, at least 4 years, or at least 5 years.

The method or system of the disclosure can further comprise comparing a quantity of an analyte at a first time point and at a second time point, wherein the comparing provides an indication of a change in the quantity of the analyte. For example, the first time point can be in a first ovulation period and the second time point can be in a second ovulation period. The change in the quantity of the analyte can be indicative of a change in ovulation status.

Every time a user interacts with the system and inputs additional data, the data from the interaction can be captured and stored in a backend system for further analysis. The results of the analyses can be combined with artificial intelligence (AI) algorithms, for example, to predict a woman's menstrual cycle. The fertility predictions made by the AI algorithm of the disclosure can get more accurate with each user interaction. The software and AI system of the disclosure can accurately forecast ovulation for a user.

A method or device of the disclosure can provide a report on a subject's health status based on quantification of a target analyte. In some embodiments, the report is an alert. In some embodiments, the alert is a push notification.

b. Smartphone App

The method of the disclosure can use a smartphone application to allow a subject to access lateral flow device data. For example, a woman can access data on her menstrual cycle obtained from lateral flow devices that detect LH, estradiol, and/or progesterone using her smart phone. A smartphone application can be synced to a web database. A subject can access personalized data through the smartphone application or through the web database.

The smartphone application can comprise any one or more of the following: a) selection of current fertility goals (i.e., avoid pregnancy, trying to get pregnant, or monitoring pregnancy) to personalize the app for a female's goal; b) real-time information on a subject's current cycle; c) access to previous months' data and trends; d) notifications for key points in her cycle or hormone levels dependent on her goal selection; e) user discussion forum; f) link to a blog; g) a summary report of her current cycle or cycles over a plurality of months; and h) access to a personalized fertility coach.

The smartphone app can also comprise subjective inputs from the user, such as cervical fluid (i.e., none, sticky, creamy, egg white, watery), indication of peak day, sex (i.e., protected, unprotected, withdrawal, insemination), menstruation (i.e., light, medium, heavy, spotting), exercise, mood or emotions, body temperature, pain (e.g., cramps, headache, tender breasts), sleep (e.g., 0-3 hours, 3-6 hours, 6-9 hours, or 9 hours or more), weight, energy level (e.g., high, low, exhausted), cravings (e.g., sweet, salty, carbs, chocolate), digestion (e.g., great, bloated, nauseated, gassy), skin (e.g., good, oily, dry, acne), or party (e.g., drinks cigarettes, hangover).

c. Computer Systems

The present disclosure describes non-transitory computer-readable storage media encoded with a computer program including instructions executable by a processor to quantify an analyte, wherein the instructions process pixel intensities of a hue, saturation, value, or lightness color space of an image of an analyte, wherein the analyte is indicative of an ovulation status of a subject. The processing can take place on a distributed computing network. The computer program can be installed on a mobile telephone, and the mobile telephone can comprise an optical sensor.

The optical sensor can be used to capture an image, and pixel intensities of the image can be processed in the value channel. The processing can comprise processing pixel intensities over a vector that is extracted from an image of at least a portion of a lateral flow device. The image can comprise an image of a test area and a control area of the lateral flow device, wherein the test area comprises captured analyte-bound particles and the control area comprises captured analyte-unbound particles. The processing can comprise processing pixel intensities over a vector spanning the control area and processing pixel intensities over a vector spanning the test area. The comparing can also comprise normalizing the pixel intensities between the test area and the control area, thereby quantifying the analyte.

The non-transitory computer-readable storage media can comprise quantifying the analyte at a first time point and at a second time point. For example, the first time point can be in a first ovulation period and the second time point can be in a second ovulation period. The non-transitory computer-readable storage media can further comprise comparing a quantity of the analyte at the first time point and at the second time point, wherein the comparing provides an indication of a change in the quantity of the analyte. In some embodiments, the change can be indicative of a change in ovulation status.

The image processing algorithm can be on a distributed computing network. In some embodiments, the computer program is on a mobile telephone, and the mobile telephone can comprise an optical sensor. The optical sensor can be used to capture the image, and the pixel intensities extracted from a vector of the image can be processed in the value channel. The image can be an image of at least a portion of the lateral flow device. The image can comprise an image of a test area and a control area of the lateral flow device, wherein the test area comprises captured analyte-bound particles and the control area comprises captured analyte-unbound particles.

The processing can comprise processing pixel intensities over a vector spanning the control area and processing pixel intensities over a vector spanning the test area. The processing can also comprise comparing pixel intensities of the test area and the control area. The comparing can comprise normalizing the pixel intensities between the test area and the control area, thereby quantifying the analyte. The computer-implemented system can comprise the quantifying the analyte at a first time point and at a second time point.

Figure 5:
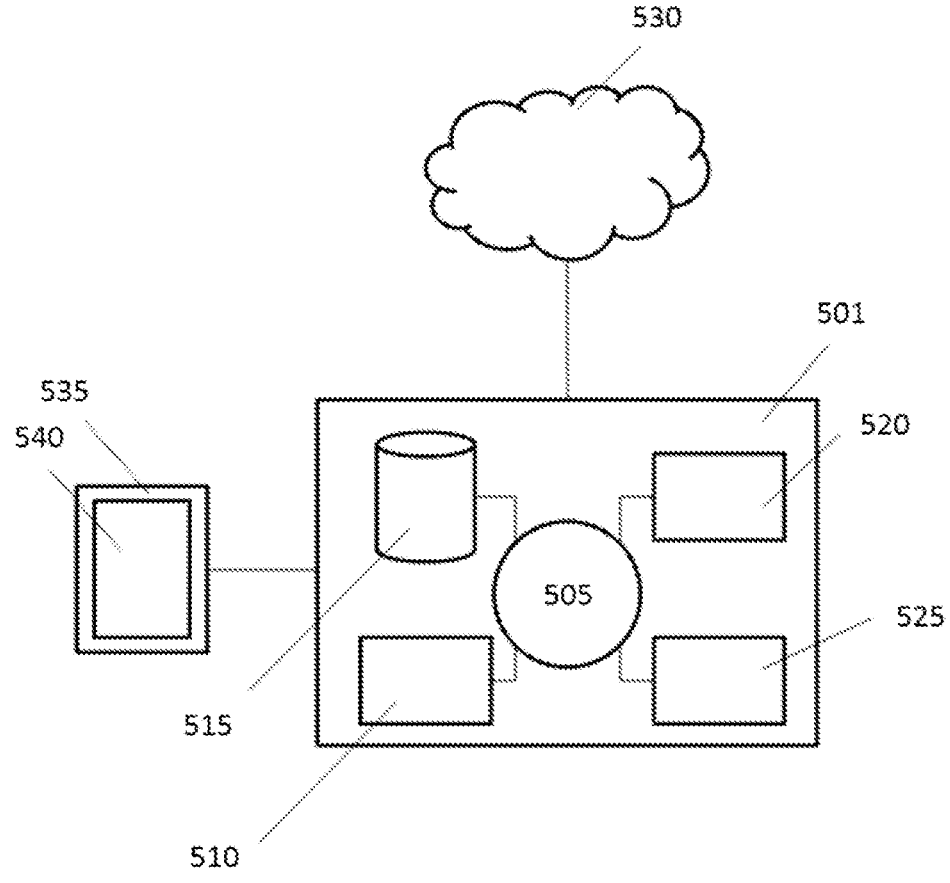
FIG. 5 shows an image of the orientation element of the lateral flow device.

The present disclosure provides computer systems that are programmed to implement methods of the disclosure. FIG. 5 shows a computer system 501 that is programmed or otherwise configured to process and/or assay a sample. The computer system 501 can regulate various aspects of sample processing and assaying of the present disclosure, such as, for example, activation of a valve or pump to transfer a reagent or sample from one chamber to another or application of heat to a sample (e.g., during an amplification reaction). The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which can enable devices coupled to the computer system 501 to behave as a client or a server.

The CPU 505 can execute a sequence of machine-readable instructions, which can be embodied in a program or software. The instructions can be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other tele-communication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Thus, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electro-magnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 501 can include or be in commu-nication with an electronic display 535 that comprises a user interface (UI) 540 for providing, for example, a current stage of processing or assaying of a sample (e.g., a particular step, such as a lysis step, that is being performed). Examples of UI's include, without limitation, a graphical user interface (GUI) and web-based user interface.

Methods and systems of the present disclosure can be implemented by way of one or more algorithms. An algo-rithm can be implemented by way of software upon execu-tion by the central processing unit 505.

E. Method of Manufacturing

The present disclosure provides methods of manufactur-ing a lateral flow device described herein. Lateral flow test strips comprising 1) a sample pad for sample application of a sample; 2) a conjugate pad containing dried colored particles; 3) a membrane striped with a test and control line; and 4) a wick pad can be inspected and assembled into a lateral flow device. The present disclosure also describes a method of manufacturing a lateral flow device, which com-prises an orientation element that is used to normalize the control area of a batch of lateral flow devices.

The lateral flow test strips are rigorously analyzed for consistency. Each batch of the lateral flow test strips can be scanned using high resolution imaging equipment. A batch of the lateral flow test strips can be a batch of 50, 100, 250, 500, 750, 1000, 1500, 2000, 2500, 3000, 3500, 4000, 4500, or 5000 test strips. Each tested batch can be given a "Batch ID".

The Batch ID number may be stored in the non-transitory computer-readable storage media. Calibration indices for the signal intensities can also be stored as quality control and calibration for later interpretation by a rule-based algorithm. During the quality control process, batches can be hand populated with known analyte concentrations. The signal intensities and the respective parameters can include, but are not limited to, color hue thresholds, sample flow rate, and a concentration-to-intensity statistical model, which will be analyzed and stored as reference for later comparison.

Figure 6:
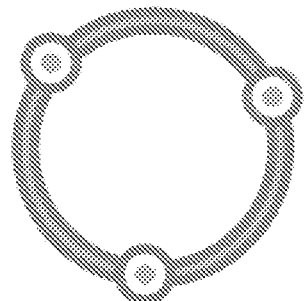
FIG. 6 shows a computer system that is programmed or otherwise configured to process and/or assay a sample.

The device of the disclosure can also be provided with an orientation element, which is printed in high resolution on a transparent film. The film is applied to the lateral flow device, and acts as a sample protectant and window for the lateral flow device. The orientation element can be unique to each batch of lateral flow test strips or each individual lateral flow test strip. FIG. 6 shows an image of the orientation element of the lateral flow device.

F. Storage System

Figure 7:
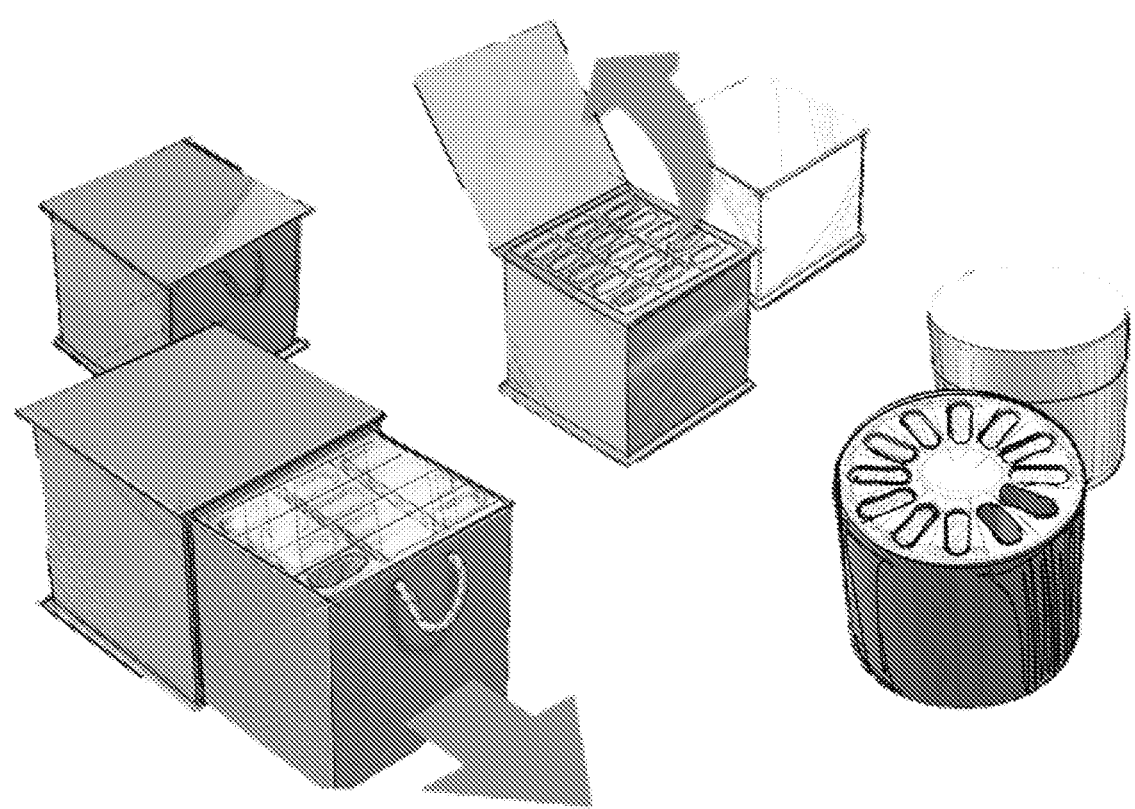
FIG. 7 shows drawings of storage systems of the disclosure.

A storage system can be used to store a disposable cartridge of the disclosure. The storage system for the disposable cartridge can provide an environment that is safe for transport as well as preserving the shelf-life of the embedded chemistry. Each cartridge can be stored in an individual well and can include a desiccant material to aid in the removal of ambient moisture. Desiccant material can be, for example at the bottom of each individual well or in a central area. Each well can be sealed with a seal such as a sticker type seal or perforated seal. In some embodiments, the seal can prevent the cartridge from being exposed to environmental conditions that could decrease shelf life. Non-limiting examples of environmental conditions that can decrease shelf life include humidity, moisture, chemical contaminant, and physical particulate matter. In some embodiments, the seal for each well can be opened with a single hand. Individual wells can be one-time use or can be reusable. In some embodiments, the opening of the well is of sufficient size to accept a handle type attachment for directly connecting to the cartridge. A drawing of example cartridges of the disclosure is shown in FIG. 7.

In some embodiments, a storage system of the disclosure can be about 0.5 inches, 1 inch, 1.5 inches, or 2 inches in length by about 1 inch. About 2 inches, about 3 inches, about 4 inches, about 5 inches, about 6 inches, about seven inches, or greater than 7 inches in length. In some embodiments a storage system of the disclosure can be of equal length and width.

A storage system of the disclosure can hold multiple cartridges or a single cartridge. In some embodiments a storage system of the disclosure has the capacity for 1, 2, 3, 4, 5, 6, 7, 8, 9, 10 or more than 10 cartridges.

A storage system of the disclosure can be any shape such as, for example cylindrical or rectangular. In some embodiments the shape of the storage system is determined by the length of storage. For example, if it is desired that cartridges be easily accessible the storage system can be rectangular and have an easy open lid; while if the storage system is for long-term storage the system can be cylindrical and have a screw on lid. A storage system of the disclosure can store a cartridge for about 1 month, about 2 month, about 3 month, about 4 months, about 5 months, about 6 months, about 7 months, about 8 months, about 9 months, about 10 months, about 11 months, about 1 year, about 2 years, about 3 years, about 4 years, about 5 years, or about more than 5 years.

G. Machine Learning Algorithm

Methods and systems of the present disclosure can be implemented by way of one or more algorithms (e.g., machine learning algorithms). An example of a machine learning algorithm can be Elbattah, Mahmoud, and Molloy, Owen, "Clustering-Aided Approach for Predicting Patient Outcomes with Application to Elderly Healthcare in Ireland," The AAAI-17 Joint Workshop on Health Intelligence WS-17-09, 533-541 (2017), and can be incorporated in the methods and systems of the present disclosure. In some embodiments, a machine learning algorithm described herein can take in as an input: height, weight, age, gender, pregnancy status, length of current menstrual cycle, average length of menstrual cycle, or estimated day of ovulation as a function of, day of last period and length of cycle, length of current period, length of average period, number of peak hormone level days, average number of peak hormone days, number of cycles collected, number of days of intercourse, period intensity, cervical fluid description, pain, cravings, digestion, hair, skin, stool, body temperature, exercise, sleep, sex drive, mental state, mood, motivation, productivity, social behavior, partying, energy, birth control use, medication use, hormone therapy use, or ailments.

In some embodiments, the machine learning algorithm can provide an output. Non-limiting examples of outputs a machine learning algorithm of the disclosure can provide include classification of health status*, daily action plans, nutritional recommendations, supplement recommendations, additional diagnostic recommendations, and coaching recommendations.

A machine learning algorithm disclosed herein can utilize sub-algorithms. Sub-algorithms can include, for example, supervised or unsupervised algorithms. Non-limiting examples of unsupervised algorithms include unsupervised clustering and preprocessing algorithms such as k-means clustering, hierarchical clustering, principal component analysis and gaussian mixture models, artificial neural networks and convolutional neural networks. Non-limiting examples of supervised algorithms include supervised classification algorithms such as to support vector machines, naïve Bayes, linear discriminant analysis, decision trees and random forest and artificial neural networks and convolutional neural networks.

Figure 8:
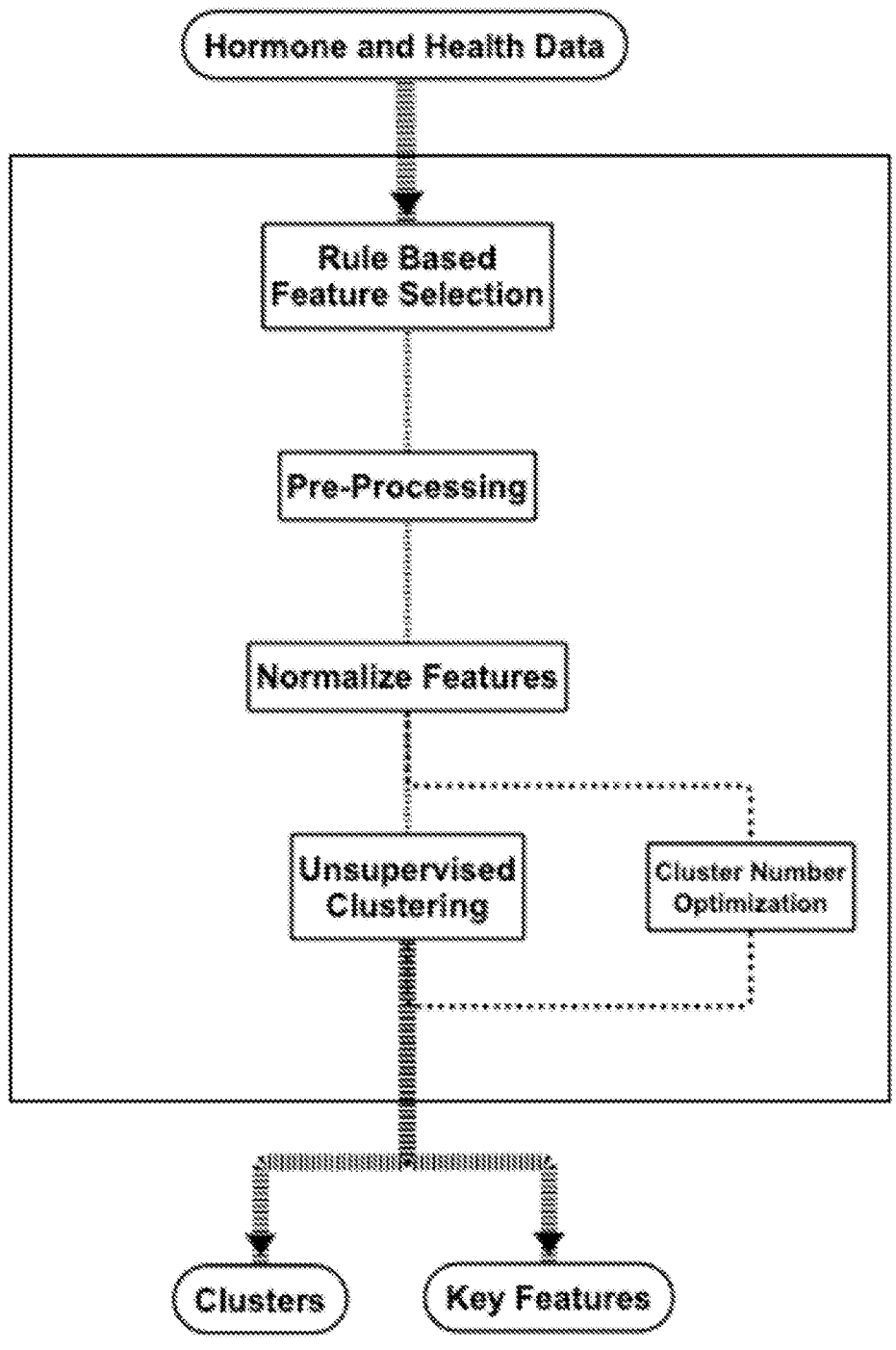
FIG. 8 shows an overview of an unsupervised clustering algorithm.

A machine learning algorithm of the disclosure can utilize an unsupervised clustering algorithm. A clustering algorithm can be an unsupervised learning algorithm that uses a combination of rule-based programming vector quantization to cluster users of similar attributes. Non-liming examples of said attributes can include; age, height, weight, hormone data, length of cycle, estimated day of ovulation, etc. Features can be cleaned by a method for taking multi-modal data and numerically mapping it to a format useful for these types of learning algorithms. Data is subsequently parsed and cleaned, removing missing values. Input data can be normalized using a scale of 0-1. In some embodiments an unsupervised clustering model can utilize k-means clustering or a gaussian mixture model. The output of an unsupervised clustering model is a vector that represents the matrix of features as defined cluster classes. These clusters can represent a health status or ailment that is the dependent variable based on the interpretation of the algorithm of said input, independent variables. An additional output is the set of N features that represent most of the variation in defining clustering and therefore are the most important. Non-limiting examples of this are age, height, race, and weight. An overview of an unsupervised clustering algorithm described herein can be found in FIG. 8.

A machine learning algorithm of the disclosure can be trained using, for example, supervised learning methods, unsupervised learning methods, or a combination of supervised and unsupervised learning methods. During unsupervised clustering a machine learning algorithm disclosed herein can cluster data that has not been previously labelled into clusters based on inherent commonalities in the input features. All of the input features associated to a single object, such as a patient or user, can be placed in a hyper-dimensional point space. Using vector quantization, subsequent objects can be placed in this point space at a distance dependent on how similar the input features are. If the objects features are similar to the one before it, it will be closer, if they a more different it will reside farther away. The result is clusters of objects based on similarities in their input features. The number of clusters can be predetermined as input to the machine learning arguments.

In regard to a particular health status, women with a similar longitudinal hormone profile, cycle length, age, height, weight, etc. would reside in the same category.

In some embodiments, the unsupervised learning model is retrained in a continuous way as new data is injected into the database. In some embodiments, the clusters determined by the unsupervised learning model become the labels or annotations for use in the supervised learning model.

Figure 9:
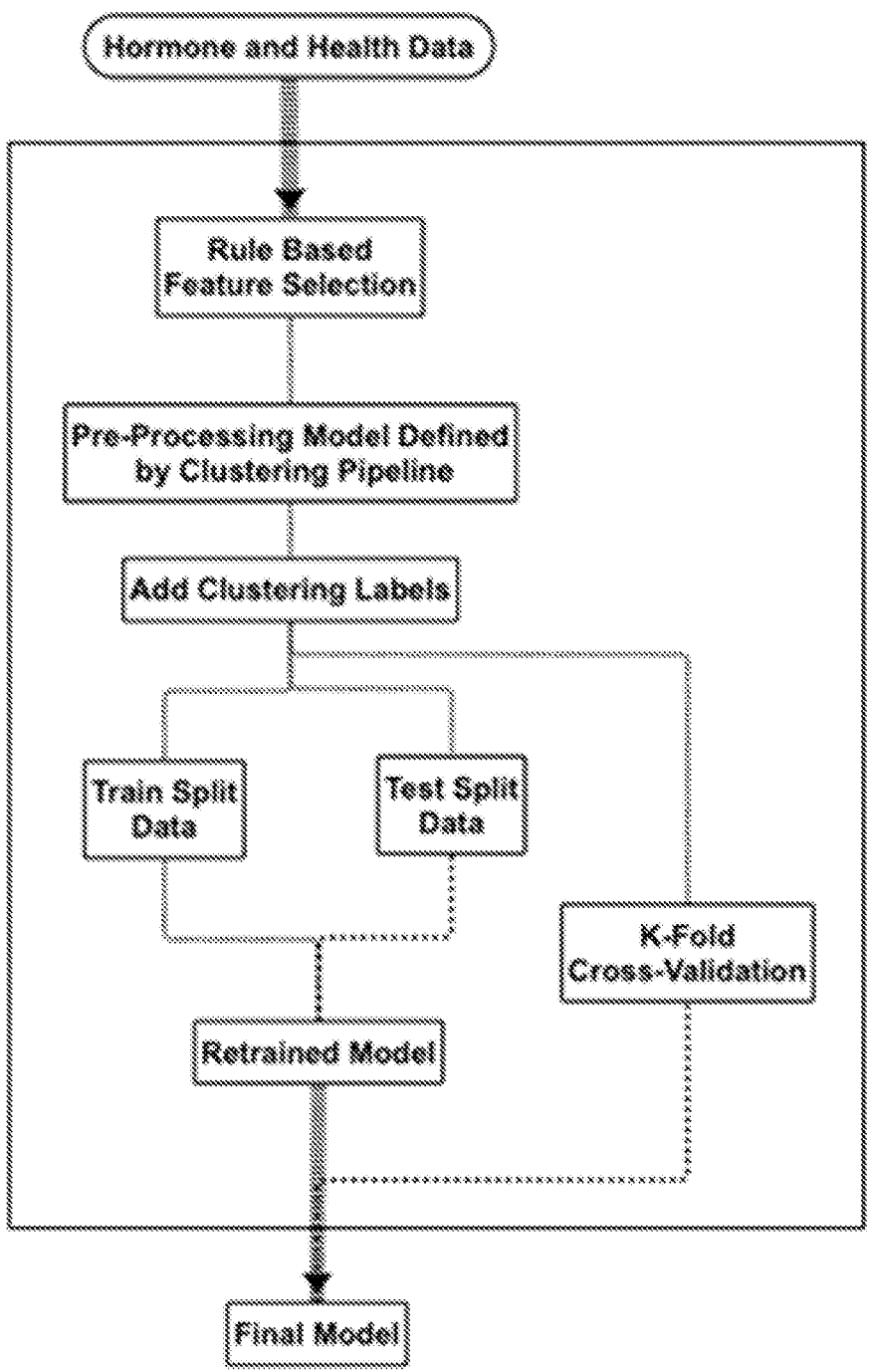
FIG. 9 shows a schematic of a supervised classification inference model.

A machine learning algorithm of the disclosure can utilize a supervised classification inference model, a schematic of which is shown in FIG. 9. A supervised classification inference model can use a probabilistic Bayesian model architecture. The model takes features as input and classifies them into 1 of N classes. Classes can be generic labels or could represent a health status. The classes used for the training step can be defined by the unsupervised learning approach specified in clustering step. In some embodiments, the training processes utilizes a train-test split set and k-fold cross validation. In some embodiments, a supervised classification inference model can be used as inference to classify users/patients given a set of hormone and health data.

A supervised classification learning model described herein can be used for future prediction or inference of new users or patients into the clusters defined by the unsupervised learning model. The model can be trained, and its performance measured, by splitting the data into test and training sets. The model can map a set of inputs to outputs by learning on the train set of input and output pairs. The performance of the algorithm can be determined by using the inference model to predict that labels of the test set and comparing it against the known truth. In regard to a health status, the classification inference model can take in an unknown data object with inputs as specified above and predict the health status. A supervised learning model described herein can be retrained in a continuous way as new data is injected into the database.

A machine learning algorithm of the disclosure can start with, for example, a k-means clustering model or a naïve Bayes supervised classification model. In some embodiments an open-source data set of women's menstrual cycles can be used to train a machine learning algorithm disclosed herein. In some embodiments, simulated data or a combination of real and simulated data can be used to train a machine learning algorithm disclosed herein.

Figure 10:
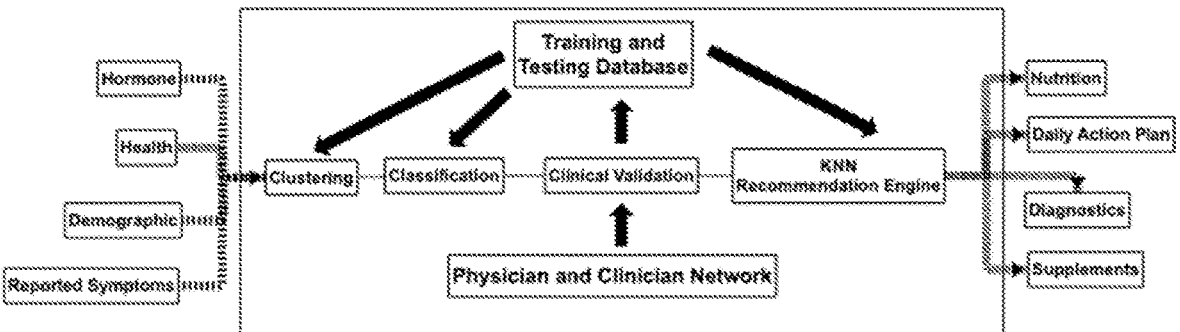
FIG. 10 shows a schematic of a machine learning algorithm.

A schematic of a machine learning algorithm of the disclosure is shown in FIG. 10. Data can stream into a machine learning algorithm of the disclosure via, for example, mobile applications, web portals, and websites. Data can cumulatively support a database. In some embodiments, a machine learning recommendation system will use a k-nearest neighbors algorithm to match personalized health attributes to interventional recommendations. In some embodiments, machine learning clustering, inference and recommendation models will continuously train, utilizing new data. In some embodiments, a machine learning algorithm disclosed herein can provide reports on health status. In some embodiments reports on health status provided by a machine learning algorithm are validated by a licensed physician. In some embodiments, licensed physicians continuously annotate and validate learning models and data resources of a machine learning algorithm.

In some embodiments, the performance of a classification model disclosed herein can be represented by a confusion matrix. A confusion matrix is meant to show the percent accuracy in a model's ability to identify each data object in the test set. The accuracy is determined by comparing the total number of objects processed by the number of objects correctly identified per each class. More broadly the performance of a classification algorithm disclosed herein can be determined by its accuracy, precision, recall, and F1 scores. Accuracy is the ratio of correctly predicted observations to the total observations. Precision is the ratio of correctly predicted positive observations to the total predicted positive observations. Recall or sensitivity is the ratio of correctly predicted positive observations to all observations in the actual class. F1 Score is the weighted average of precision and recall.

A computer-implemented method may comprise processing pixel intensities in a hue, saturation, value, or lightness color space of an image of an indicator associated with a health status of a subject, thereby quantifying the indicator, and providing a report on the health status.

The pixel intensities can be processed in the value channel. The processing can comprises processing pixel intensities over a vector. The indicator can be an analyte. The indicator can be a particle. The indicator can be a particle-bound analyte. The image can be an image of at least a portion of a lateral flow device. The image can comprise an image of a test area and a control area of the lateral flow device. The test area can comprise captured analyte-bound particles, and the control area comprises captured analyte-unbound particles. The processing can comprise processing pixel intensities over a vector spanning the control area and processing pixel intensities over a vector spanning the test area. The processing can comprise comparing pixel intensities of the test area and the control area. The comparing can comprise normalizing the pixel intensities between the test area and the control area, thereby quantifying the analyte. The processing can occur in real-time. The computer-implemented method can further comprise a topological and morphological transformation. The computer-implemented method can comprise quantifying the analyte at a first time point and at a second time point. The first time point and the second time point are about 24 or fewer hours apart. The first time point and the second time point are about 48 or fewer hours apart.

The computer-implemented method can comprise quantifying once a day. The computer-implemented method can comprise quantifying once a day for a 20-day period. The quantity of the analyte can be compared at the first time point and at the second time point, wherein the comparing provides an indication of a change in the quantity of the analyte. The first time point may be in a first ovulation period and the second time point is in a second ovulation period. The change can be indicative of a change in ovulation status. The lateral flow device further comprises an orientation element, wherein the processing comprises using the orientation element to locate the test area and the control area. The test area and control area can be within the orientation element. The orientation element can comprise information on a batch number.

The orientation element can be used to normalize the control area of the lateral flow device. The particle can be a gold particle. The gold particle can be a colloidal gold particle. The colloidal gold particle can be bound to a first analyte capture agent. The first analyte capture agent can be an antibody that specifically binds to the analyte. The test area can comprise a second analyte capture agent. The second analyte capture agent can be an antibody that specifically binds to the analyte. The control area can comprise a control agent that specifically binds to the first analyte capture agent. The control agent can be an antibody that specifically binds to the first analyte capture agent. Prior to the processing, the lateral flow device can be contacted with a biological sample comprising the analyte. The biological sample can be urine. The analyte can be selected from the group consisting of luteinizing hormone, progesterone, human chorionic gonadotropin, and estradiol. The analyte can be luteinizing hormone. The health status can be an ovulation status. The health status can be a newborn health status. The health status can be a medication adherence status. The health status can be a disease status. The report can be linked to a user profile. The report can be an alert.

A computer-implemented system can comprise a digital processing device comprising at least one processor, an operating system configured to perform executable instructions, a memory, and a computer program including instructions executable by the digital processing device to quantify an analyte using an image processing algorithm. The algorithm can be configured to process pixel intensities of a hue, saturation, value, or lightness color space of an image of the analyte. The analyte can be indicative of an ovulation status of a subject. The image processing algorithm can be on a distributed computing network. The computer program can be on a mobile telephone. The mobile telephone can comprise an optical sensor. The optical sensor can be used to capture the image. The pixel intensities can be processed in the value channel. Processing can comprise processing pixel intensities over a vector. Processing can occur in real-time. The computer-implemented system can further comprise a topological and morphological transformation.

The image can be an image of at least a portion of a lateral flow device. The image can comprise an image of a test area and a control area of the lateral flow device. The test area can comprise captured analyte-bound particles and the control area can comprise captured analyte-unbound particles. The processing can comprise processing pixel intensities over a vector spanning the control area and processing pixel intensities over a vector spanning the test area. The processing can comprise comparing pixel intensities of the test area and the control area. The comparing can comprise normalizing the pixel intensities between the test area and the control area, thereby quantifying the analyte. The computer-implemented system can comprise quantifying the analyte at a first time point and at a second time point. The first time point can be in a first ovulation period and the second time point is in a second ovulation period.

A quantity of the analyte can be compared at the first time point and at the second time point, wherein the comparing provides an indication of a change in the quantity of the analyte. The change can be indicative of a change in ovulation status. The lateral flow device can further comprise an orientation element. The test area and control area may be positioned within the orientation element. The processing comprises using the orientation element to locate the test area and the control area.

The orientation element can comprise information on a batch number. The orientation element can be used to normalize the control area of the lateral flow device. The particles can be gold particles. The gold particles can be colloidal gold particles. The colloidal gold particles can be bound to a first analyte capture agent. The first analyte capture agent can be an antibody that specifically binds to the analyte. The test area can comprise a second analyte capture agent. The second analyte capture agent can be an antibody that specifically binds to the analyte. The control area may comprise a control agent that specifically binds to the first analyte capture agent. The control agent can be an antibody that specifically binds to the first analyte capture agent. Prior to the processing, the lateral flow device can be contacted with a biological sample comprising the analyte. The biological sample can be urine. The analyte can be selected from the group consisting of luteinizing hormone, progesterone, human chorionic gonadotropin, and estradiol. The analyte can be luteinizing hormone.

Non-transitory computer-readable storage media encoded with a computer program can include instructions executable by a processor to quantify an analyte. The instructions can process pixel intensities of a hue, saturation, value, or lightness color space of an image of an analyte. The analyte can be indicative of an ovulation status of a subject. The processing can be on a distributed computing network. The computer program can be on a mobile telephone. The mobile telephone can comprise an optical sensor. The optical sensor can be used to capture the image.

The pixel intensities can be processed in the value channel. The processing can comprise processing pixel intensities over a vector. The image can be an image of at least a portion of a lateral flow device. The image can comprise an image of a test area and a control area of the lateral flow device. The test area can comprise captured analyte-bound particles and the control area can comprise captured analyte-unbound particles. The processing can comprise processing pixel intensities over a vector spanning the control area and processing pixel intensities over a vector spanning the test area. The processing can occur in real-time. The non-transitory computer-readable storage media can further comprise a topological and morphological transformation. The processing can comprise comparing pixel intensities of the test area and the control area. The comparing can comprises normalizing the pixel intensities between the test area and the control area, thereby quantifying the analyte. The non-transitory computer-readable storage media can comprise the quantifying the analyte at a first time point and at a second time point. The first time point can be is in a first ovulation period and the second time point can be in a second ovulation period. The non-transitory computer-readable storage media can further comprise comparing a quantity of the analyte at the first time point and at the second time point. The comparing can provide an indication of a change in the quantity of the analyte.

The change can be indicative of a change in ovulation status. The lateral flow device can further comprise an orientation element. The test area and control area can be positioned within the orientation element. The processing can comprise using the orientation element to locate the test area and the control area. The orientation element can comprise information on a batch number. The orientation element can be used to normalize the control area of the lateral flow device. The particles can be gold particles. The gold particles can be colloidal gold particles. The colloidal gold particles can be bound to a first analyte capture agent. The first analyte capture agent can be an antibody that specifically binds to the analyte. The test area can comprise a second analyte capture agent. The second analyte capture agent can be an antibody that specifically binds to the analyte. The control area can comprise a control agent that specifically binds to the first analyte capture agent. The control agent can be an antibody that specifically binds to the first analyte capture agent. Prior to the processing, lateral flow device can be contacted with a biological sample comprising the analyte. The biological sample can be urine. The analyte can selected from the group consisting of luteinizing hormone, progesterone, human chorionic gonadotropin, and estradiol. The analyte can be luteinizing hormone.

A lateral flow device can comprise particles comprising a first analyte capture agent, a test area comprising a second analyte capture agent, a control area comprising a control agent, and an orientation element. The test area and control area can be within the orientation element. The particles can be gold particles. The gold particles can be colloidal gold particles. The first analyte capture agent can be an antibody that specifically binds to the analyte. The second analyte capture agent can be an antibody that specifically binds to the analyte. The control agent can specifically bind to the first analyte capture agent. The control agent can be an antibody that specifically binds to the first analyte capture agent. Particles may be contacted with a biological sample comprising an analyte in the test area. The biological sample can be contacted with the particles under conditions that permit binding between the particles and the analyte. The particles may be contacted with the control agent in the control area, wherein the particles are contacted with the control agent under conditions that permit binding between the particles and the control agent.

A kit can comprise two or more of the lateral flow device comprising particles comprising a first analyte capture agent, a test area comprising a second analyte capture agent, a control area comprising a control agent, and an orientation element.

A system may comprise a lateral flow device. The system may comprise a computer-implemented system comprising a digital processing device comprising at least one processor, an operating system configured to perform executable instructions, a memory, and a computer program including instructions executable by the digital processing device to quantify an analyte using an image processing algorithm. The algorithm can be configured to process pixel intensities of a hue, saturation, value, or lightness color space of an image of the analyte. The analyte can be indicative of an ovulation status of a subject.

The image processing algorithm can on a distributed computing network. The computer program can be on a mobile telephone. The mobile telephone can comprise an optical sensor. The optical sensor can be used to capture the image. The pixel intensities can be processed in the value channel. The processing can comprise processing pixel intensities over a vector. The image can be an image of at least a portion of the lateral flow device. The image can comprise an image of a test area and a control area of the lateral flow device. The test area can comprise captured analyte-bound particles and the control area comprises captured analyte-unbound particles. The processing can comprise processing pixel intensities over a vector spanning the control area and processing pixel intensities over a vector spanning the test area. The processing can be in real-time. The computer-implemented system can further comprise a topological and morphological transformation.

The processing can comprise comparing pixel intensities of the test area and the control area. The comparing can comprise normalizing the pixel intensities between the test area and the control area, thereby quantifying the analyte. The computer-implemented system can comprise the quantifying the analyte at a first time point and at a second time point. The first time point can be in a first ovulation period and the second time point can be in a second ovulation period. A quantity of the analyte can be compared at the first time point and at the second time point. The comparing can provide an indication of a change in the quantity of the analyte. The change can be indicative of a change in ovulation status. The lateral flow device can comprise an orientation element.

The test area and control area can be within the orientation element. The orientation element can comprise information on a batch number. The orientation element can be used to normalize the control area of the lateral flow device. The particles can be gold particles. The gold particles can be colloidal gold particles. The colloidal gold particles can be bound to a first analyte capture agent. The first analyte capture agent can be an antibody that specifically binds to the analyte. The test area can comprise a second analyte capture agent. The second analyte capture agent can be an antibody that specifically binds to the analyte. The control area can comprise a control agent that specifically binds to the first analyte capture agent. The control agent can be an antibody that specifically binds to the first analyte capture agent.

Prior to the processing, the lateral flow device can be contacted with a biological sample comprising the analyte. The biological sample can be urine. The analyte can be selected from the group consisting of luteinizing hormone, progesterone, human chorionic gonadotropin, and estradiol. The analyte can be luteinizing hormone. The computer-implemented system can store a user profile for the subject. The computer-implemented system can further provide a report comprising providing an alert to the subject. The alert can be a push notification. The orientation element can be used to normalize the control area of a batch of the lateral flow device.

EXAMPLES

Example 1: Gold Nanoparticles 150 nm diameter gold nanoshells comprising 120 nm silica core particles coated with a 15 nm thick gold shells were prepared and tested for sensitivity. The gold nanoshells demonstrated a dramatic increase in sensitivity in lateral flow assays compared to 40 nm gold spheres.

Figure 11:
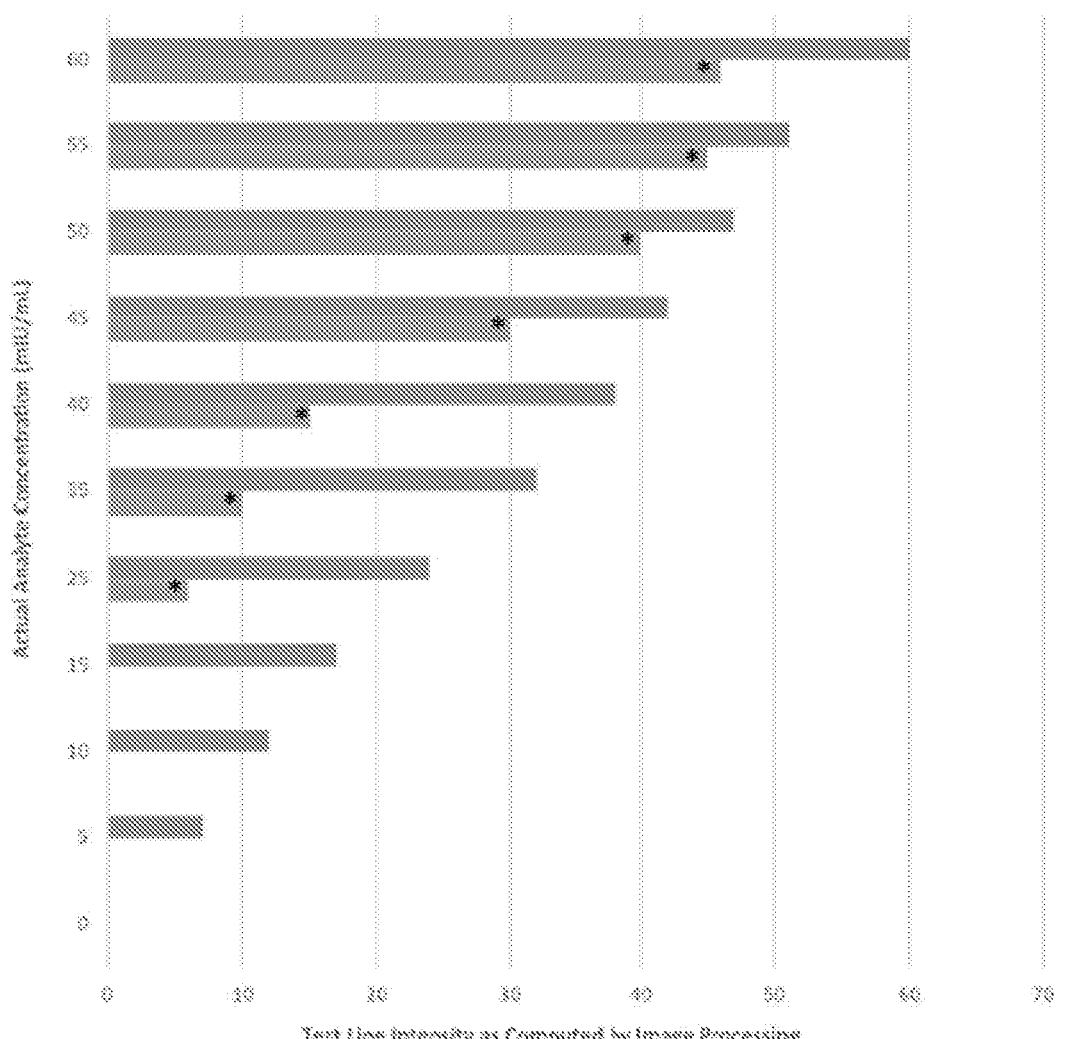
FIG. 11 compares the detection sensitivities between 40 nm colloidal gold spheres and latex microspheres.

FIG. 11 compares the detection sensitivities between 40 nm colloidal gold spheres and gold nanoshells. The bar chart indicates the sensitivity of both 40 nm colloidal gold spheres and gold nanoshells. The data show that the gold nanoparticles of the disclosure were more sensitive than 40 nm colloidal gold spheres at concentrations of 0.5 ng/mL, 1 ng/mL, 2 ng/mL, 4 ng/mL, 8 ng/mL, 16 ng/mL, and 20 ng/mL. The data also show that the gold nanoshells could detect the presence of analytes at concentrations of 0.005 ng/mL, 0.1 ng/mL, and 0.3 ng/mL, whereas the 40 nm colloidal gold spheres could not detect the presence of the analyte.

Example 2: Initial Prototype Test Strips

Prototype lateral flow strips were developed to validate image processing algorithms using colloidal gold nanoshells. The test strips were made of nitrocellulose membrane, and were 8 mm wide and 70 mm long. Each test strip was populated with a sample for about 5 minutes, and utilized goat IgG as a test. The strips were activated using sodium ethanoate as a running buffer (i.e., no hormone of interest was present) with each strip having a known intensity of the line. The tests were used to determine line intensity quantification for the purpose of developing the imaging software, and not for analyte detection. The first round of prototype strips were delivered in seven batches of 100 strips each. The individual batches represented hard printed test lines of varying intensities when exposed to the buffer solution. The dummy strips were used to test the sensitivity of the algorithm and hardware by ensuring detection of minute differences between the known intensities of the test lines.

Figure 12:
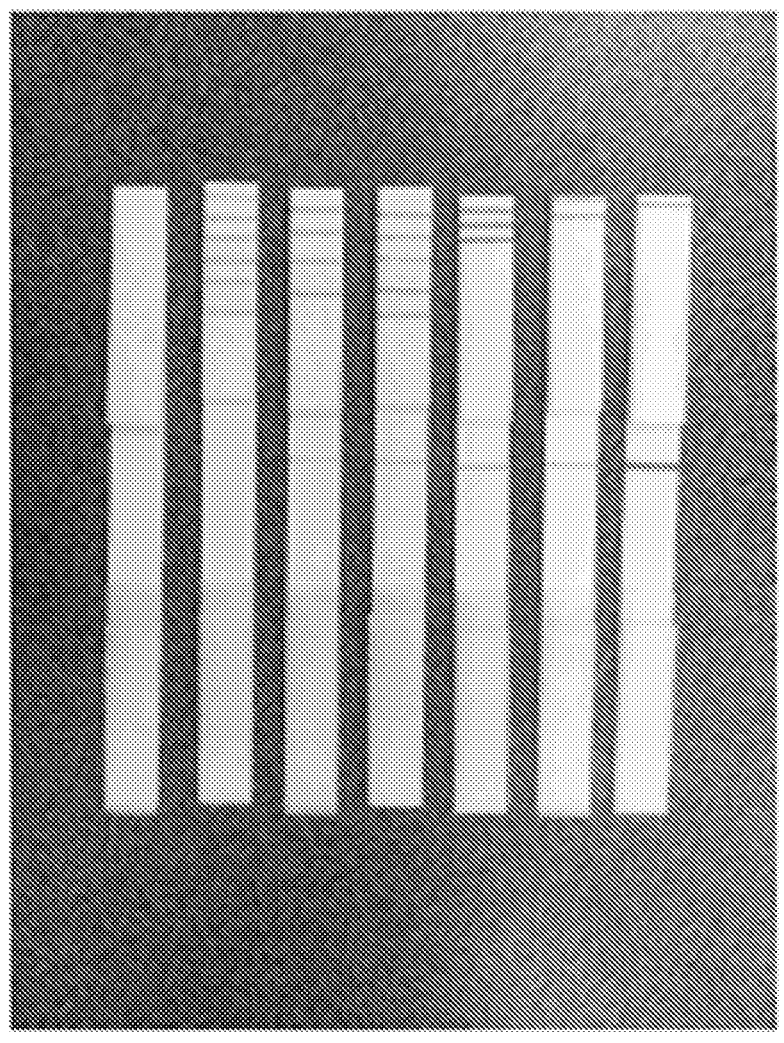
FIG. 12 shows the differences in intensities observed across various batches of lateral flow strips.

FIG. 11 compares the detection sensitivities between 40 nm colloidal gold spheres and latex microspheres. FIG. 12 shows the differences in intensities observed across various batches of dummy strips.

8 clone pairs were screened using five urine samples spiked with varying concentrations of LH. The eight clone pairs were A/2, C/4, D/4, A/5, 2/D, 6/D, 5/H, and 6/H, where the letters represented anti-LH antibodies and the numbers represented anti-alpha subunit antibodies. All eight pairs were run in triplicate. The urine samples had concentrations of 0 mIU/mL, 5 mIU/mL, 15 mIU/mL, and 40 mIU/mL of LH. For some clone pairs, stark differences were observed between urine samples. Some paired clones showed sample-dependent gold conjugate instability, while others showed varying degrees of non-specific binding. Five pairs were found that showed generally good performance characteristics for all five urine samples.

Figure 13:
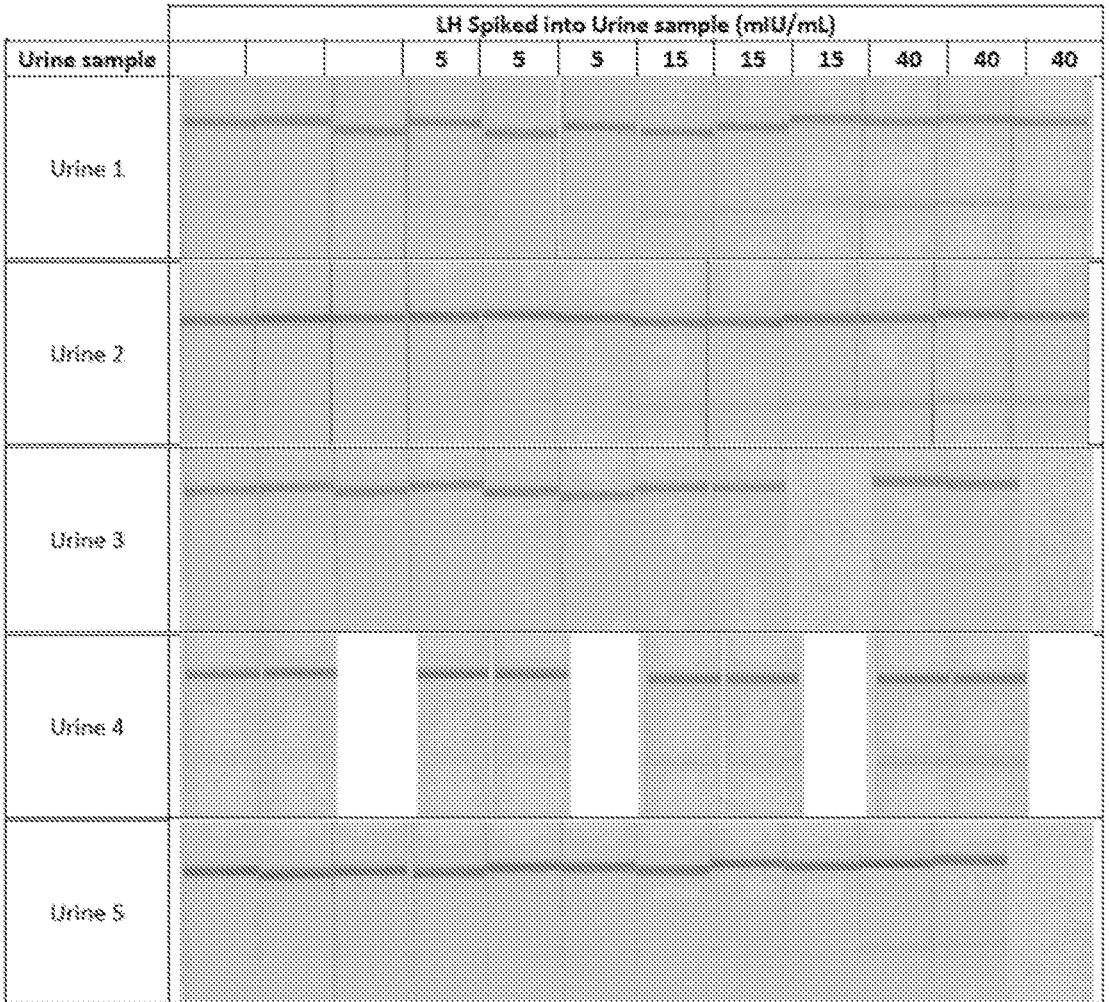
FIG. 13 shows detection of luteinizing hormone (LH) on lateral flow strips contacted with five different urine samples into which with varying amounts of LH were spiked. The lateral flow strips used clone pair A/2.

Clone pair A/2: Urine 2 showed higher levels of binding for 0 mIU/mL than the other urine samples. FIG. 13 shows the results obtained from clone pair A/2.

Figure 14:
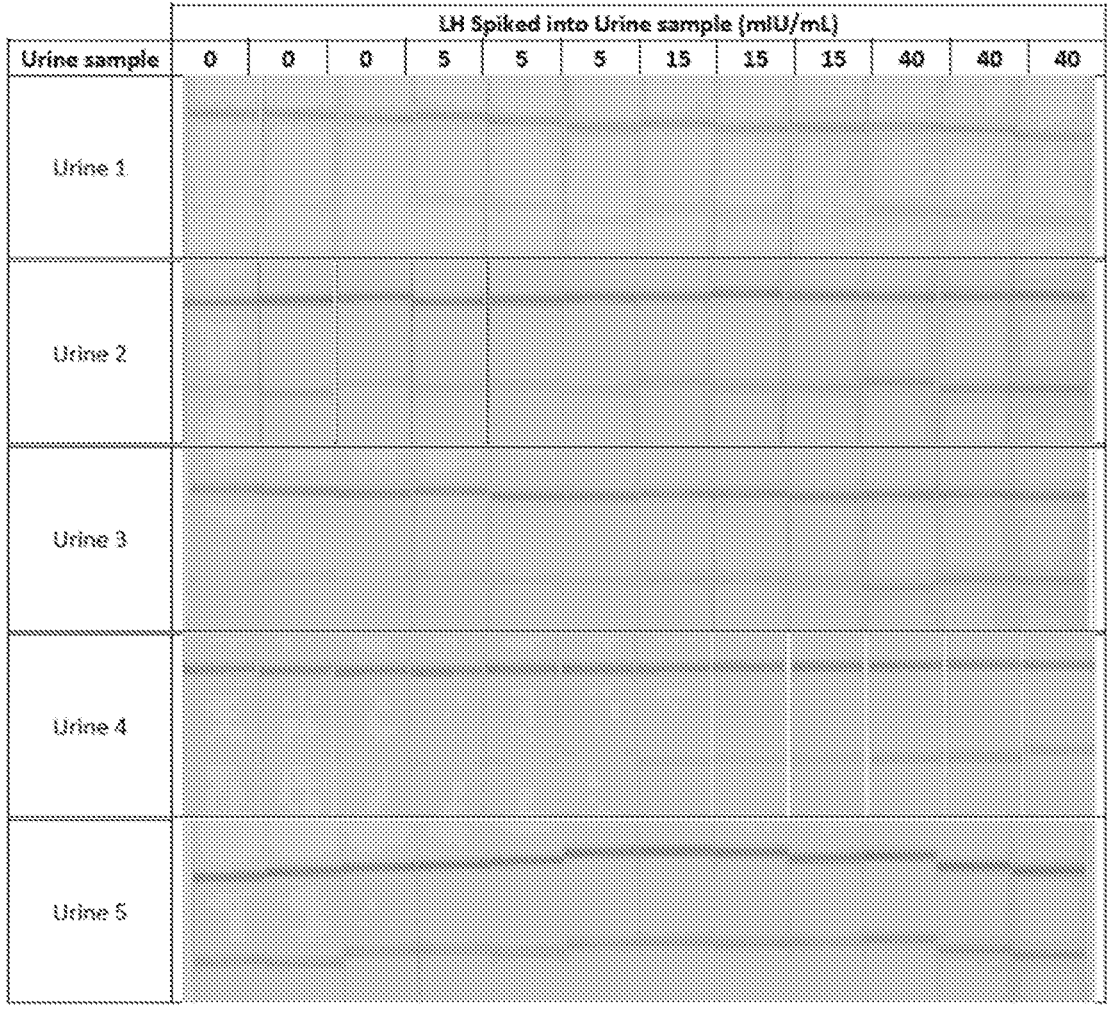
FIG. 14 shows detection of luteinizing hormone (LH) on lateral flow strips contacted with five different urine samples into which with varying amounts of LH were spiked. The lateral flow strips used pair D/4.

Clone pair D/4: Urine 2 showed higher levels of non-specific binding. The second strip run with 0 mIU/mL urine was accidentally run with double the amount of the conjugate, which resulted in darker test and control lines. Urine 5 showed very high levels of binding even with the urine sample that had 0 mIU/mL of LH. FIG. 14 shows the results obtained from clone pair D/4.

Figure 15:
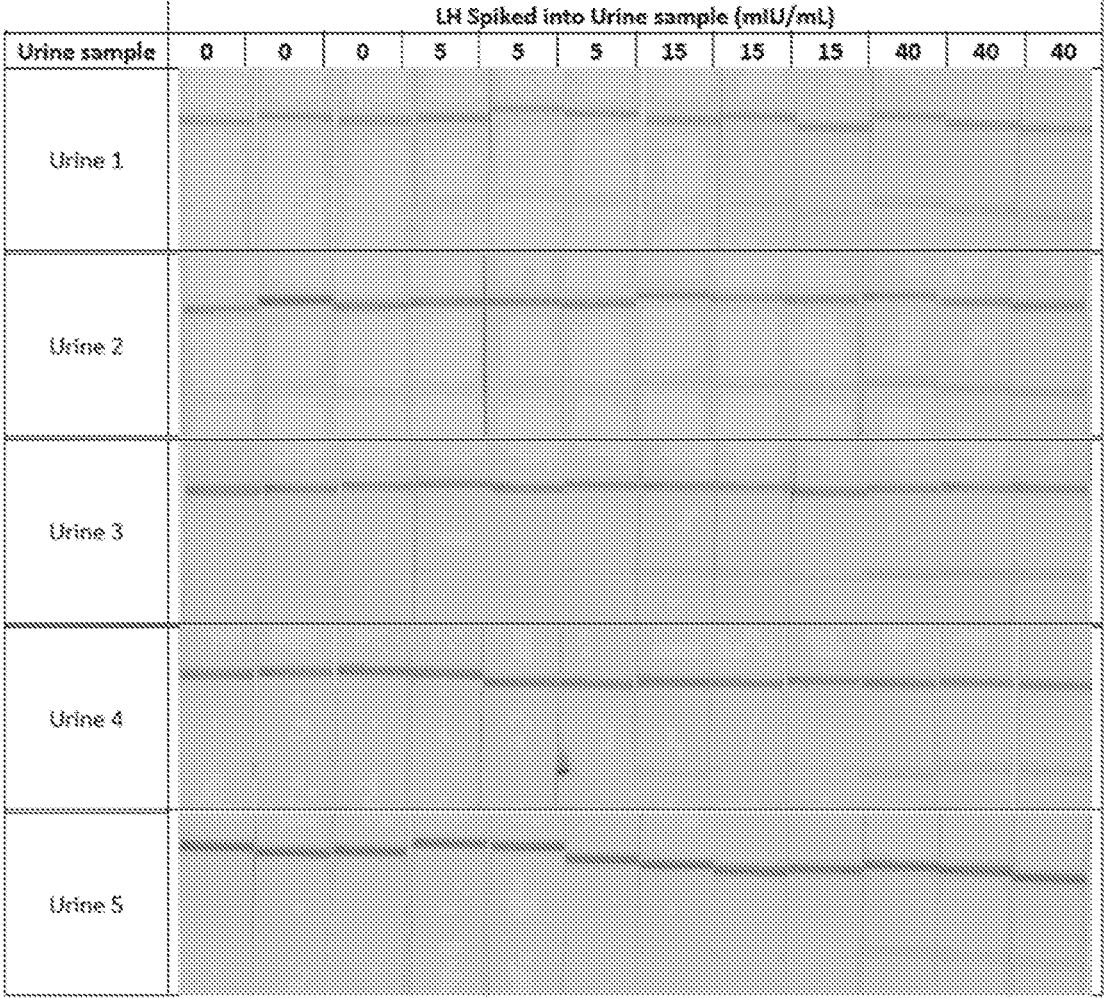
FIG. 15 shows detection of luteinizing hormone (LH) on lateral flow strips contacted with five different urine samples into which with varying amounts of LH were spiked. The lateral flow strips used clone pair C/4.

Clone pair C/4: The second strip for Urine 2 at a LH concentration of 0 mIU/mL was run with twice the amount of the conjugate, resulting in darker test and control lines. All urine samples showed a signal at titration. The signal for Urine 5 was significantly lower than the other urine samples. FIG. 15 shows the results obtained from clone pair C/4.

Figure 16:
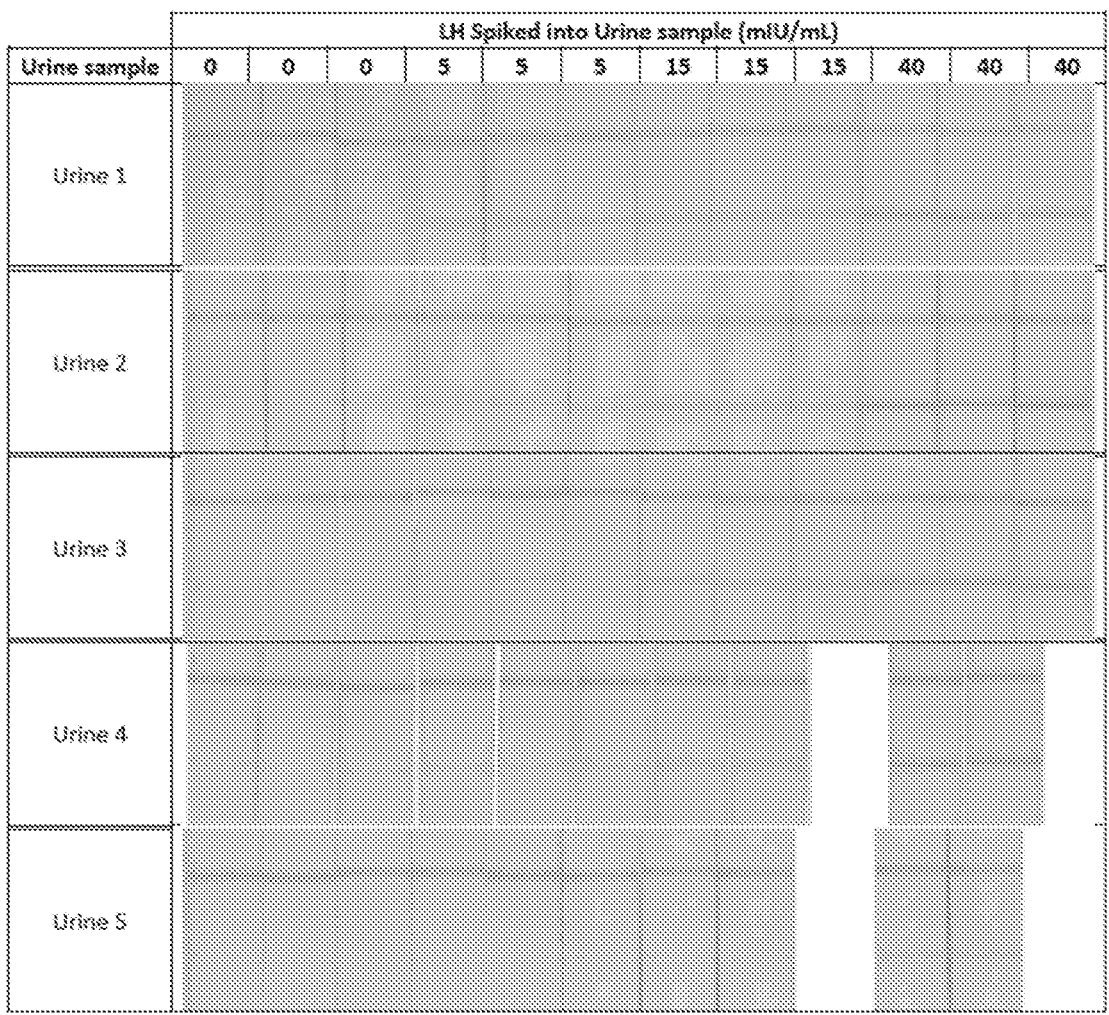
FIG. 16 shows detection of luteinizing hormone (LH) on lateral flow strips contacted with five different urine samples into which with varying amounts of LH were spiked. The lateral flow strips used clone pair A/5.

Clone pair A/5: All urine samples showed a titration. Urine 2 had the highest initial signal at 0 mIU/mL, and Urine 5 had the lowest signal of all the urine samples. FIG. 16 shows the results obtained from clone pair A/5.

Figure 17:
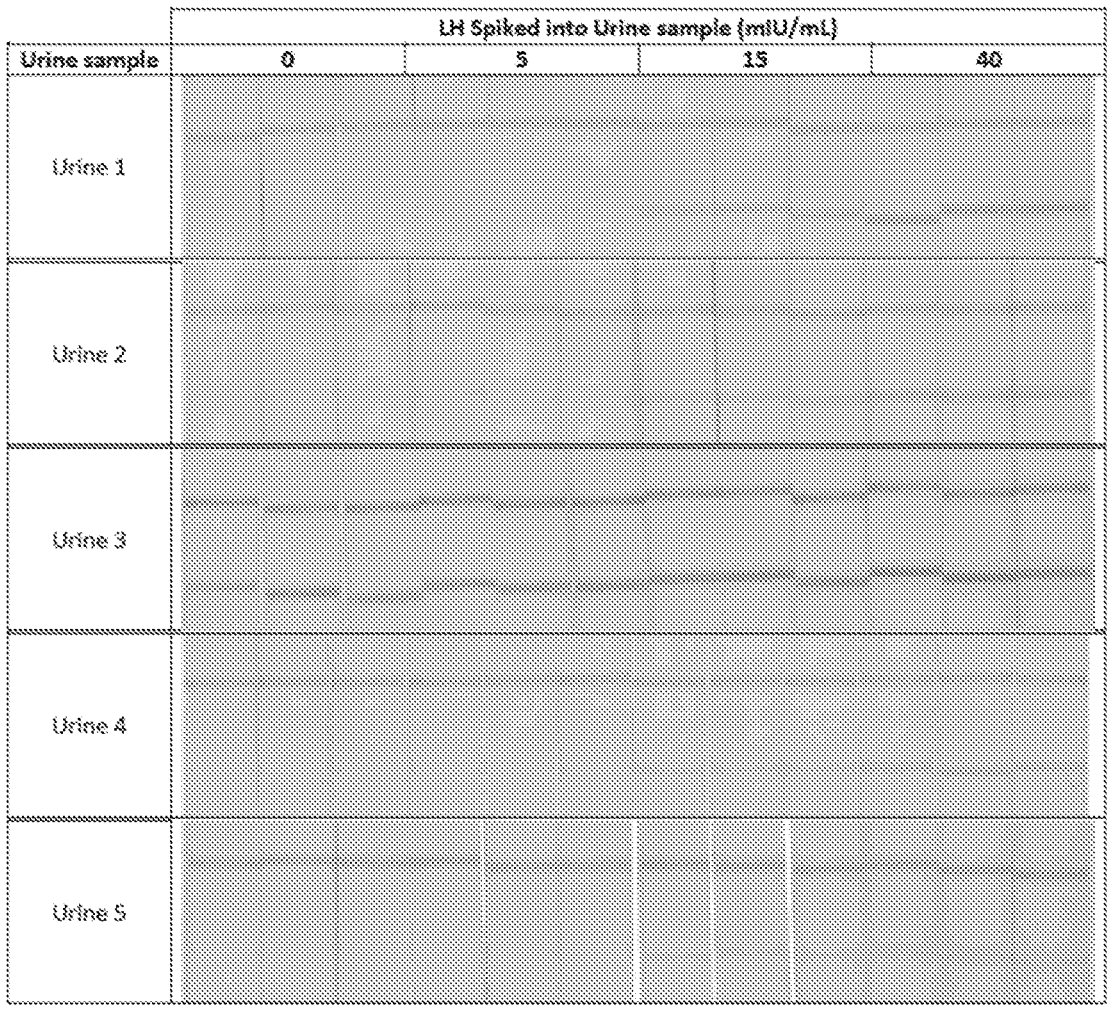
FIG. 17 shows detection of luteinizing hormone (LH) on lateral flow strips contacted with five different urine samples into which with varying amounts of LH were spiked. The lateral flow strips used clone pair 2/D.

Clone pair 2/D: Urine 1 showed discoloration of the gold conjugates with the higher concentration of spiked LH (15 and 40 mIU/mL). Urine 3 showed completed discoloration and very high nonspecific binding for all spiked LH concentrations. FIG. 17 shows the results obtained from clone pair 2/D.

Figure 18:
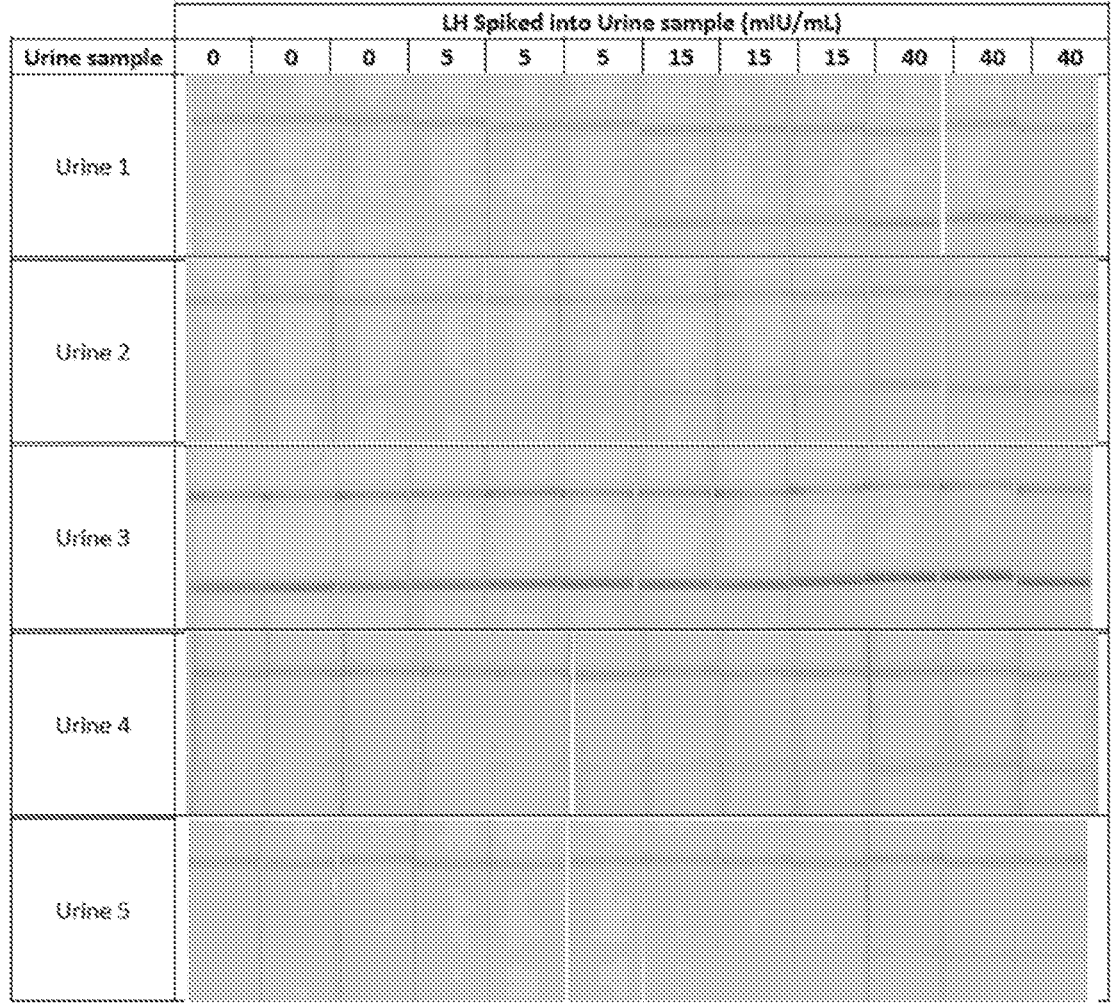
FIG. 18 shows detection of luteinizing hormone (LH) on lateral flow strips contacted with five different urine samples into which with varying amounts of LH were spiked. The lateral flow strips used clone pair 6/D.

Clone pair 6/D: Urine 1 showed discoloration of the gold conjugates with higher concentrations of LH (15 and 40 mIU/mL). Urine 3 showed complete discoloration and very high non-specific binding for all spiked LH concentrations. The pattern was similar to that observed for clone pair 2/D. The gold conjugate antibody (clone D) was shared between the two samples. FIG. 18 shows the results obtained from clone pair 6/D.

Figure 19:
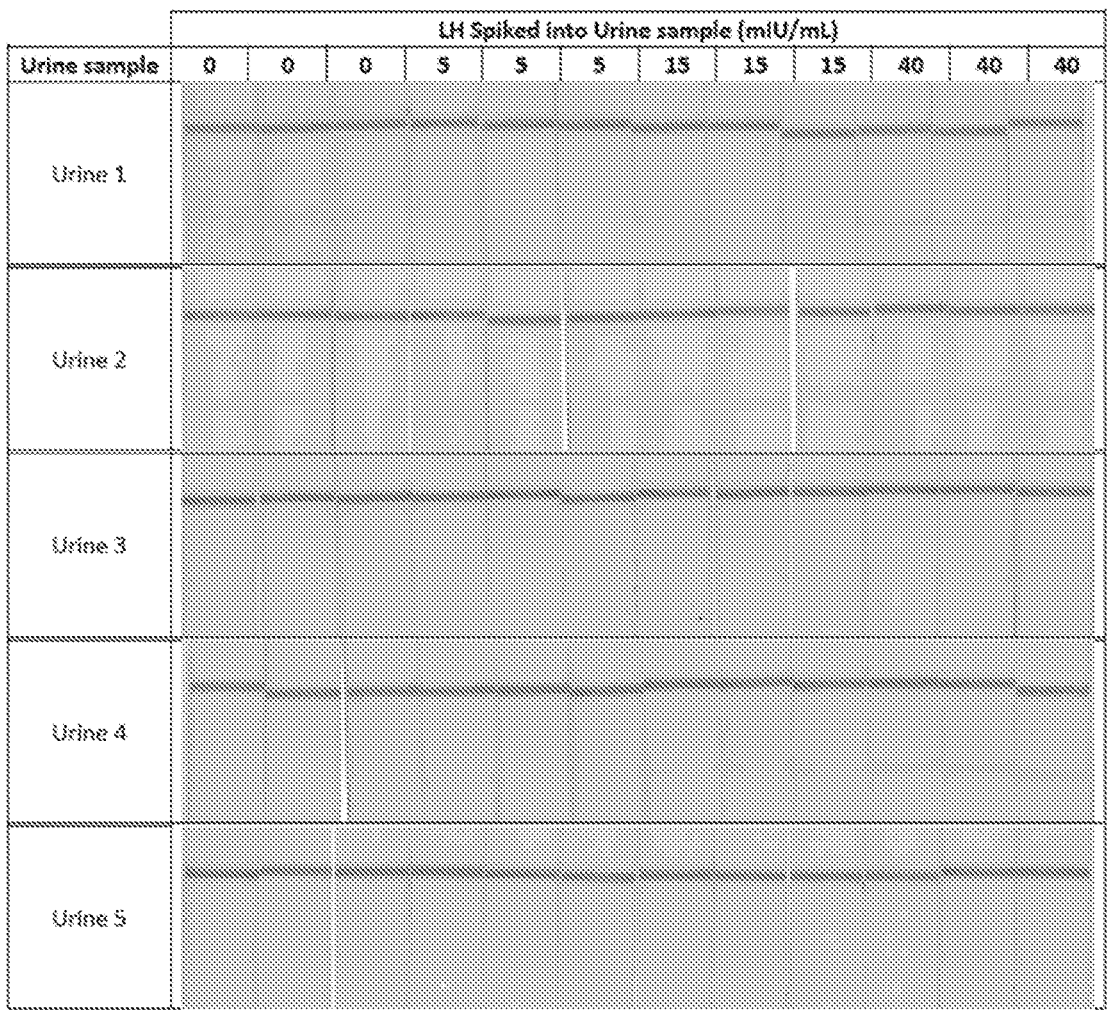
FIG. 19 shows detection of luteinizing hormone (LH) on lateral flow strips contacted with five different urine samples into which with varying amounts of LH were spiked. The lateral flow strips used clone pair 5/H.

Clone pair 5/H: The clone pair produced the lowest signals of the tested pairs. Urine 3 and Urine 5 yielded very low test line signals. FIG. 19 shows the results obtained from clone pair 5/H.

Figure 20:
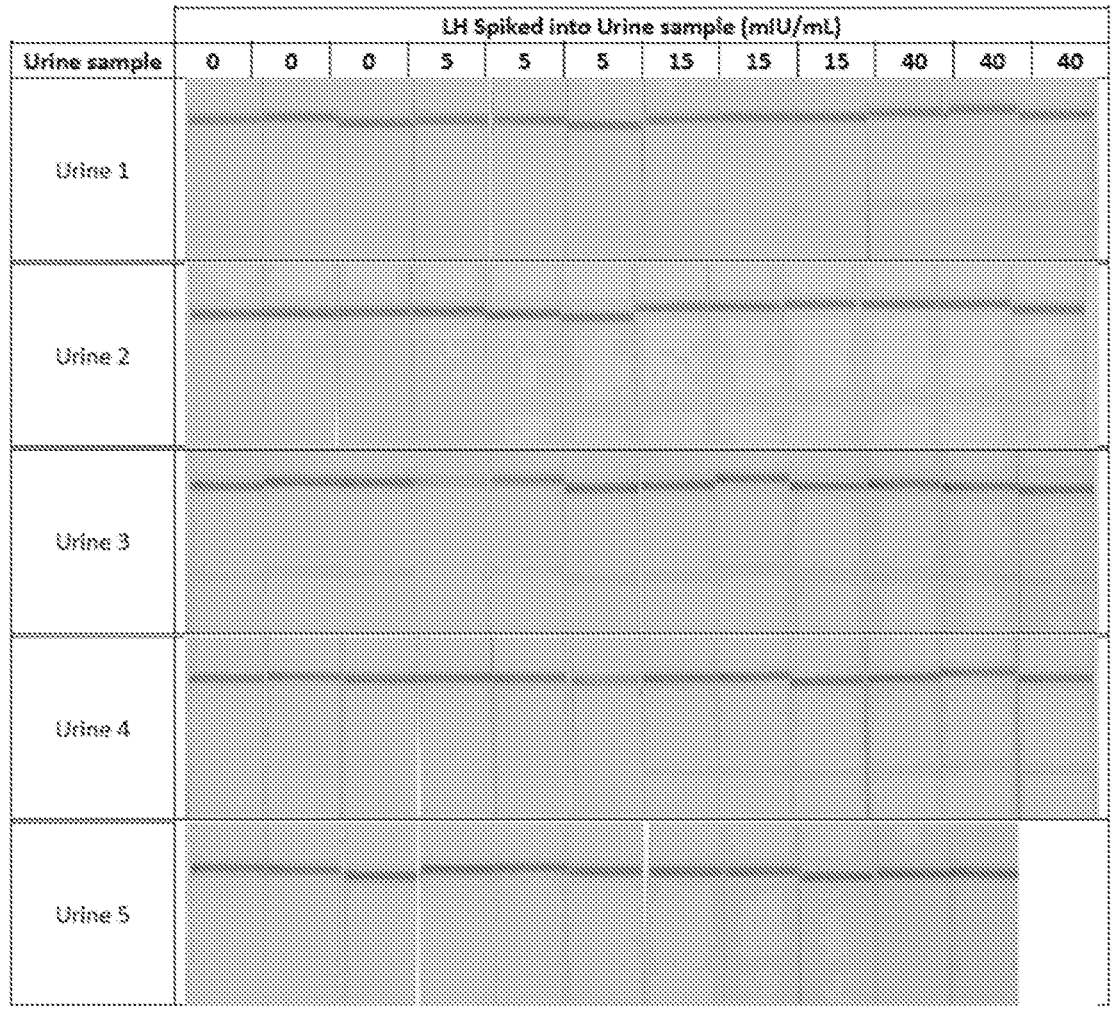
FIG. 20 shows detection of luteinizing hormone (LH) on lateral flow strips contacted with five different urine samples into which with varying amounts of LH were spiked. The lateral flow strips used clone pair 6/H

Clone pair 6/H: The binding levels for Urine 1-Urine 4 were similar. Urine 5 had lower test signals. FIG. 20 shows the results obtained from clone pair 6/H.

Example 3: Image Capture Device

An image capture reader was used to capture the results of the quantitative test strips. The primary components of the reader were: 1) a raw camera sensor; 2) LED lights; 3) a microcontroller; and 4) simple optics. The goal of the reader was to capture a high resolution, magnified image of the diagnostic strip.

The imaging apparatus prototype was designed to be modular enough to be able to iterate on the hardware until sufficient images could be acquired. The imaging apparatus prototype comprised of a cool white, 10 mm diameter light-emitting diodes (LEDs); an 8 megapixel Raspberry Pi Camera v2; a Raspberry Pi 3 with Raspian Light OS, python 3.1, and OpenCV package for image capture control and storage; and a 7.5× magnifier glass optical lens.

Figure 21:
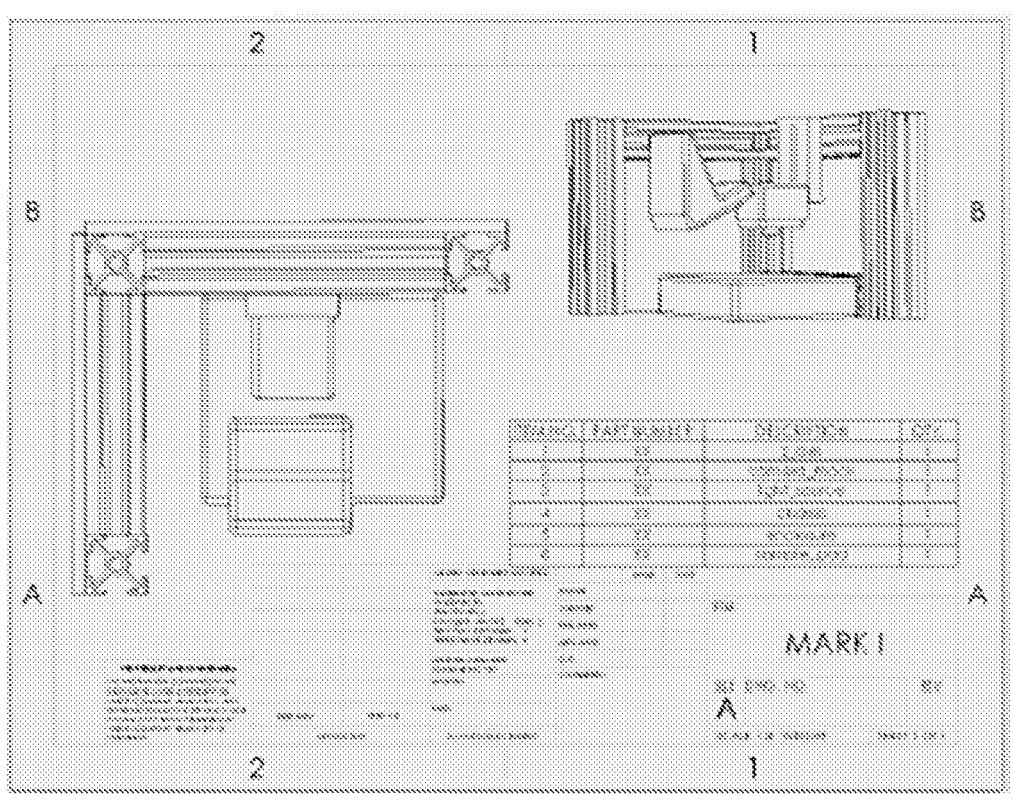
FIG. 21 shows a blueprint of an image capture reader for detecting pixel intensities.
Figure 22:
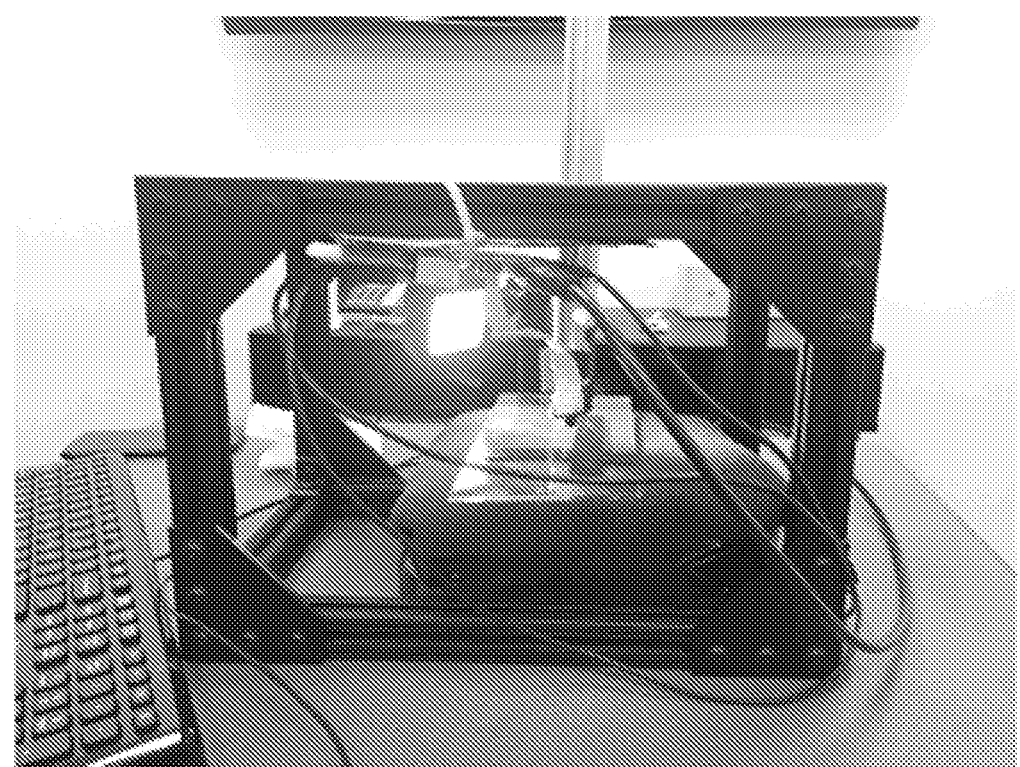
FIG. 22 shows a prototype of the image capture reader, which provides controlled lighting and a holder for a test strip

FIG. 21 shows a blueprint of the image capture reader. FIG. 22 shows a prototype of the image capture reader, which provided controlled lighting and included a holder for a test strip.

Example 4: Image Processing a. Region of Interest

Figure 23:
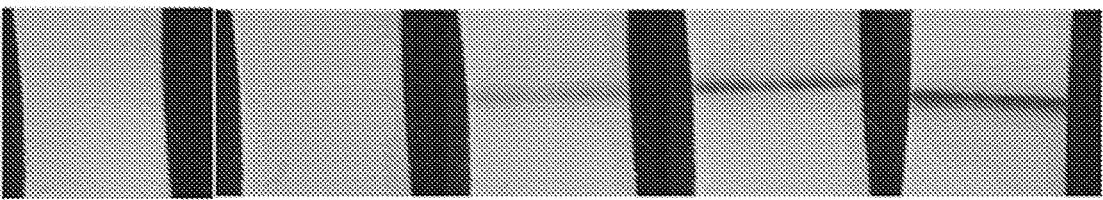
FIG. 23 shows images displaying varying intensities of the test lines captured by the image capture reader prototype.

Image processing first required identifying a region of interest. Image processing captured lines of varying intensities using the image capture prototype. FIG. 23 shows images displaying varying intensities of the test lines captured by the image capture reader prototype.

Figure 24:
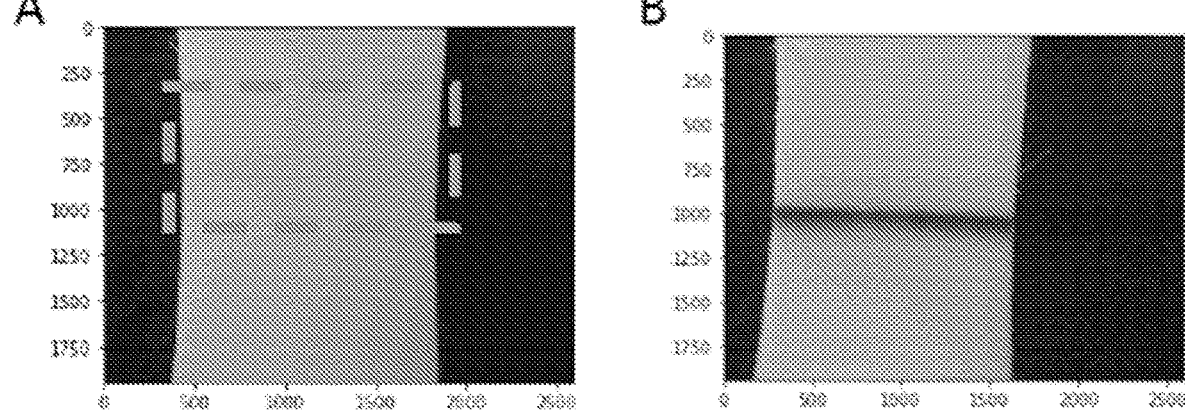
FIG. 24A displays a very light but visually detectable line.
FIG. 24B shows a dark line.

Regions of interest were programmatically detected. Identification of the image boundary was important to include only objects of interest. When the measured region was too small, the overall comparison to the control was skewed in one direction. If the measured region was too large, the results were skewed in the other direction. FIG. 24A displays a very light, visually detectable line. FIG. 24B shows a dark line.

Figure 25:
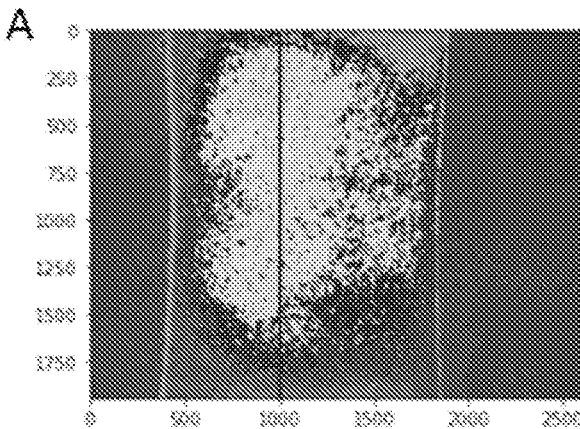
FIG. 25A shows the image of FIG. 24A in the hue channel.
FIG. 25B shows the image of FIG. 24A in the saturation channel.
FIG. 25C shows the image of FIG. 24A in the value channel.
Figure 25:
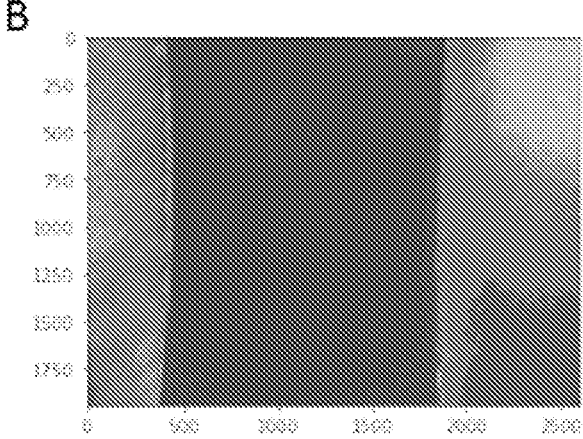
Figure 25:
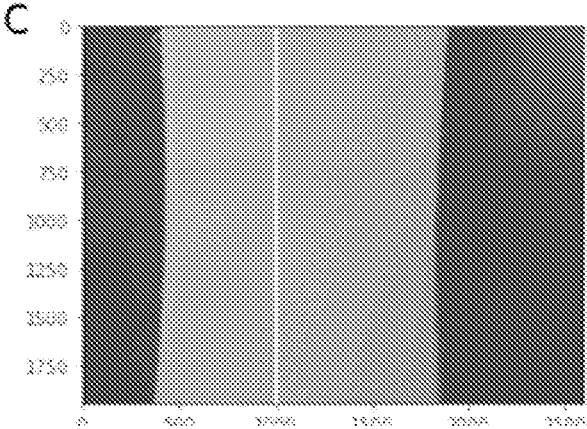

The hue, saturation, and value (HSV) color space was utilized over RGB. By isolating the color components into a single channel, finer adjustments were made in contrast and intensity. The line of interest was easiest to detect in the value color space. In each image, a vertical line was present. The line represented the trajectory for tracking pixel intensity (i.e., scan line). The goal was to plot the pixel intensity along the scan line, and when the iteration got to the "test line", to observe a gradient descent. FIG. 25A shows the separation of original images into the hue channel. FIG. 25B shows the separation of original images into the saturation channel. FIG. 25C shows the separation of original images into the value channel.

Figure 26:
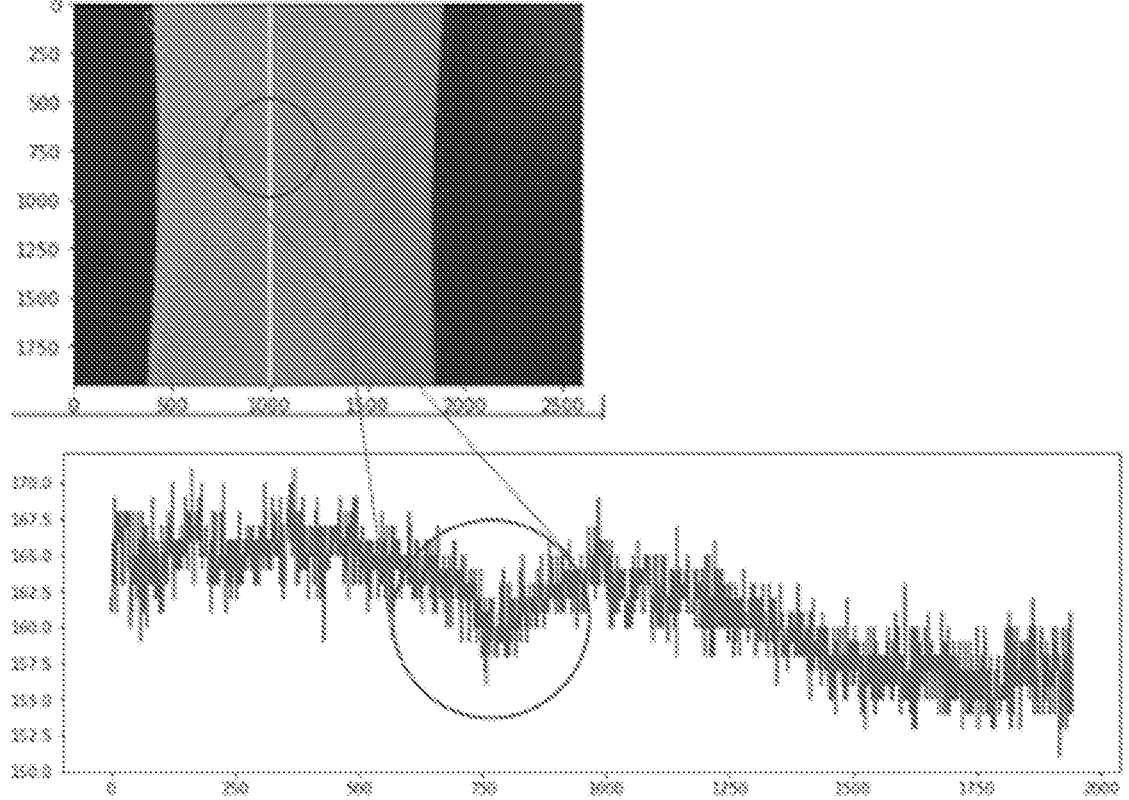
FIG. 26 TOP PANEL shows the image of FIG. 24A for processing, with a vector to be processed in white.
Figure 27:
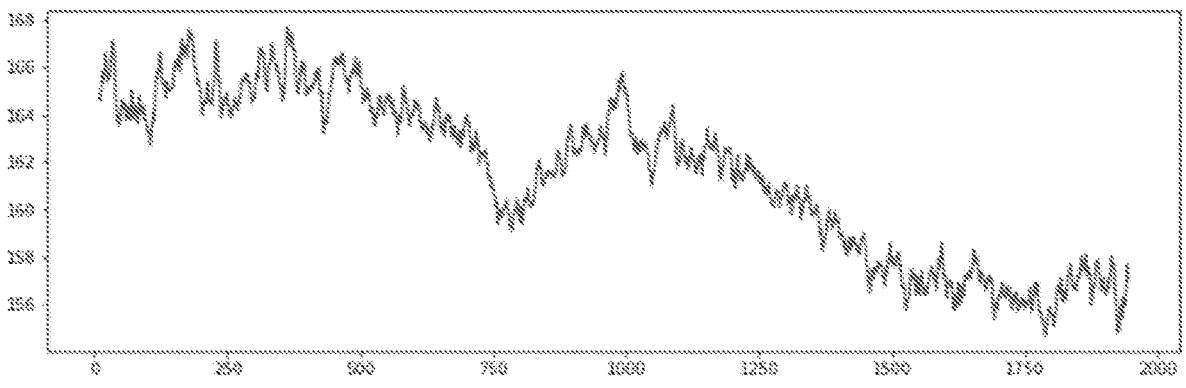
FIG. 27 shows the processed signal of FIG. 26 BOTTOM PANEL that was scrubbed and condensed.

Processing a signal, such as the signals of FIG. 25A, FIG. 25B, and FIG. 25C, was computationally extensive because the amount of data to be evaluated was very high. Each image was viewed as a matrix, where each pixel was assigned an intensity level. The resulting matrix was deconstructed into a single vector of pixel intensities following the scan line. FIG. 26 TOP PANEL shows an image that was used for processing. The highlighted area depicts the area that was deconstructed into a single vector of pixel intensities. To reduce the number of data points, the signal was scrubbed and condensed using a rolling mean that iterated on bin size until the signal fit a boundary model. FIG. 26 BOTTOM PANEL shows the results for the image intensities along a single column of the highlighted portion of the TOP PANEL. FIG. 27 shows the processed signal that was scrubbed and condensed.

Techniques to isolate the peaks were applied to the scrubbed and condensed signal. The peaks were of interest because the peaks identified the point at which the test line occurred. Peaks were observed normal to the scan line where there was a drastic reduction in signal intensity. If an area with a drastic reduction in signal intensity was identified, the boundary coordinates for the test line could be determined.

Figure 28:
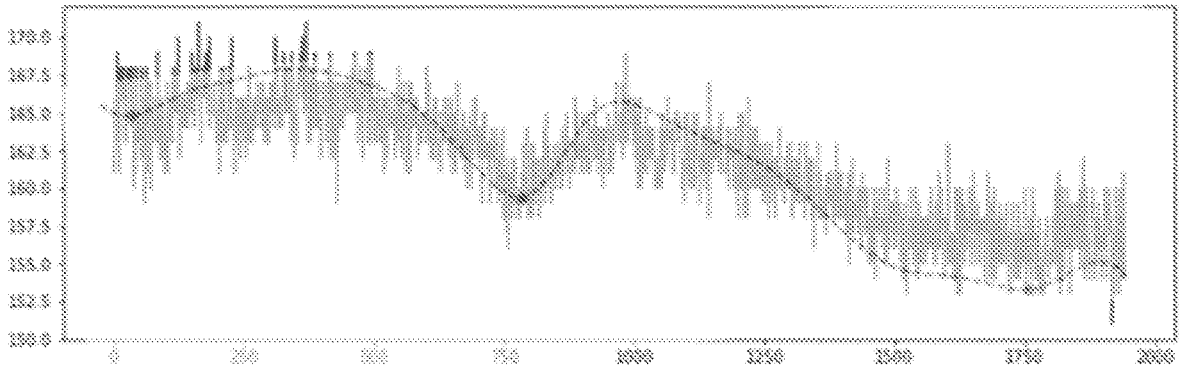
FIG. 28 shows the Scikit mathematical representation and peak identification.

The first step in identifying the peaks was to develop a function that fit the shape of the signal. The structure was characterized using a polynomial spline. The Scikit-learn python package was used to iterate over the function, and to identify the most suitable representation of the signal. The spline was then used to run peak sorting algorithms to identify the peaks with the highest magnitude and the greatest gradient. FIG. 28 shows the Scikit mathematical representation and peak identification.

Figure 29:
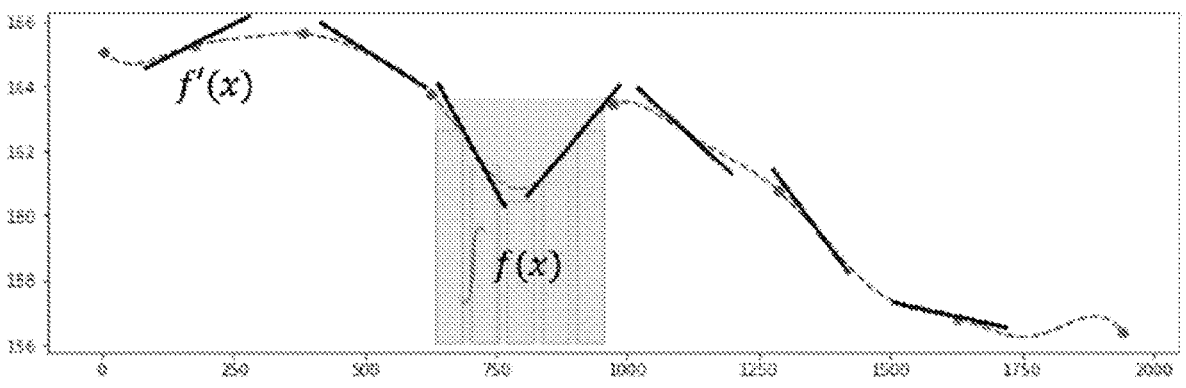
FIG. 29 shows the implementation of the Trapezoidal rule to identify the total area.

After signal was thoroughly processed and represented, two boundary conditions were used to identify which peak was the most significant. The area below the curve at each qualified "valley" was used to determine where the largest peak was. A Riemann Integral, followed by the Trapezoidal rule, was used to determine the largest peak. The total area across the respective inflection points was calculated, and the area below the curve was subtracted out. FIG. 29 shows the implementation of the Trapezoidal rule to identify the total area. Then, the gradient along rolling intervals of 100 pixels was calculated and stored in a list to scan and identify the maximum.

Figure 30:
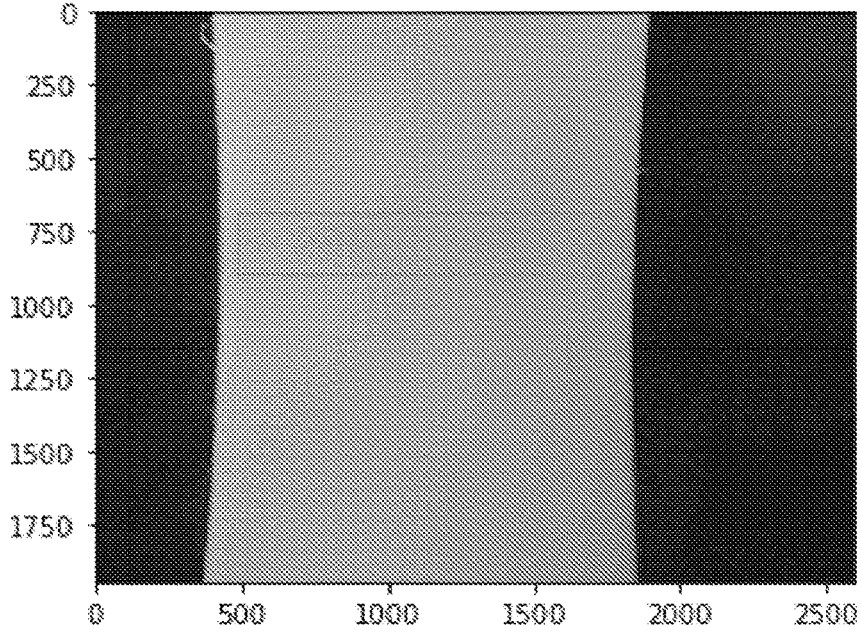
FIG. 30 shows the identification of a region of interest in the image of FIG. 24A.

The centroid of the most significant peak identified represented the longitudinal and latitudinal center of the test line. The points that represented the start and stop of the gradient descent represented the height and width of the test line. FIG. 30 shows the identification of a region of interest. The boundary box highlights the test line and the region of interest for analysis.

b. Analysis

Once the region of interest was identified, the results within the boundary were analyzed. A model was developed to take an image obtained from a lateral flow device as input, and to provide a quantitative test line intensity result as the output. The method included: 1) removing noise from the images using several morphological transformations; 2) calculating the histogram for each variant; 3) comparing the histogram of each variant to the control variant; 4) looping through various methods of comparison, using linearity as a guide; 5) plotting the comparison data against the known variant intensities as specified by the test dummy batch numbers; 6) developing the transfer function; and 7) using the transfer function to predict the intensity of several test samples and further train the regression model.

Figure 31:
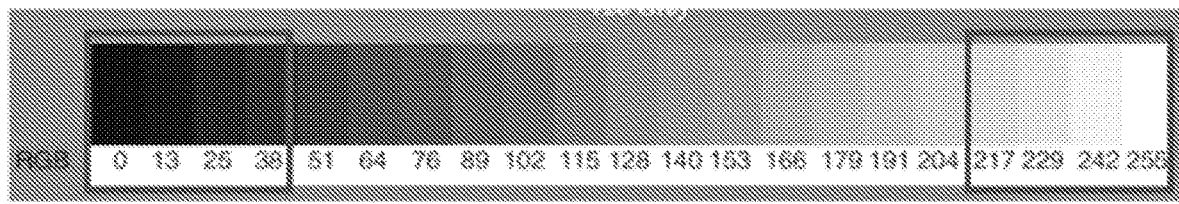
FIG. 31 shows an RGB chart with background and strip with shadows.

Unlike RGB, HSV separates luma, the image intensity, from chroma, the color information. With respect to test strips, the black background had pixel intensities approaching 0, and shadowing anomalies throughout the strip surface, which had pixel intensities approaching 255. FIG. 31 shows an RGB chart with background and strip with shadows. Once the intensity components that represented a useful signal and noise signals were distinguished, the images were cleaned up further. A series of morphological transformations, such as watershed, segmentation, and topological optimization were used.

Figure 32:
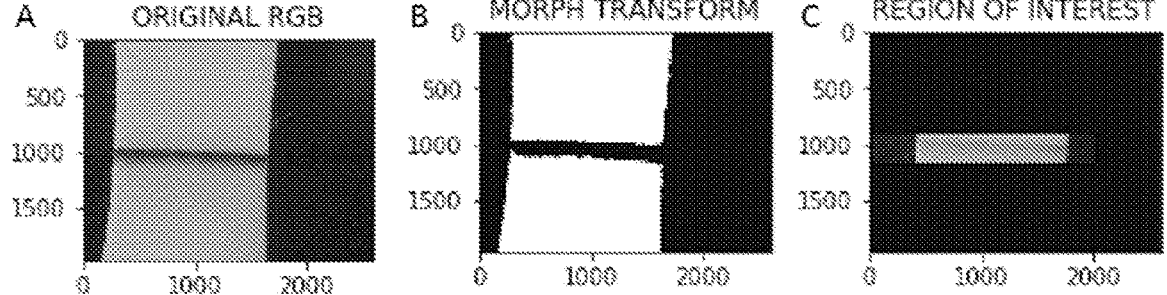
FIG. 32A shows an original image captured by the image capture prototype device.
FIG. 32B shows the binary result from the morphological transformation of the original image.

In image processing, watershed is a transformation defined on a grayscale image. The watershed transformation treats the image it operates upon like a topographic map, with brightness of each point representing its height, and finds the lines that run along the tops of ridges. The result of this work is an image with two types of pixels: good and bad. FIG. 32A shows an original image captured by the image capture prototype device. FIG. 32B shows the binary result from the watershed transformation of the original image. FIG. 32C shows the mask that was created to isolate the region of interest.

Figure 33:
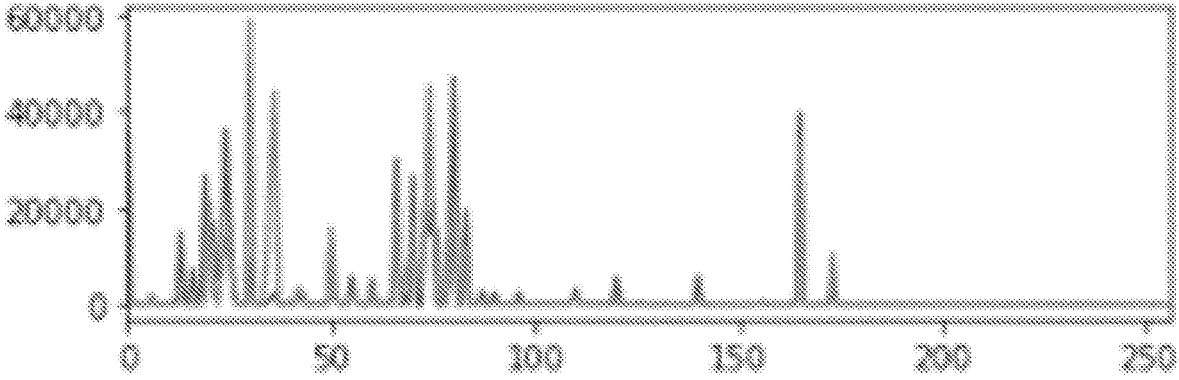
FIG. 33 shows intensity histograms of the control line and the test line, where the control line is the darkest intensity observed and the test line is the second line being compared to the control line.

After defining the final stage of the image, the intensity histograms of each variant was compared against the control. FIG. 33 shows intensity histograms of the control line and the test line, where the control line is the darkest intensity observed and the test line is the second line being compared to the control line. From the initial experiment, variant_1 was used as the control because it represented the most intense line in all the batches. The comparison was done using different types of structural statistical tests: correlation, Chi-square, intersection, and Bhattacharyya distance tests. The efficacy of each one of the tests was quantified using linearity.

Correlation (method=CV_COMP_CORREL)

$$d(H_1, H_2) = \frac{\sum_I (H_1(I) - \bar{H}_1)(H_2(I) - \bar{H}_2)}{\sqrt{\sum_I (H_1(I) - \bar{H}_1)^2 \sum_I (H_2(I) - \bar{H}_2)^2}}$$

where $$\bar{H}_k = \frac{1}{N} \sum_J H_k(J),$$

and N is a total number of histogram bars.

Chi-Square (method=CV_COMP_CHISQR)

$$d(H_1, H_2) = \sum_I \frac{(H_1(I) - H_2(I))^2}{H_1(I)}$$

Intersection (method=CV_COMP_INTERSECT)

$$d(H_1, H_2) = \sum_I \min(H_1(I), H_2(I))$$

Bhattacharyya distance (method=CV_COMP_BHATTACHARYYA or method=CV_COMP_HELLINGER). OpenCV computes Hellinger distance, which is related to the Bhattacharyya coefficient.

$$d(H_1, H_2) = \sqrt{1 - \frac{1}{\sqrt{\bar{H}_1 \bar{H}_2 N^2}} \sum_I \sqrt{H_1(I) \cdot H_2(I)}}$$

TABLE 1 shows the correlation results for each of the structural statistical tests evaluated. The Bhattacharyya method performed most effectively. TABLE 1 shows the combination results for each of the structure statistical tests evaluated.

TABLE 1

| Method | R | $R^2$ |
|---|---|---|
| Correlation | 0.971 | 0.943 |
| Chi-Square | 0.978 | 0.957 |
| Intersection | 0.968 | 0.937 |
| Bhattacharyya | 0.982 | 0.965 |

Figure 34:
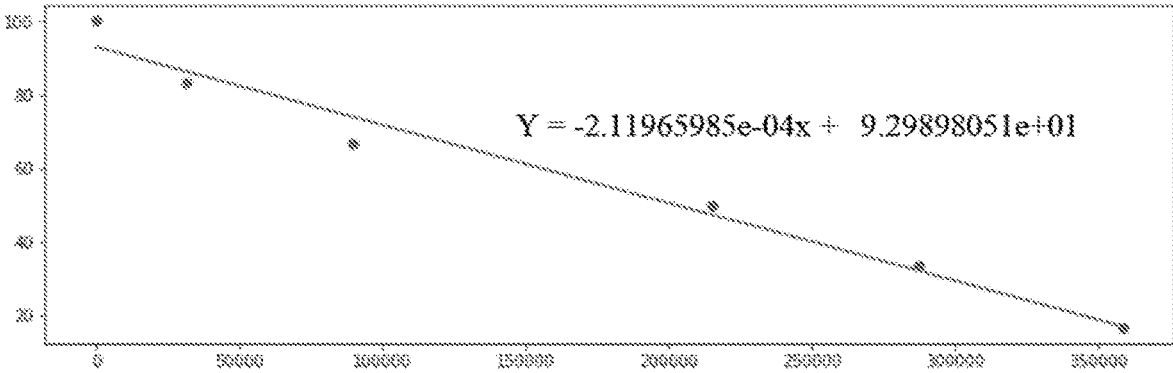
FIG. 34 shows the linear regression model for the Bhattacharyya method
Figure 35:
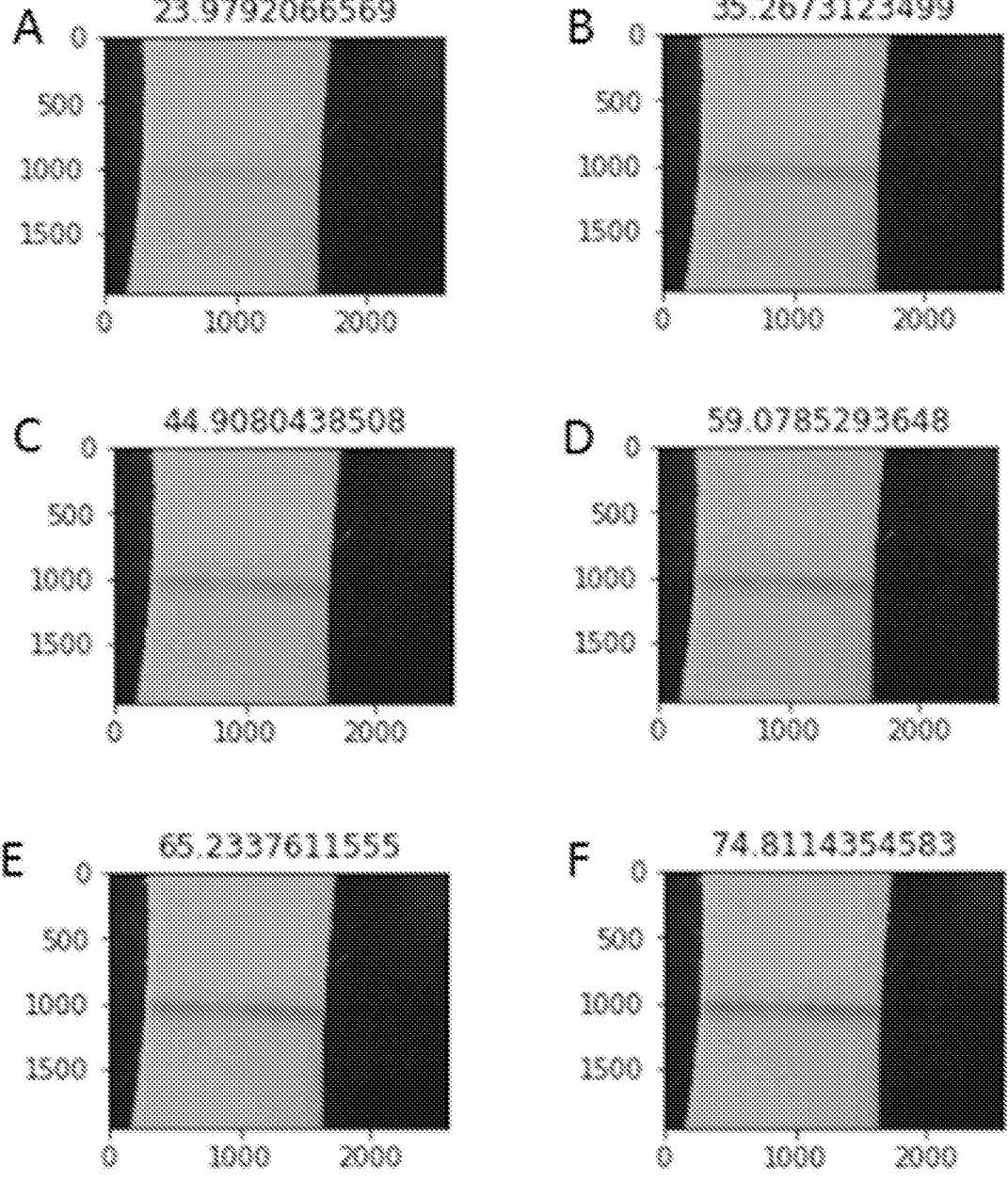
FIG. 35A, FIG. 35B, FIG. 35C, FIG. 35D, FIG. 35E, and FIG. 35F depict the image of FIG. 24A, quantified at varying intensities.

The Bhattacharyya method performed most effectively. FIG. 34 shows the linear regression model for the Bhattacharyya method. The linear regression model that best fit the data is listed in the figure, where x is the Bhattacharya distance between variant N and variant_1 (control).

Random images were plugged into the model to determine how well the function quantified the associated intensities of each line. Six images were taken from variant_1 at different time points of population. The input to the linear regression model was simply the composite Bhattacharyya distance score. FIG. 35A, FIG. 35B, FIG. 35C, FIG. 35D, FIG. 35E, and FIG. 35F shows the results from applying the model to lines of varying intensities. The derived intensity of each test line through application of the algorithm is listed above each panel.

Example 5: Evaluation of Clone Pair A/5 in Urine with Half-Strips a. Half-Strip Assembly

Figure 36:
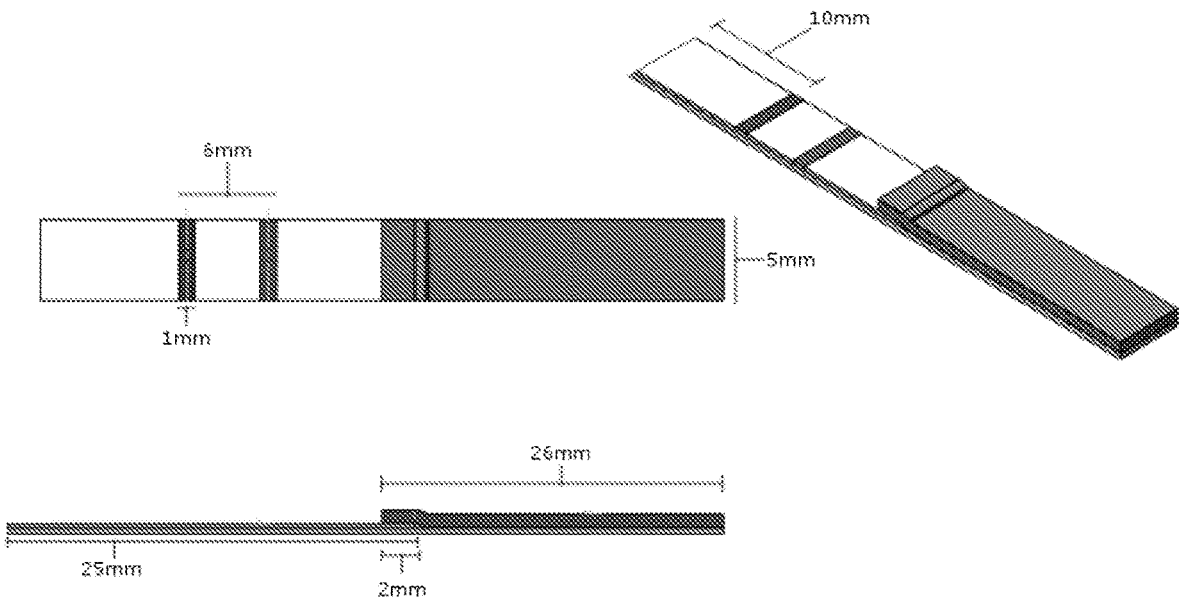

Half-strips were comprised of a rigid backing card, a nitrocellulose membrane with test and control lines, and an absorbent pad that acts as a reservoir. Details on the components of half-strips as well as the antibodies and conjugates used in this study are shown below in TABLE 2. A schematic of a strip can be seen in FIG. 36.

TABLE 2

| Component | Material | Manufacturer | Other |
|---|---|---|---|
| Nitrocellulose Membrane | CN95 | Sartorius | Length: 25 mm |
| Absorbent Pad (Wick) | C083 | Millipore | Length: 26 mm |
| Backing Card | Vinyl | Lohman | Dimensions: 60 mm × 300 mm |
| Conjugate Antibody | Anti-LH antibody | Biospacific | Purified monoclonal antibody |
| Test Antibody | Anti-hLH antibody 5301 SP-5 | Biospacific | Purified monoclonal antibody |
| Control Line Antibody | Goat anti-mouse antibody | Lampire | Purified Polyclonal antibody |
| Conjugate Label | Colloidal gold | DCN | Approximately OD1 and 40 nm diameter | b. Testing of Clone Pair A/5 in Spiked Urine

Six urine samples were used for testing, U1, U2, U3, U4, U5, and U6. Aliquots of each urine sample were spiked with various amounts of LH antigen to allow for the generation of dose response curves with each sample of urine. LH antigen used in the clone pair evaluation was purchased from NIBSC and was part of the 3<sup>rd</sup> World Health Organization (WHO) standard for human LH. Samples U1-U5 were each from individual urine donors. Sample U6 was a blend of urine from the donor of U4 and a sixth donor. For each of U1-U6 aliquots were prepared with spiked LH concentrations of 0, 5, 15, 40, 70, 100, and 200 mIU. For sample U4 only an additional aliquot with a spiked LH concentration of 1000 mIU/mL was prepared. 50 mM Tris buffer was used as a blank.

To run the LH detection assay 350 μL of each spiked urine concentration was brought to room temperature. Once aliquots equilibrated three reagents were mixed in sample wells: 5 μL of gold conjugate at an OD of 4, 5 μL running buffer and 40 μL of the designated urine sample or blank 50 mM Tris. The three added reagents were then mixed via aspiration. After mixing half-strips were placed in the sample wells for at least 15 minutes prior to data acquisition. Assays were performed in n=5 replicate wells for each concentration in each urine sample tested.

Figure 37:
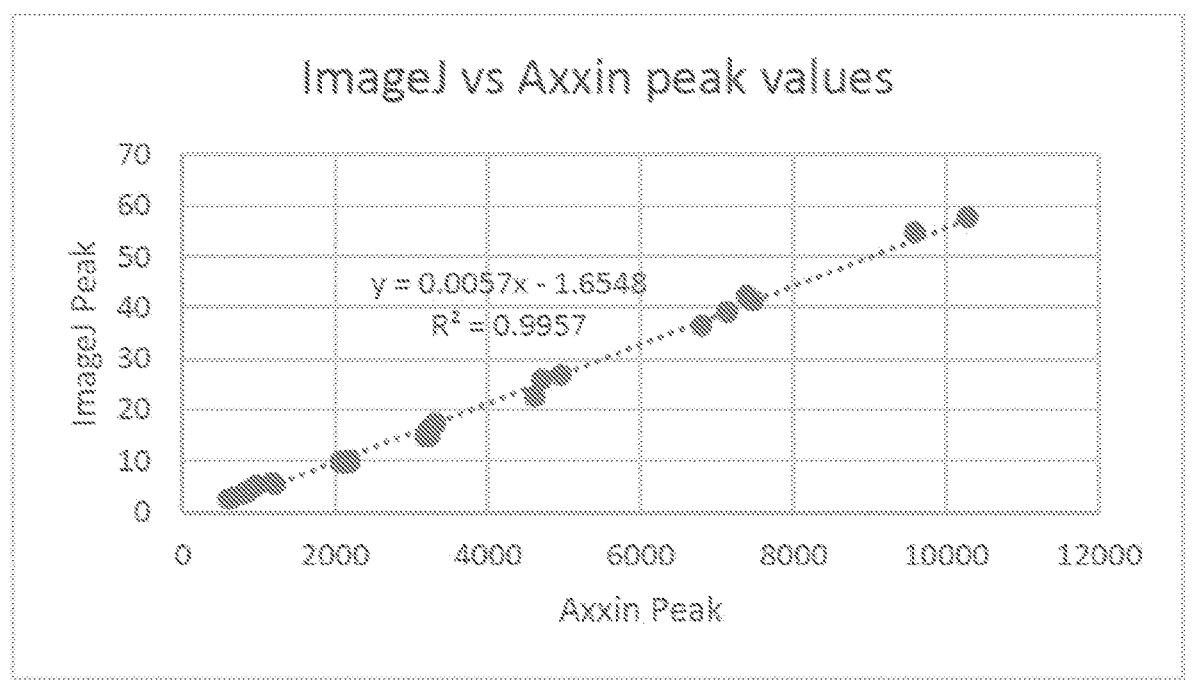
FIG. 37 shows the regression line used to generate the transfer function to convert between ImageJ and Axxin values.

Following incubation with assay solutions, half strips were read using an Axxin Reader or taped onto a paper, imaged and analyzed with ImageJ to assess the A/5 half-strip performance. To convert ImageJ values to Axxin peak values a transfer function was created wherein Axxin_Value=(ImageJ_Value−1.654771)/0.005727. As can be seen in FIG. 37, the transfer function was able to accurately convert between ImageJ and Axxin values.

Figure 38:
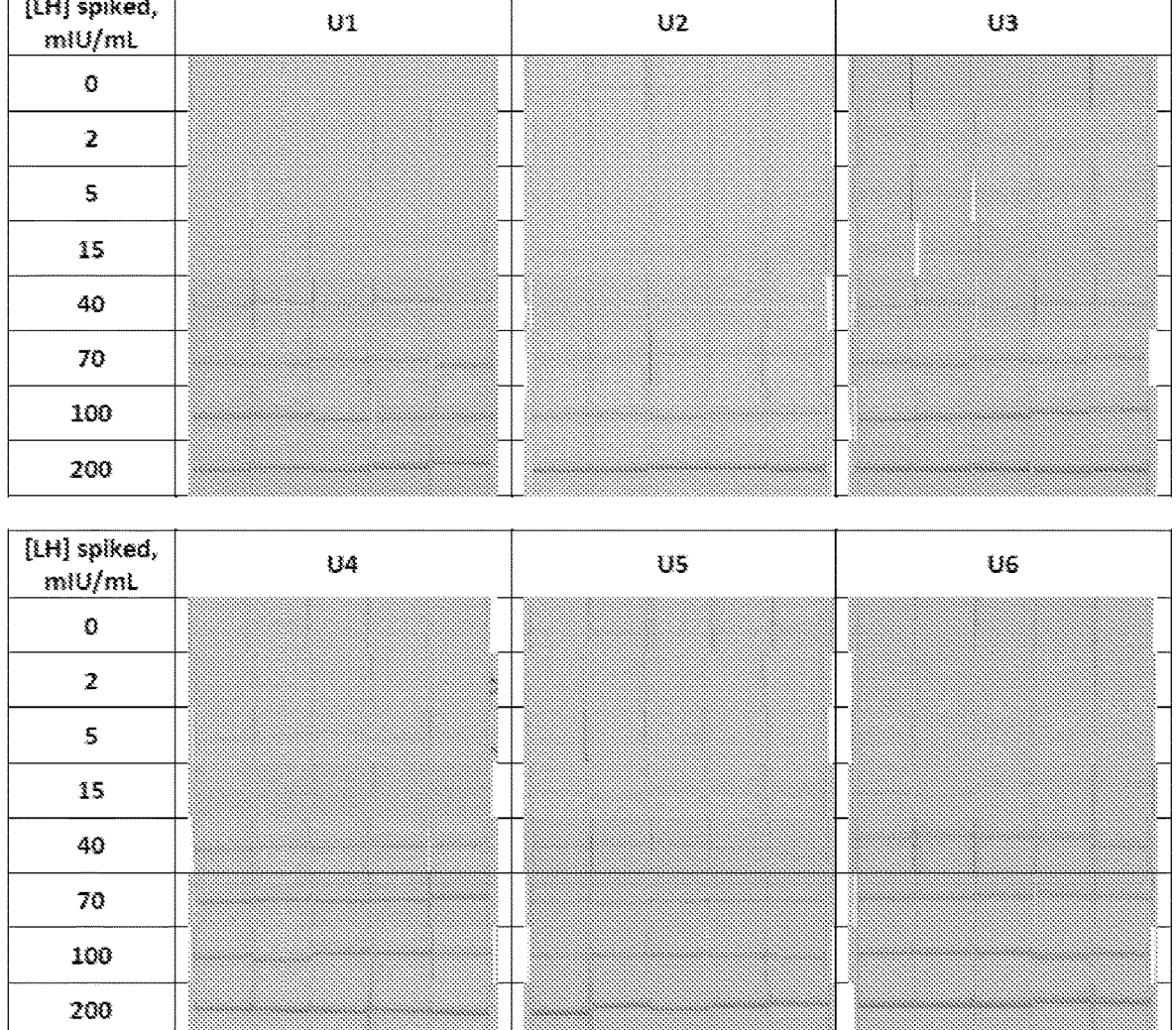
FIG. 38 shows images of test lines for spike urine samples U1-U6 described in EXAMPLE 5.
Figure 39:
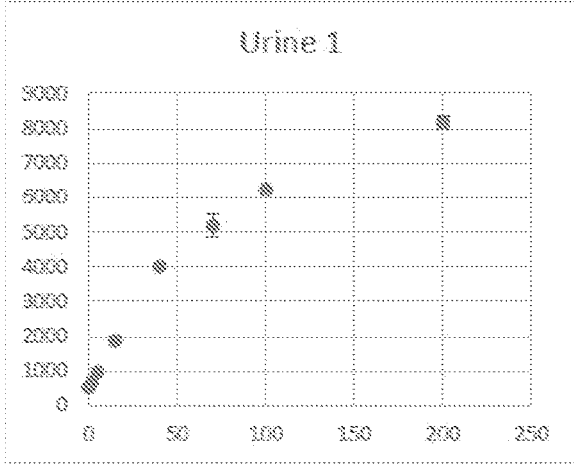
FIG. 39 shows graphs of individual urine samples with Axxin Peak Values on the y-axis, spiked LH Concentration (mIU/mL) on the x-axis, and error bars set at +/−one standard deviation
Figure 39:
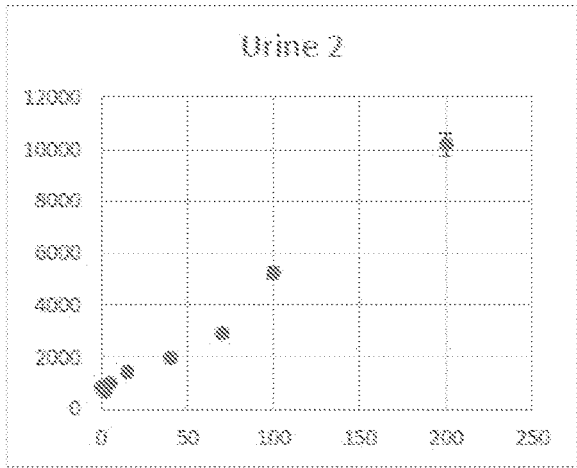
Figure 39:
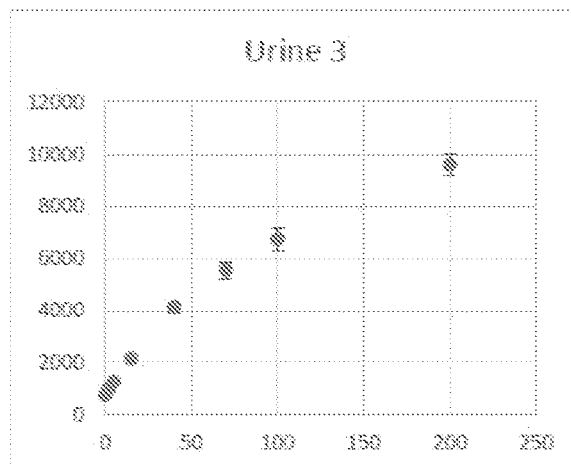
Figure 39:
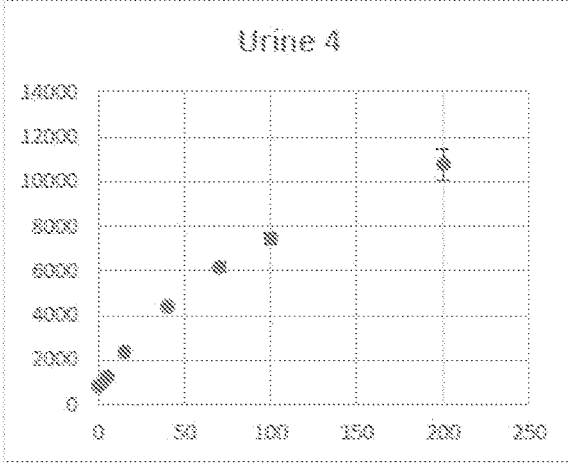
Figure 39:
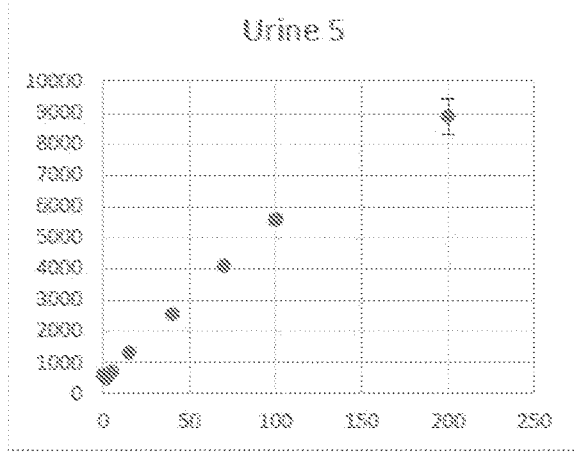
Figure 39:
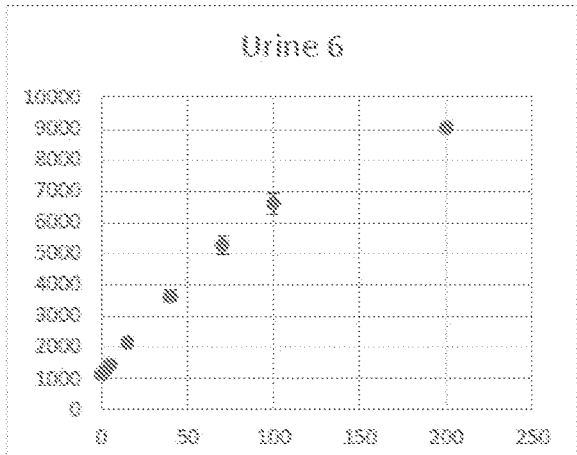
Figure 40:
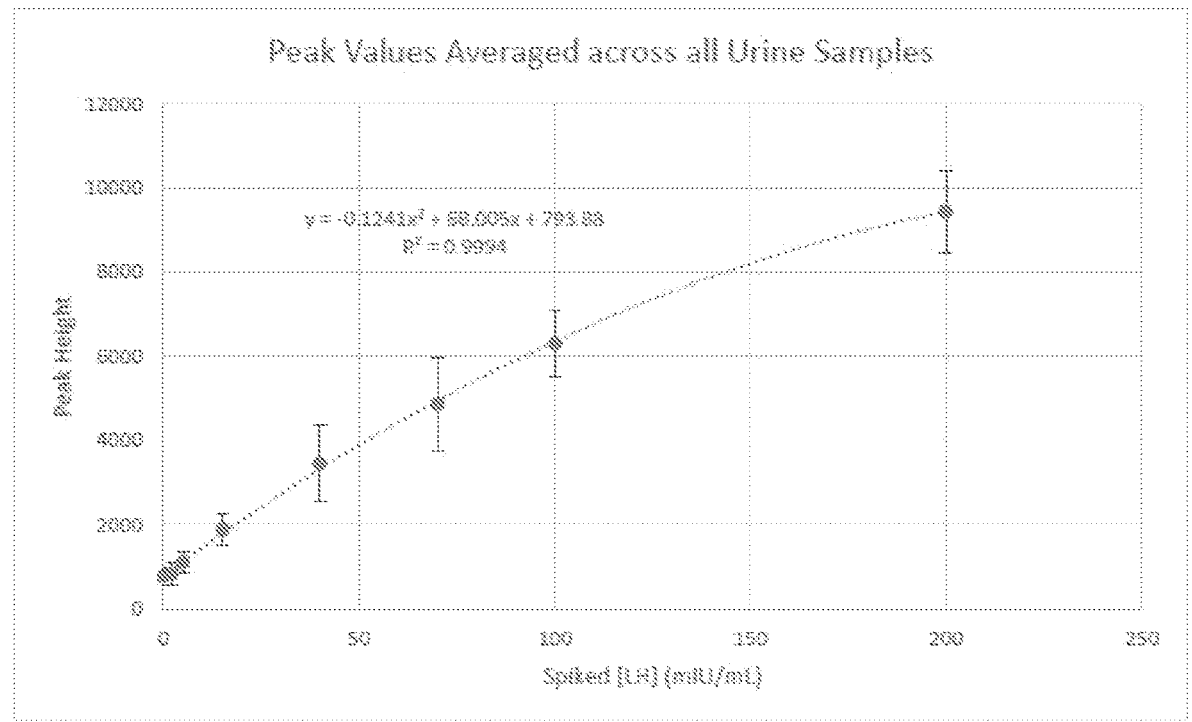
FIG. 40 shows a graph of averaged peak values across urine samples U1-U6 with error bars representing standard deviation.

A qualitative assessment of urine-incubated A/5 half-strips can be seen in FIG. 38. Images showed an increase in test line intensity with increasing LH concentration for all urine samples tested. Quantification of data showed a monotonic increase in average test line intensity for all urine samples spiked with 2, 5, 15, 40, 70, 100, 200, or 1000 mIU/mL LH as seen in TABLE 3 and FIG. 39. The samples demonstrate a narrow range of test line intensity values as quantified by the commercial reader. This can be seen in TABLE 4, where each cell of represents the difference between the lowest and the highest test line intensity observed in a set of five replicate measures of each sample. Moreover, the samples demonstrate a low coefficient of variation of test line intensity values as quantified by the commercial reader. Evidence of this is seen in TABLE 5, where each cell represents the intra-sample coefficient of variation of test line intensities. This is measured by taking the ratio of the standard deviation and the mean across all five replicates for a given sample. Lastly, though in samples U2 and U5 a slight decrease in test line intensity was seen in average test line intensity between samples spiked with 0 mIU/mL and 2 mIU/mL, the average test line intensity across all samples U1-U6 demonstrated monotonic behavior across the entire spectrum of LH concentrations tested as shown in FIG. 40.

TABLE 3

| Spiked [LH] (mIU/ mL) | U1 | U2 | U3 | U4 | U5 | U6 | Avg | Std Dev | % CV |
|---|---|---|---|---|---|---|---|---|---|
| 0 | 533 | 855 | 735 | 828 | 599 | 1135 | 781 | 203 | 26% |
| 2 | 678 | 696 | 972 | 942 | 474 | 1254 | 836 | 264 | 32% |
| 5 | 962 | 1034 | 1259 | 1238 | 696 | 1447 | 1106 | 252 | 23% |
| 15 | 1871 | 1464 | 2153 | 2344 | 1323 | 2152 | 1884 | 389 | 21% |
| 40 | 4014 | 1995 | 4120 | 4383 | 2544 | 3635 | 3448 | 901 | 26% |
| 70 | 5183 | 2934 | 5566 | 6182 | 4092 | 5274 | 4872 | 1108 | 23% |
| 100 | 6246 | 5245 | 6750 | 7464 | 5576 | 6610 | 6315 | 791 | 13% |
| 200 | 8160 | 10211 | 9618 | 10774 | 8886 | 9021 | 9445 | 974 | 10% |
| 1000 | | | | 16056 | | | 16056 | 303 | 2% |

CV= Coefficient of Variation

TABLE 4

| Spiked [LH] (mIU/mL) | U1 | U2 | U3 | U4 | U5 | U6 | Avg |
|---|---|---|---|---|---|---|---|
| 0 | 59 | 47 | 42 | 36 | 52 | 46 | 47 |
| 2 | 40 | 21 | 59 | 36 | 32 | 142 | 55 |
| 5 | 72 | 61 | 68 | 36 | 41 | 60 | 56 |
| 15 | 105 | 57 | 41 | 84 | 33 | 115 | 73 |
| 40 | 103 | 115 | 191 | 135 | 87 | 184 | 136 |
| 70 | 336 | 150 | 307 | 242 | 77 | 277 | 231 |
| 100 | 101 | 206 | 422 | 233 | 150 | 338 | 242 |
| 200 | 185 | 450 | 399 | 700 | 570 | 120 | 404 |
| 1000 | | | | 303 | | | |

TABLE 5

| Spiked [LH] (mIU/mL) | U1 | U2 | U3 | U4 | U5 | U6 | Avg |
|---|---|---|---|---|---|---|---|
| 0 | 11% | 5% | 6% | 4% | 9% | 4% | 7% |
| 2 | 6% | 3% | 6% | 4% | 7% | 11% | 6% |
| 5 | 7% | 6% | 5% | 3% | 6% | 4% | 5% |
| 15 | 6% | 4% | 2% | 4% | 2% | 5% | 4% |
| 40 | 3% | 6% | 5% | 3% | 3% | 5% | 4% |
| 70 | 6% | 5% | 6% | 4% | 2% | 5% | 5% |
| 100 | 2% | 4% | 6% | 3% | 3% | 5% | 4% |
| 200 | 2% | 4% | 4% | 6% | 6% | 1% | 4% |
| 1000 | | | | 2% | | | 2% | c. Sample Differentiation

To further assess the performance of the A/S half-strips the measurement of separation of U4 samples versus the combined urine data was analyzed. The general principle that guided this analysis is that if two neighboring concentrations, $C_1$ and $C_2$, have averages $\mu_1$ and $\mu_2$, and standard deviations $\sigma_1$ and $\sigma_2$, then separation can be defined in three ways: 1) distance from the lower concentration: $(\mu_2-\mu_1)/\sigma_1$; 2) Distance from the higher concentration: $(\mu_2-\mu_1)/\sigma_2$; and 3) combined concentration: $(\mu_2-\mu_1)/(\sigma_1+\sigma_2)$. The larger the separation, the more surely a given sample can differentiated. As can be seen in TABLE 6 and TABLE 7, when sample U4 is evaluated individually the amount of separation between concentrations is very high. Combined analysis of all urine samples together shows a reduction in separation between samples. However, despite the reduction in separation when analysis is combined, the 100 mI/mL and 200 mIU/mL spiked LH samples are still highly differentiable.

TABLE 6

| Spiked | U4 only | | | Separation (SD) | | |
|---|---|---|---|---|---|---|
| [LH] (mIU/mL) | Avg | Std Dev | Signal Diff | From Lower | From Higher | Combined |
| 0 | 828 | 36 | 114 | 3.2 | 3.2 | 1.6 |
| 2 | 942 | 36 | 296 | 8.3 | 8.3 | 4.1 |
| 5 | 1238 | 36 | 1105 | 30.8 | 13.1 | 9.2 |
| 15 | 2344 | 84 | 2040 | 24.2 | 15.1 | 9.3 |
| 40 | 4383 | 135 | 1799 | 13.4 | 7.4 | 4.8 |
| 70 | 6182 | 242 | 1282 | 5.3 | 5.5 | 2.7 |
| 100 | 7464 | 233 | 3310 | 14.2 | 4.7 | 3.5 |
| 200 | 10774 | 700 | 5282 | 7.5 | 17.4 | 5.3 |
| 1000 | 16056 | 303 | | | | |

TABLE 7

| Spiked | U1-U6 | | | Separation (SD) | | |
|---|---|---|---|---|---|---|
| [LH] (mIU/mL) | Avg | Std Dev | Signal Diff | From Lower | From Higher | Combined |
| 0 | 781 | 203 | 55 | 0.3 | 0.2 | 0.1 |
| 2 | 836 | 264 | 270 | 1.0 | 1.1 | 0.5 |
| 5 | 1106 | 252 | 778 | 3.1 | 2.0 | 1.2 |
| 15 | 1884 | 389 | 1564 | 4.0 | 1.7 | 1.2 |
| 40 | 3448 | 901 | 1424 | 1.6 | 1.3 | 0.7 |
| 70 | 4872 | 1108 | 1443 | 1.3 | 1.8 | 0.8 |
| 100 | 6315 | 791 | 3130 | 4.0 | 3.2 | 1.8 |
| 200 | 9445 | 974 | 6611 | 6.8 | 21.8 | 5.2 |
| 1000 | 16056 | 303 | | | | | d. Comparison to Quantification of LH Suspended in ELISA Standards

Figure 42:
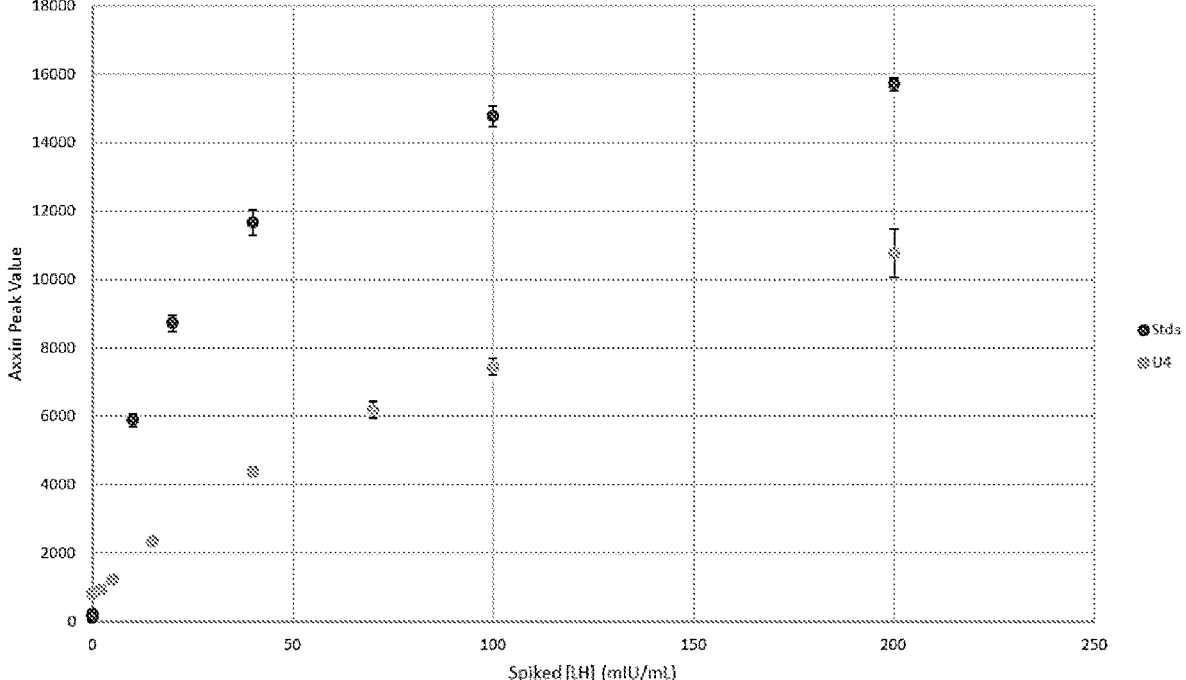
FIG. 42 shows a graph of lateral flow assay (LFA) strips run with ELISA standards vs. U4. Error bars represents standard deviation.
Figure 43:
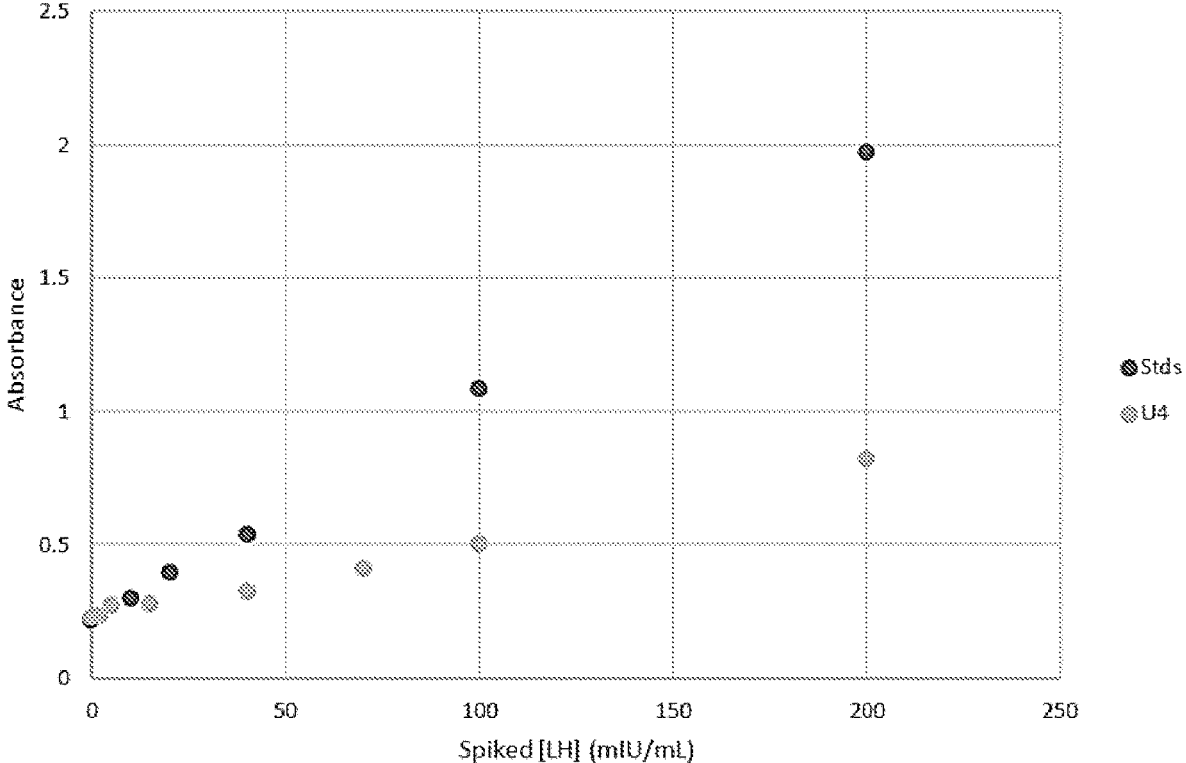
FIG. 43 shows a graph of ELISA results when run with ELISA standards vs. U4.

LH quantification with A/5 half-strips was repeated for DRG ELISA LH standards. As can be seen in FIG. 41, a monotonic increase in test line intensity was seen as the LH concentration of ELISA standards increased. Moreover, ELISA standards showed a stronger signal compared to urine samples spiked at nominally identical concentrations. An example of this can be seen in FIG. 42, which shows a comparison of the Axxin peak values measured in ELISA standards and U4 samples spiked with LH. A similar increase in signal intensity was seen when ELISA assays were run with either the ELISA standard samples or the spiked U4 samples, as shown in FIG. 43. Differences seen between ELISA standards and spiked urine samples can possible be attributed to the fact that ELISA standards used the 1st WHO standard antigen for LH, while spiked urine samples used the 3rd WHO antigen sample.

Example 6: Detection of PdG with a Developed Lateral Flow Cassette a. Cassette Assembly Pregnanediol glucuronide (PdG) is the major urine metabolite of progesterone and thus the detection of PdG can be used to monitor progesterone. To assess the ability of a developed lateral flow immunoassay (LFIA) to accurately detect PdG in urine, LFIA cassettes were prepared with the format described below in TABLE 8.

TABLE 8

| Cassette | MICA-200 |
|---|---|
| Backing card | 60 mm Kenosha |
| Membrane | 25 mm CN140 with 2 mg/mL PdG-BSA and 0.5 mg/mL goat anti-Mouse lines |
| Conjugate pad | 10 mm 8980 pad |
| Conjugate | Ab4-Au-8 @ OD4 with 0.5% casein + 10% sucrose + 5% trehalose, sprayed at |
| Sample pad | 14 mm Std 17 pad, with 8 μL of 1/3 concentration running buffer spotted and dried |
| Sample | 65 μL of urine | b. Samples

To evaluate the performance of developed LFIA cassettes, PdG concentration was measured in 20 female urine samples with both the developed LFIA cassettes and a standard ELISA assay. Female urine samples were numbered F1-F20. Male urine aliquots, (which do not contain PdG) spiked with known concentrations of PdG, were used as standards to generate the standard curve of the developed LFIA cassettes. Aliquots were prepared with PdG concentrations of 0, 0.156, 0.313, 0.625, 1.25, 2.5, and 5 μg/mL.

c. ELISA Measurements

ELISA assays were performed on samples F1-F20 using the Cayman Chemical pregnanediol-3-glucuronide (PdG) ELISA kit, which is sensitive at a range of 0.4 ng/mL to 50 ng/mL. ELISA plates were read at 405 nm. Tested urine samples were diluted at factors of 50 and 250 prior to performing ELISA assays. Samples were run in triplicate (n=3). TABLES 9-10 show the setup of ELISA plates and measured absorbance values. The wells S1-S8 represent the standards provided by the manufacturer and were used to generate a standard curve.

To generate the standard curve the absorbance value of the non-specific binding control (NSB) well was subtracted from the absorbance value of each of wells S1-S8 to generate subtracted standard values. Separately, the absorbance value of the NSB well was subtracted from the absorbance value of well B0, which represented maximum binding to generate an adjusted maximum binding level. The subtracted standard values were then divided by the adjusted maximum binding levels to generate normalized standard values. Normalized standard values were then converted via a logit transformation and plotted vs. the PdG concentrations to produce the standard curve.

Using the generated standard curve, the concentration of PdG in each of samples F1-F20 was determined, taking into account the dilution factors used. TABLE 11 shows the PdG concentrations for each sample of female urine assessed as calculated using the results of ELISA assays and the generated standard curves. The right most column of TABLE 11 shows the amount by which the highest sample is higher than the lowest values as a percentage of the lower concentration. For example a value of 50% in this column indicates that the highest calculated value is 50% greater than the lowest calculated value.

TABLE 9

Plate layout of PdG ELISA Plate 1

| | 1 | 2/3 | 4/5/6 | 7/8/9 | 10/11/12 |
|---|---|---|---|---|---|
| A | Blank | S1 | F1, 50 | F5, 50 | F9, 50 |
| B | | S2 | F1, 250 | F5, 250 | F9, 250 |
| C | NSB | S3 | F2, 50 | F6, 50 | F10, 50 |
| D | | S4 | F2, 250 | F6, 250 | F10, 250 |
| E | B0 | S5 | F3, 50 | F7, 50 | F11, 50 |
| F | | S6 | F3, 250 | F7, 250 | F12, 50 |
| G | Total | S7 | F4, 50 | F8, 50 | F11, 250 |
| H | Activity | S8 | F4, 250 | F8, 250 | F12, 250 |

TABLE 10

Absorbance values of PdG ELISA Plate 1

| | 1 | 2 | 3 | 4 | 5 | 6 | 7 | 8 | 9 | 10 | 11 | 12 |
|---|---|---|---|---|---|---|---|---|---|---|---|---|
| A | 0.11 | 0.22 | 0.22 | 0.17 | 0.18 | 0.18 | 0.26 | 0.27 | 0.27 | 0.59 | 0.63 | 0.60 |
| B | 0.10 | 0.33 | 0.32 | 0.37 | 0.38 | 0.38 | 0.57 | 0.65 | 0.60 | 0.98 | 1.02 | 0.91 |
| C | 0.10 | 0.46 | 0.46 | 0.25 | 0.25 | 0.25 | 0.15 | 0.15 | 0.14 | 0.22 | 0.22 | 0.21 |
| D | 0.10 | 0.60 | 0.59 | 0.55 | 0.55 | 0.52 | 0.26 | 0.27 | 0.27 | 0.47 | 0.49 | 0.47 |
| E | 1.27 | 0.76 | 0.75 | 0.21 | 0.22 | 0.21 | 0.79 | 0.76 | 0.81 | 0.66 | 0.72 | 0.68 |
| F | 1.23 | 0.85 | 0.92 | 0.46 | 0.45 | 0.43 | 1.12 | 1.09 | 1.10 | 0.58 | 0.58 | 0.59 |
| G | 0.28 | 0.94 | 1.03 | 0.24 | 0.24 | 0.24 | 0.92 | 1.00 | 0.97 | 0.97 | 1.00 | 1.04 |
| H | 0.27 | 1.02 | 1.01 | 0.49 | 0.53 | 0.52 | 1.11 | 1.18 | 1.16 | 0.92 | 0.97 | 0.92 |

TABLE 11

Calculated concentrations of PdG from female urine samples

| Sample | Avg. calculated value (ng/mL) | DF = 50 | DF = 250 | DF = 50 | DF = 250 | Max percent above min (max/min − 1) |
|---|---|---|---|---|---|---|
| F1 | 6401 | 6617 | 4463 | 8902 | 5623 | 99% |
| F2 | 2294 | 2358 | 1790 | 2687 | 2339 | 50% |
| F3 | 3289 | 3707 | 2871 | — | — | 29% |
| F4 | 2371 | 2685 | 2056 | — | — | 31% |
| F5 | 1664 | 2024 | 1304 | — | — | 55% |
| F6 | 11620 | 13209 | 10030 | — | — | 32% |
| F7 | 91 | 112 | 70 | — | — | 59% |
| F8 | 39 | 42 | 36 | — | — | 16% |
| F9 | 231 | 262 | 201 | — | — | 30% |
| F10 | 3041 | 3606 | 2476 | — | — | 46% |
| F11 | 167 | 179 | 160 | 180 | 149 | 21% |
| F12 | 260 | 288 | 250 | 275 | 225 | 28% |
| F13 | 2444 | 2752 | 2137 | — | — | 29% |
| F14 | 303 | 296 | 310 | — | — | 5% |
| F15 | 3938 | 4672 | 3204 | — | — | 46% |
| F16 | 2949 | 3438 | 2460 | — | — | 40% |
| F17 | 3900 | 4721 | 3079 | — | — | 53% |
| F18 | 661 | 673 | 649 | — | — | 4% |
| F19 | 841 | 946 | 735 | — | — | 29% |
| F20 | 3846 | 4642 | 3050 | — | — | 52% |

DF = Dilution Factor d. LFIA Measurements

Aliquots of male urine spiked with 0, 0.156, 0.313, 0.625, 1.25, 2.5, or 5 g/mL PdG were used to generate a standard curve with the developed LFIA cassettes. 65 μL of urine samples were pipetted into the sample ports, and cassettes were read approximately 15 minutes later on an Axxin reader. Each spiked male urine sample was run in duplicate. Axxin generated values and images used to generate the standard curve are shown in FIG. 44. The calculated standard curve that resulted from these values was y=−2355*ln (x)=5796; where x represents the PdG concentration in g/mL and y represents the Axxin value.

Figure 46:
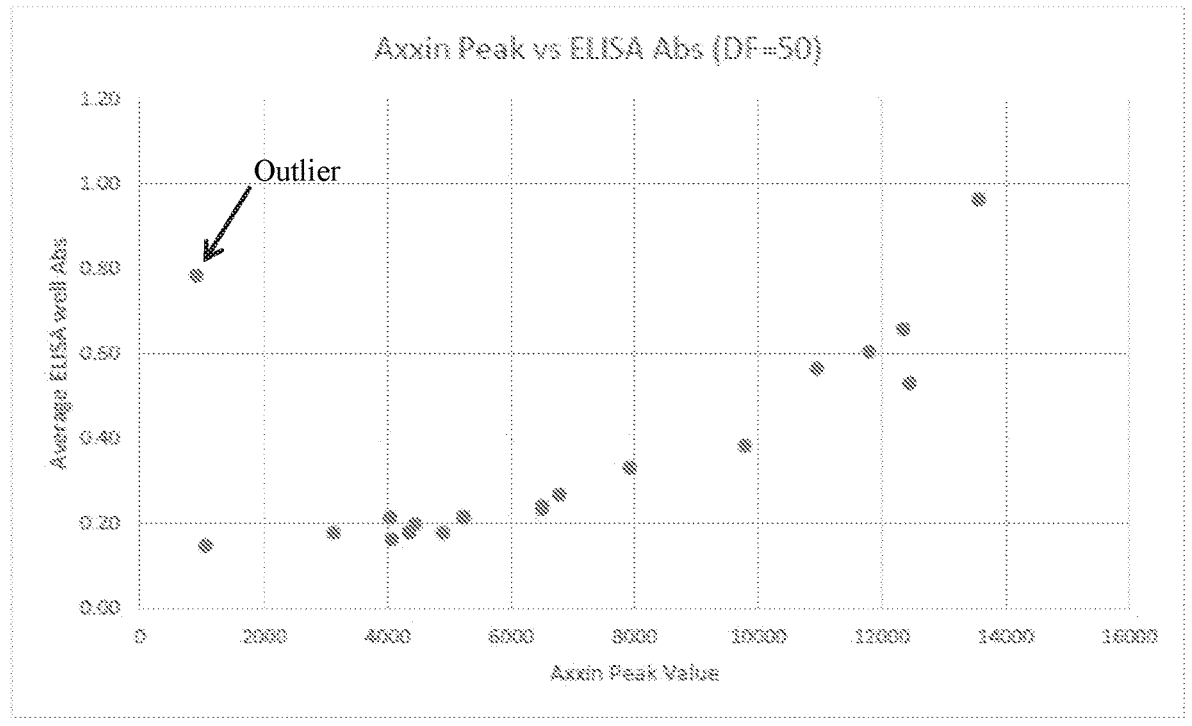
FIG. 46 shows a direct comparison of ELISA absorbance vs. Axxin peak values with samples run with a dilution factor of 50.
Figure 47:
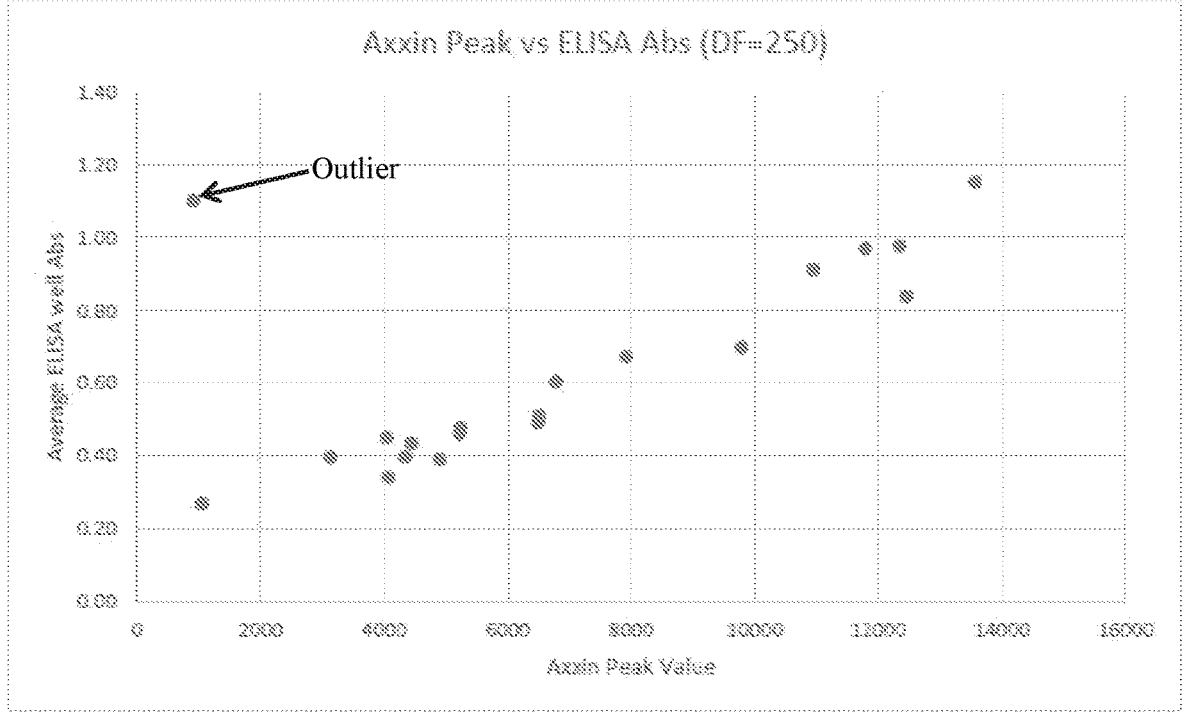
FIG. 47 shows a direct comparison of ELISA absorbance vs. Axxin peak values with samples run with a dilution factor of 250.

Female urine samples F1-F20 were run on LFIA cassettes with n=4 replicates. Axxin-generated values and images of cassettes run with samples F1-F20 are shown in FIG. 45. TABLE 12 and FIG. 46 show a comparison of ELISA absorbance values and Axxin-generated peak values measured from LFIA cassettes. When compared to ELISA absorbance values, values obtained from Axxin readings compared in a consistent manner with the exception of a single outlier. A similar result was seen when performing the analysis using the 250× dilution factor ELISA absorbance data as shown by FIG. 47 and TABLE 13.

TABLE 12

Comparison of ELISA absorbance and Axxin values (ELISA dilution factor = 50)

| Sample | Axxin | Absorbance in ELISA | Sample | Axxin | Absorbance in ELISA (50 DF) |
|---|---|---|---|---|---|
| 1 | 4068 | 0.16 | 11 | 12348 | 0.66 |
| 2 | 6490 | 0.23 | 12 | 10943 | 0.56 |
| 3 | 4040 | 0.21 | 13 | 5220 | 0.21 |
| 4 | 6498 | 0.24 | 14 | 12453 | 0.53 |
| 5 | 6775 | 0.27 | 15 | 4895 | 0.18 |
| 6 | 1045 | 0.15 | 16 | 4445 | 0.20 |
| 7 | 905 | 0.78 | 17 | 3130 | 0.18 |
| 8 | 13568 | 0.96 | 18 | 9779 | 0.38 |
| 9 | 11790 | 0.60 | 19 | 7920 | 0.33 |
| 10 | 5233 | 0.21 | 20 | 4343 | 0.18 |

DF = Dilution factor

TABLE 13

Comparison of ELISA absorbance and Axxin values (ELISA dilution factor = 250)

| Sample | Axxin | Abs in ELISA | Sample | Axxin | Absorbance in ELISA (250DF) |
|---|---|---|---|---|---|
| 1 | 4068 | 0.34 | 11 | 12348 | 0.98 |
| 2 | 6490 | 0.49 | 12 | 10943 | 0.91 |
| 3 | 4040 | 0.45 | 13 | 5220 | 0.46 |
| 4 | 6498 | 0.51 | 14 | 12453 | 0.84 |
| 5 | 6775 | 0.60 | 15 | 4895 | 0.39 |
| 6 | 1045 | 0.27 | 16 | 4445 | 0.43 |
| 7 | 905 | 1.10 | 17 | 3130 | 0.40 |
| 8 | 13568 | 1.15 | 18 | 9779 | 0.70 |
| 9 | 11790 | 0.97 | 19 | 7920 | 0.67 |
| 10 | 5233 | 0.48 | 20 | 4343 | 0.40 |

DF = Dilution factor

Figure 48:
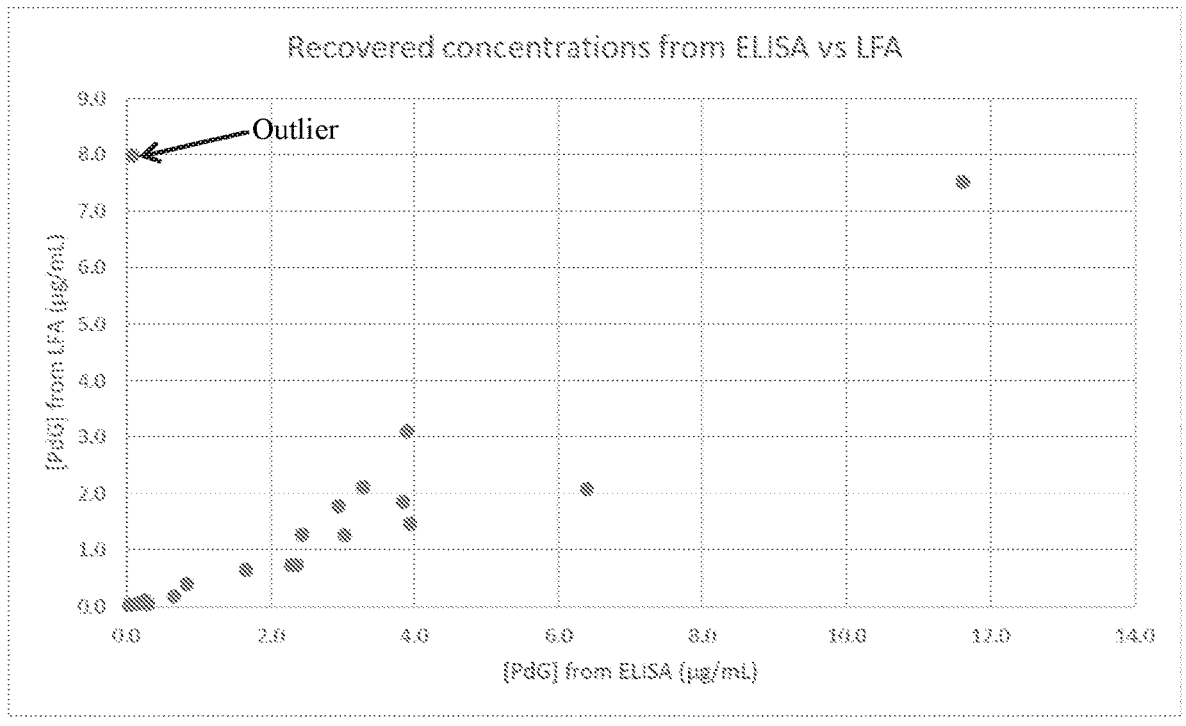
FIG. 48 shows a graph illustrating a comparison of calculated pregnanediol glucuronide (PdG) concentrations from ELISA and the lateral flow assay (LFA).
Figure 49:
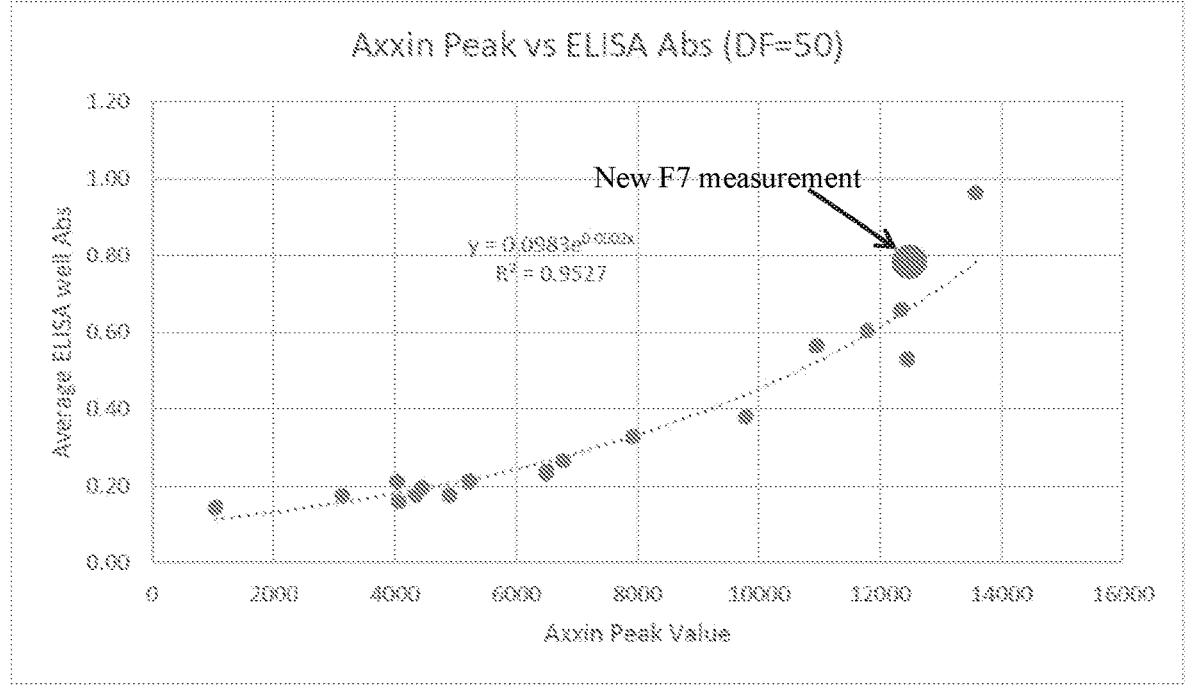
FIG. 49 shows a direct comparison of Axxin and ELISA values (dilution factor=50) with the rerun F7 sample replacing the previously run F7 data point.
Figure 50:
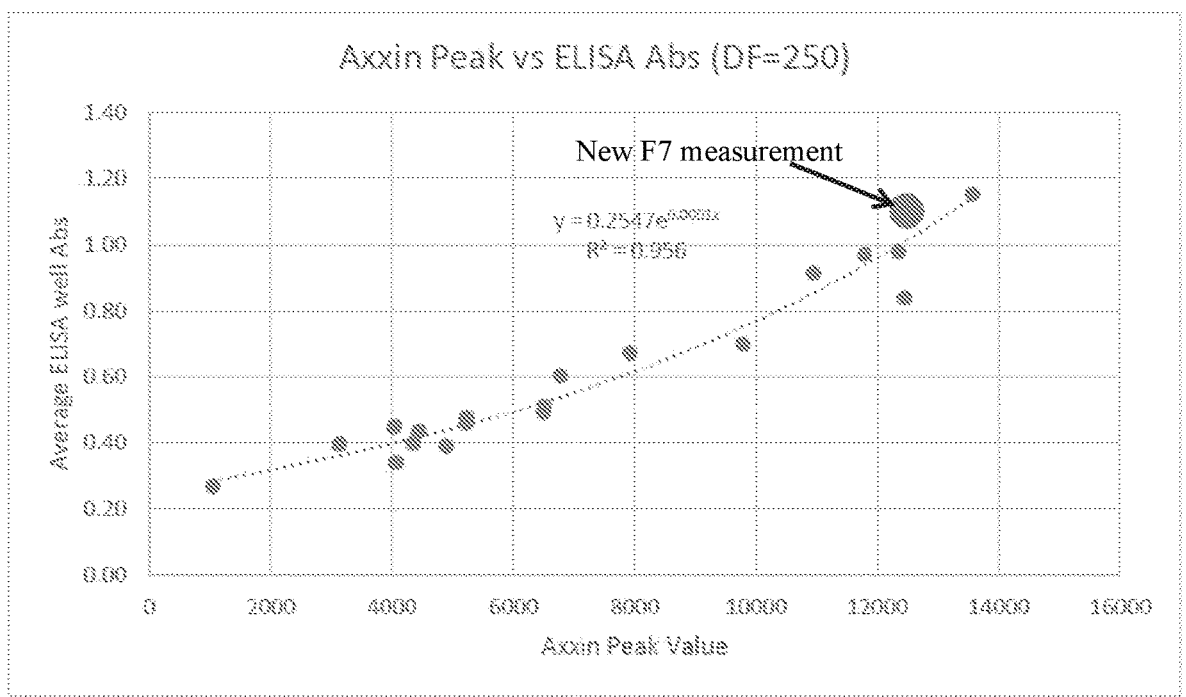
FIG. 50 shows a direct comparison of Axxin and ELISA values (dilution factor=250) with the rerun F7 sample replacing the previously run F7 data point.
Figure 51:
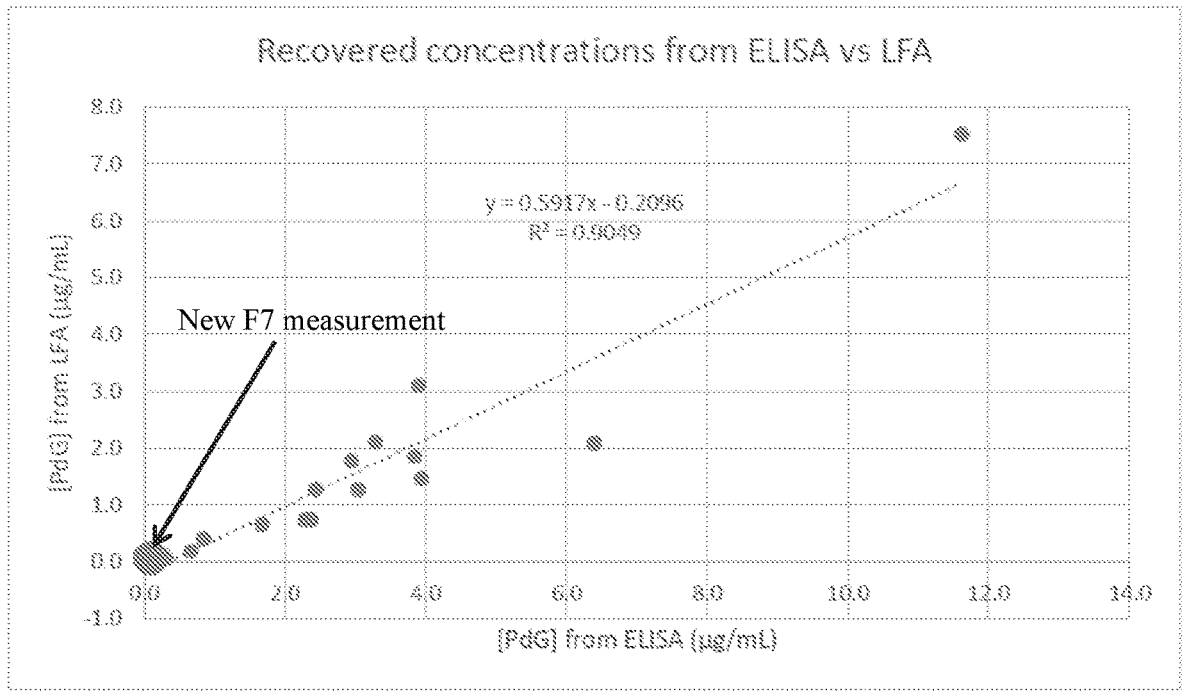
FIG. 51 shows a graph illustrating a comparison of calculated PdG concentrations from ELISA and the lateral flow assay (LFA) with the rerun F7 sample replacing the previously run F7 data point.

A comparison of PdG concentrations calculated (also called recovered concentrations) for each sample using ELISA and LFIA cassettes is shown in TABLE 14 and FIG. 48. As was the case when comparing absorbance values, an outlier can be seen in the upper left hand portion of the graph representing sample F7. Due to the possibility that this outlier was the result of human error (e.g. the wrong sample was pipetted into the sample well), this sample was re-run and the results analyzed. As can be seen in FIGS. 49-51, repeating the measurements of sample F7 and replacing the originally measured values with the newly measured values results in an improved correlation with ELISA results for plots comparing Axxin values to ELISA absorbance values and for plots comparing PdG concentrations calculated via ELISA or the LFIA.

TABLE 14

Comparison of calculated concentrations in ELISA and LFIA

| Sample | Recovered PdG concentrations (μg/mL) | |
|---|---|---|
| | ELISA | LFA |
| F1 | 6.4 | 2.1 |
| F2 | 2.3 | 0.7 |
| F3 | 3.3 | 2.1 |
| F4 | 2.4 | 0.7 |
| F5 | 1.7 | 0.7 |
| F6 | 11.6 | 7.5 |
| F7 | 0.1 | 8.0 |
| F8 | 0.0 | 0.0 |
| F9 | 0.2 | 0.1 |
| F10 | 3.0 | 1.3 |
| F11 | 0.2 | 0.1 |
| F12 | 0.3 | 0.1 |
| F13 | 2.4 | 1.3 |
| F14 | 0.3 | 0.1 |
| F15 | 3.9 | 1.5 |
| F16 | 2.9 | 1.8 |
| F17 | 3.9 | 3.1 |
| F18 | 0.7 | 0.2 |
| F19 | 0.8 | 0.4 |
| F20 | 3.8 | 1.9 |

Example 7: Optimization and Testing of LH/PdG Dual Measurement Cassettes a. Optimization of Gold and Test Line Antibody for LH Detection To determine the locally optimal concentrations of gold and test line antibody to use for the LH assay in the LH/PdG format the materials and equipment listed below in TABLE 15 were used.

TABLE 15

Assay components

Membrane: CN140 membrane with PdG-BSA@2 mg/mL
and Goat anti-Mouse@0.5 mg/mL and anti-LH
C083 wick pad, Millipore, CFSP223000
Blank 8980 conjugate pad
Std 17 sample pads
60 mm backing card, MIBA-20

Reagents

Conjugate diluent: 2% casein + 40% sucrose + 20%
Running buffer: 0.5M Tris + 0.5% Tween-20 + 0.5% casein
αLH gold conjugates (anti-LH alpha subunit);
loading = 20 μg/(mL*OD)
αPdG gold conjugates (anti-LH alpha subunit);
loading = 8 μg/(mL*OD)
Urine sample U7
Urine 7 spiked with 100 μg/mL PdG
Urine 7 spiked with 800 mIU/mL LH TABLE 15-continued DI Water (>18.0 MΩ)

Equipment 96-well plates (flat bottom, cloudy polypropylene)
Kinematic cutter
Pipettes After removing samples form the freezer various concentrations of LH-conjugates were spot dried onto lateral flow assay set-ups. To assemble set-ups 5 mm wide strips were prepared with a blank conjugate pad and a Std 17 sample pad. Strips were flexed to separate the sample/conjugate pads and 5 μL of diluted conjugate was added to the conjugate pad, ensuring that no conjugate touched the nitrocellulose membrane or the sample pad. A backing slit from a backing card was then added to separate the conjugate pad from the membrane while it dried for 10 minutes at 40° C. After drying, 8 μL of running buffer was added to the sample well. Strips were subsequently dried for an additional 5 minutes at 40° C.

To test the effect of various gold and test line antibody concentrations 65 μL of urine with no LH or PdG, or urine spiked LH and PdG concentrations of 100 mIU/mL and 1.25 μg/mL respectively, were added to the strip (the strip was loaded into a cassette). Fifteen minutes after sample loading strips were read to determine the Aaxin peak value of LH test lines (TL). Results of this assay are shown in FIG. 52. Results indicated that nonspecific TL signal increases somewhat with higher OD gold, and also increase with positive samples from OD4 to OD12. For relatively large increases in amounts (e.g. doubling or tripling antibody use), small gains are made. For example, tripling the LH gold amount from OD4 to OD12 increases the 1 mg/mL condition's LH peak height only from 3440 to 3920. One important factor that is not apparent in FIG. 52 is the background color with higher gold OD conditions. Results showed that the OD8 and OD12 conditions had increasingly poor conjugate clearance, indicating that significant amounts of gold conjugate remained in the middle of the membrane at read time.

Figure 54:
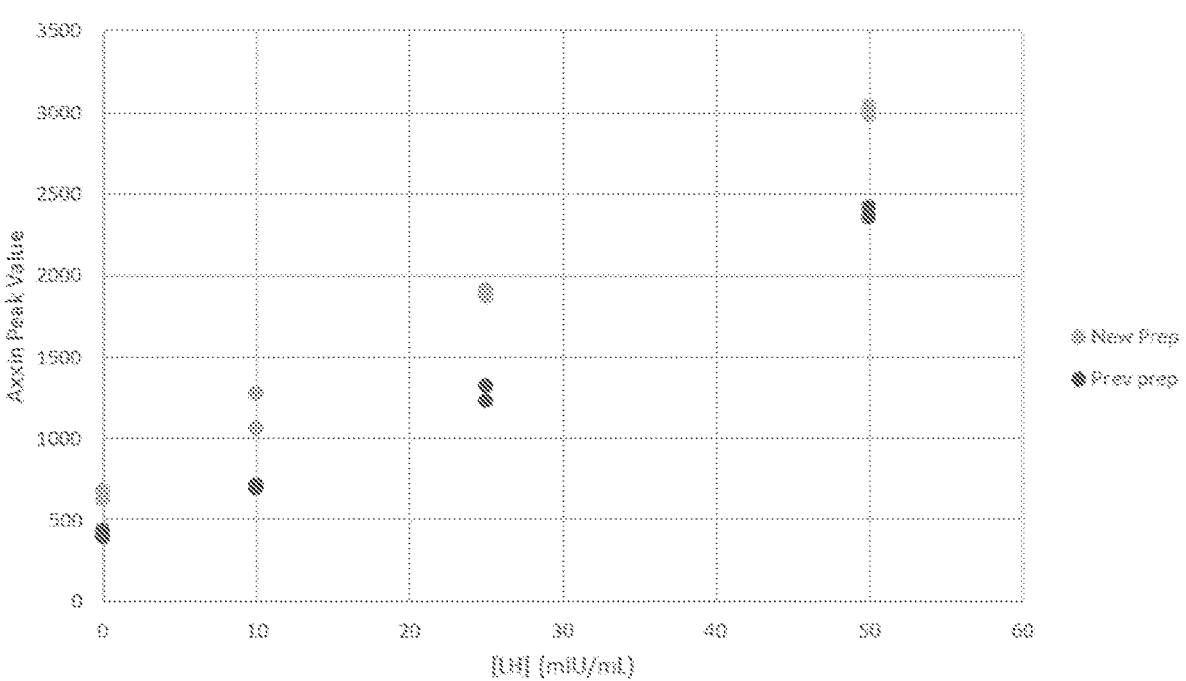
FIG. 54 shows a comparison of two different conjugate mixtures run with samples spiked with varying amounts of LH.

To more fully explore the detection of low concentration LH-spike samples the experiment described in the preceding paragraphs was slightly modified and repeated with new LH and PdG conjugate preparations. The tested LH concentrations for the slightly modified repeat were 0, 10, 25, and 50 mIU/mL. In the modified repeat experiment an extra wash step was added after the addition of 65 μL urine to the strip. The extra wash step was performed by adding 65 μL of running buffer 10 minutes after urine addition. Strips were read 10 minutes after the additional wash step. As shown FIG. 53 and FIG. 54, results obtained with the new conjugate preparation showed a similar overall pattern with higher peak values at every concentration when compared to those obtained with old conjugate preparation.

b. Variations on Duplex Assay Procedure and Amounts

Variations in gold concentration, sample volume, running buffer, and read time were explored to select ideal conditions for measuring both LH and PdG. Materials and equipment used in these experiments are shown below in TABLE 16.

TABLE 16

Assay components

Membrane: CN140 membrane with PdG-BSA@2 mg/mL and Goat
anti-Mouse@0.5 mg/mL and anti-LH antibody@2 mg/ml
C083 wick pad, Millipore, CFSP223000

TABLE 16-continued

| Blank 8980 conjugate pad |
| Std 17 sample pads |
| 60mm backing card, MIBA-20 |
| Reagents |

Conjugate diluent: 2% casein + 40% sucrose + 20% trehalose
Running buffer (RB): 0.5M Tris + 0.5% Tween-20 + 0.5% casein
αLH gold conjugates (anti-LH alpha subunit); loading =
201 g/(mL*OD)
αPdG gold conjugates (anti-LH alpha subunit); loading =
81 g/(mL*OD)
Urine sample U7, donated from DCN
PdG at 10 mg/mL in methanol
LH at 33 IU/mL in water
Urine 7 spiked with 1001 g/mL PdG
Urine 7 spiked with 800 mIU/mL LH
DI Water (>18.0 MQ)
Equipment 96-well plates (flat bottom, cloudy polypropylene)
Kinematic cutter
Pipettes Experiments were performed with the following method:
1. Pull samples from refrigerator/freezer
2. Gold conjugate prep

TABLE 17

| Parameter | Vol 350 | | | |
| | Sugars/Casein | LH | PdG | Water |
| --- | --- | --- | --- | --- |
| Type | Conc | Conc | Conc | Remainder |
| Final | 0.5% | OD 5* | OD 3* | — |
| Init | 2% | OD 26.4 | OD 25.5 | — |
| Vol (μL) | 87.5 | 66.3 | 41.2 | 155.0 |

*For naming purposed only, not actual concentrations

3. Sample prep

TABLE 18

| Total Vol | Final conc | 25 |
| --- | --- | --- |
| 1000 | Init conc | 800 |
| | Vol to add | 31.25 |
| | Vol neg to add | 968.75 |

4. Conjugate spotting conditions
   a. Full conc conjugate=nominal OD5/OD3 mixture from TABLE 17 above
   b. ½ conc conjugate=50% mixture from TABLE 17 above+50% diluted sugar/casein solution
   c. ⅓ conc conjugate=33% mixture from TABLE 17 above+66.7% diluted sugar/casein solution
   d. Note: diluted sugar/casein solution is at the standard final concentration, so sugars/casein content is same for all conditions
5. Spotted RB prep
   a. RB-only=8 μL RB spotted directly in sample well
   b. RB/CD=8 μL of 50/50 mixture of RB and conjugate diluent spotted in sample well
   c. CD-only=8 μL of conjugate diluent spotted in sample well
   d. RB/CD double=16 μL total of 50/50 mixture spotted in sample well
6. Spotting/drying conjugates
   a. Prepare 5 mm width strips with blank conjugate pad and Std 17 sample pad
   b. Flex strip to separate sample/conjugate pads
   c. Add 5 μL of diluted conjugate to conjugate pad, ensuring no conjugate touches either the nitrocellulose membrane or the sample pad d. Add a backing slit from a backing card to separate the conjugate pad from the membrane while it dries 10 min at 40° C.
   e. After dried, add 8 μL of RB to sample well then dry 5 min at 40° C.
7. Running procedure (basic procedure, modifications described FIG. 55)
   a. Add urine sample to strip
   b. Read at read time
Results to the experiment described in the preceding paragraph are shown in FIG. 55. To summarize:
   Full vs ½ vs ⅓ conjugate: the ½ and ⅓ both had superior results compared to the full conjugate amounts, especially in regards to background clearance and LH line clarity E—choose the ⅓ conjugate condition
   Spotted running buffer (look at the ⅓ conjugate condition): pure running buffer had better performance than the other conditions←choose the RB-only spotting condition
   30 min vs 15 min: signals went from approximately 450 for negative, 1500 for positive up to 550 for negative, 2000 for positive E—not worth the extra time, but it is good to note in case extra sensitivity is required later
   Wash: a definite improvement for the Full conjugate condition, but this makes the testing procedure much worse overall←not necessary; exclude
   Urine Volume: No benefit was observed going from 80 μL to 100 μL←stay with 804 μL
   c. Gold Conjugate Amounts for LH and PdG
   Purpose: given that many assay parameters have been set (LH test line antibody concentration, RB spotting, urine volume, assay time), this experiment aims at finalizing the different gold concentrations. To finalize different gold concentrations the materials and equipment shown below in TABLE 18 was used.

TABLE 18

| Assay components |
| --- |

Membrane: CN140 membrane with PdG-BSA@2 mg/mL and Goat
anti-Mouse@0.5 mg/mL and anti-LH antibody@2 mg/mL
C083 wick pad, Millipore, CFSP223000
Blank 8980 conjugate pad
Std 17 sample pads
60 mm backing card, MIBA-20
Reagents Conjugate diluent: 2% casein + 40% sucrose + 20% trehalose
RB: 0.5M Tris + 0.5% Tween-20 + 0.5% casein
αLH gold conjugates (anti-LH alpha subunit); loading =
201 g/(mL*OD); concentrated additionally
αPdG gold conjugates (anti-LH alpha subunit); loading =
81 g/(mL*OD); concentrated additionally
Urine sample U7, donated from DCN
PdG at 10 mg/mL in methanol
LH at 33 IU/mL in water
Urine 7 spiked with 1001 g/mL PdG
Urine 7 spiked with 800 mIU/mL LH
DI Water
Equipment 96-well plates (flat bottom, cloudy polypropylene)
Kinematic cutter
Pipettes Using the materials and equipment listed in TABLE 18 above the following experimental methods were performed:
1. Pull samples from refrigerator/freezer
2. Gold conjugate prep (details can be seen in FIG. 56)
3. Sample prep

TABLE 19

|  | Conc 1 | Conc 2 | Conc 3 |
|---|---|---|---|
| vol to prep (µL) | 200 | 200 | 200 |
| final conc (mIU/mL) | 0 | 10 | 25 |
| init conc (mIU/mL) | 100 | 100 | 100 |
| vol to add (µL) | 0 | 20 | 50 |
| vol neg (µL) | 200 | 180 | 150 |

4. Conjugate spotting conditions
   a. Full conc conjugate=nominal OD5/OD3 mixture from TABLE 17 above
   b. ½ conc conjugate=50% mixture from TABLE 17 above+50% diluted sugar/casein solution
   c. ⅓ conc conjugate=33% mixture from TABLE 17 above+66.7% diluted sugar/casein solution
   d. Note: diluted sugar/casein solution is at the standard final concentration, so sugars/casein content is same for all conditions
5. Spotted 8 µL RB spotted directly in sample well
6. Spotting/drying conjugates
   a. Prepare 5 mm width strips with blank conjugate pad and Std 17 sample pad
   b. Flex strip to separate sample/conjugate pads
   c. Add 5 µL of diluted conjugate to conjugate pad, ensuring no conjugate touches either the nitrocellulose membrane or the sample pad
   d. Add a backing slit from a backing card to separate the conjugate pad from the membrane while it dries 10 min at 40° C.
   e. After dried, add 8 µL of RB to sample well then dry 5 min at 40° C.
7. Running procedure (basic procedure, modifications described in FIG. 57)
   a. Add 80 µL of urine sample to strip
   b. Read at read time Results to the experiments described in the preceding paragraph are shown in FIG. 57. To summarize, the lower amount of gold produced nearly the same levels of test line binding, but the conjugate clearance was superior with the lower gold condition. In terms of read time, there is little difference between 20 min and 30 min, but there is a significant jump in signal between 10 min and 20 min.

d. New PdG Conjugates Mixed at Final Ratio with LH Gold Conjugate and Tested on PdG-Only Membranes A new preparation of PdG gold (Ab4-Au-8) was made in preparation for the scale up of conjugate pads. To determine that the previously used Ab4-Au-8 conjugates behaved similarly to the newly prepared conjugates the following experiment was performed using the reagents and equipment shown in TABLE 20 below.

TABLE 20

| Assay components |
|---|
| Membrane: CN140 membrane with PdG-BSA@2 mg/mL and Goat anti-Mouse@0.5 mg/ml |
| C083 wick pad, Millipore, CFSP223000 |
| Blank 8980 conjugate pad |
| Std 17 sample pads |
| 60mm backing card, MIBA-20 |
| Reagents |
| Conjugate diluent: 2% casein + 40% sucrose + 20% |
| RB: 0.5M Tris + 0.5% Tween-20 + 0.5% casein |
| αLH gold conjugates (anti-LH alpha subunit); |
| loading = 20 µg/(mL*OD); concentrated |
| αPdG gold conjugates (anti-LH alpha subunit); |

TABLE 20-continued

| loading = 8 µg/(mL*OD); concentrated |
|---|
| αPdG gold conjugates (anti-LH alpha subunit); |
| loading = 8 µg/(mL*OD); new conjugation |
| Urine sample U7, donated from DCN |
| PdG at 10 mg/mL in methanol |
| Urine 7 spiked with 100 µg/mL PdG |
| DI Water |
| Equipment |
| 96-well plates (flat bottom, cloudy polypropylene |
| Kinematic cutter |
| Pipettes |

Using the materials and equipment listed in TABLE 20 above the following experimental methods were performed:
1. Pull samples from refrigerator/freezer
2. Gold conjugate prep (details can be seen in FIG. 58)
3. Sample prep

|  | Conc 1 | Conc 2 | Conc 3 | Conc 4 |
|---|---|---|---|---|
| vol to prep (i. tL) | 100 | 100 | 100 | 100 |
| final conc | 0 | 1 | 2 | 4 |
| init conc | 100 | 100 | 100 | 100 |
| vol to add (i. tL) | 0 | 1 | 2 | 4 |
| vol neg (i. tL) | 100 | 99 | 98 | 96 |

4. Spotting/drying conjugates
   a. Prepare 5 mm width strips with blank conjugate pad and Std 17 sample pad
   b. Flex strip to separate sample/conjugate pads
   c. Add 5 µL of diluted conjugate to conjugate pad, ensuring no conjugate touches either the nitrocellulose membrane or the sample pad
   d. Add a backing slit from a backing card to separate the conjugate pad from the membrane while it dries 10 min at 40° C.
   e. After dried, add 8 µL of RB to sample well then dry 5 min at 40° C.
5. Running procedure (basic procedure, modifications described in FIG. 59)
   a. Add 80 µL urine to strip
   b. Read at 15 minutes Results showed that the newer PdG gold conjugates showed more sensitivity to PdG compared to the previous conjugates, as can be seen in FIG. 59.

e. LH Measurement of Spiked Male and Unspiked Female Sample Panels

Purpose: To test two sets of urine samples in an LH-measuring ELISA.
1. Seven male urine samples spiked with (0, 25, 100) mIU/mL LH
2. Twenty female urine samples with unknown LH content The materials and equipment used are shown in TABLE 21 below:

TABLE 21

| Assay components |
|---|
| DRG ELISA for measuring LH, cat EIA 1290 |
| Reagents |
| Male urine samples from Lee Biosolutions (labeled U1-U3) |
| Male urine samples donated from DCN (labeled U4-U7) |
| Female urine samples from Lee Biosolutions (labeled F1-F20) |
| LH at 33 IU/mL in water, stored at −20° C. |

TABLE 21-continued

| DI Water (>18.0 MΩ) |
| --- |
| Equipment |
| 96-well plates (flat bottom, cloudy polypropylene) |
| Kinematic cutter |
| Pipettes |

Using the materials in the preceding paragraph the following experimental methods were performed:

1. Pull materials from storage
   a. Thaw all urine samples
   b. Thaw LH aliquot
   c. Bring DRG ELISA to room temperature
2. ELISA procedure
   a. Bring reagents to room temperature
   b. Add 25 µL of each Standard, control, and sample to the appropriate wells
   c. Add 100 µL of Enzyme Conjugate into each well
   d. Thoroughly mix wells for 10 sec
   e. Incubate for 30 min at RT
   f. Briskly shake out contents of the wells
   g. Rinse 5× with DI Water (300 µL per well); strike plate sharply onto absorbent paper towels to collect retained solutions
   h. Add 100 µL of Substrate Solution to all wells
   i. Incubate 10 min at RT
   j. Stop the enzymatic reaction by adding 50 µL of Stop Solution to each well
   k. Read A450<--within 10 mins of adding the Stop Solution preferably
3. Samples.
   a. Female samples run unspiked
   b. Male samples will be run unspiked and spiked with (25 and 100) mIU/mL LH
   c. All samples run in triplicate ATTN. CWU: Shading has been verified to be removed
4. Layouts—for the plate layout of this experiment see TABLE 22 below

TABLE 22

| | 1 | 2 | 3 | 4 | 5 | 6 | 7 | 8 | 9 | 10 | 11 | 12 |
| --- | --- | --- | --- | --- | --- | --- | --- | --- | --- | --- | --- | --- |
| Plate A | | | | | | | | | | | | |
| A | Std 0 | | | | U1-0 | | | U1-25 | | | U1-100 | |
| B | Std 1 | | | | U2-0 | | | U2-25 | | | U2-100 | |
| C | Std 2 | | | | U3-0 | | | U3-25 | | | U3-100 | |
| D | Std 3 | | | | U4-0 | | | U4-25 | | | U4-100 | |
| E | Std 4 | | | | U5-0 | | | U5-25 | | | U5-100 | |
| F | Std 5 | | | | U6-0 | | | U6-25 | | | U6-100 | |
| G | Std 2 (from other plate) | | | | U7-0 | | | U7-25 | | | U7-100 | |
| H | Std 4 (from other plate) | | | | F1 | | | F2 | | | F3 | |
| Plate B | | | | | | | | | | | | |
| A | Std 0 | | | | F1 | | | F9 | | | F17 | |
| B | Std 1 | | | | F2 | | | F10 | | | F18 | |
| C | Std 2 | | | | F3 | | | F11 | | | F19 | |
| D | Std 3 | | | | F4 | | | F12 | | | F20 | |
| E | Std 4 | | | | F5 | | | F13 | | | U7-0 | |
| F | Std 5 | | | | F6 | | | F14 | | | U7-25 | |
| G | Std 2 (from other plate) | | | | F7 | | | F15 | | | U7-100 | |
| H | Std 4 (from other plate) | | | | F8 | | | F16 | | | U7-200 | |

5. Sample prep details are shown below in TABLE 23:

TABLE 23

| For each spiked male sample: | | | | |
| --- | --- | --- | --- | --- |
| Num wells | 3 | | | |
| Vol per well | 25 | | | |
| Padding | 0.15 | | | |
| To make (µL) | | | | |
| To make (µL) | 100 | 100 | 300 | 660 |
| Final Conc | 0 | 25 | 100 | 200 |
| Init conc (mIU/mL) | 100 | 100 | 200 | 33000 |
| Vol to add (µL) | 0 | 25 | 150 | 4 |
| Vol neg (µL) | 100 | 75 | 150 | 656 |

Results can be seen in FIG. 60 and FIG. 61. To summarize, there was is a mismatch between the standard curve data and the spiked urine samples. Even the highest absorbance value for a 100 mIU/mL sample was lower than the first positive standard (10 mIU/mL). The female samples in the bottom row were also below the lowest positive standard. There were no major outliers among the replicates. According to absorbance data, there was no sample with LH at 10 mIU/mL or above, including the ale urine spiked with 200 mIU/mL LH. However, there were relative differences between samples, with up to a 3× difference in absorbance between the min and max wells. There are no major outliers among the replicates.

The data obtained in this experiment was compared to absorbance data obtained from an earlier run experiment with different urine samples. In this earlier experiment there was a clear and definite dose response seen in male urine samples from spiked LH. Additionally, actual urine samples show up as significantly lower than the corresponding standard; for example, Urine C when spiked at 200 mIU/mL showed an average absorbance of about 0.35, which is close to the absorbance value of Standard 3, which is supposed to represent 40 mIU/mL LH. Finally, The maximum absorbance value (for Std 5) is ~1.0 absorbance units lower in this plate compared to the other plates; meanwhile, the minimum signal level is about the same; it is unknown whether simple settings in the ELISA reader may contribute to these differences, or whether this is primarily due to the lot. The plate set up and data from this earlier run experiment can be seen in FIG. 62, and FIG. 63, respectively.

Figure 64:
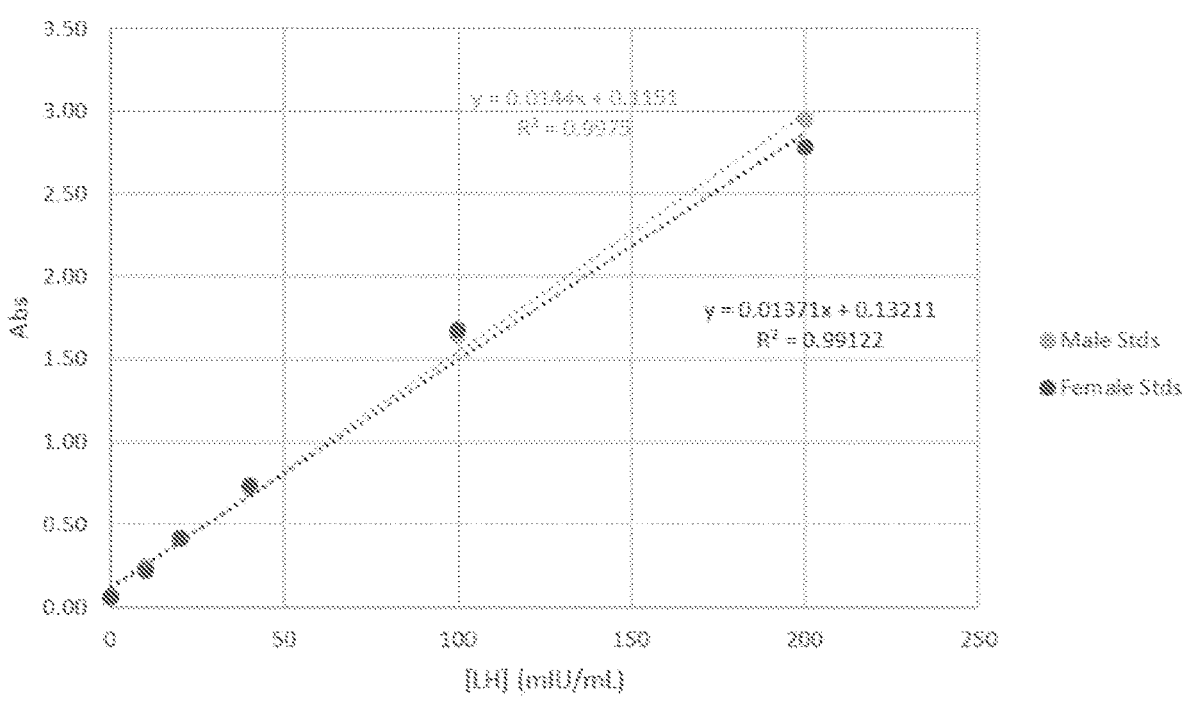
FIG. 64 shows values obtained for ELISA standards and generated standard curves.

The absorbance values obtained for the ELISA standards on the male plate and the female plate, as well as the generated standard curves, are shown in FIG. 64. Moreover, the average absorbance values for unspiked samples are shown below in TABLE 24. Female samples have an "F" in front of the sample number; male urine samples have a "U" in front of the number. It is important to note that U4 and U5 (which have previously shown discrepancies with the PdG assay), register as relatively high compared to the other male samples. The female samples range from 0.05 (essentially a true blank) to 0.16 (still below the 10 mIU/mL standard's absorbance).

TABLE 24

| Sample | Abs |
| --- | --- |
| F1 | 0.05 |
| F2 | 0.06 |
| F3 | 0.07 |
| F4 | 0.16 |
| F5 | 0.13 |
| F6 | 0.07 |
| F7 | 0.05 |

TABLE 24-continued

| Sample | Abs |
|---|---|
| F8 | 0.05 |
| F9 | 0.05 |
| F10 | 0.07 |
| F11 | 0.05 |
| F12 | 0.05 |
| F13 | 0.05 |
| F14 | 0.05 |
| F15 | 0.12 |
| F16 | 0.07 |
| F17 | 0.05 |
| F18 | 0.05 |
| F19 | 0.06 |
| F20 | 0.06 |
| U1 | 0.05 |
| U2 | 0.05 |
| U3 | 0.05 |
| U4 | 0.09 |
| U5 | 0.10 |
| U6 | 0.06 |
| U7 | 0.05 |

Although the standards included in the ELISA kit used did cover the desired dynamic range of absorbance values, there were no samples—spiked or natural—that produced absorbance values within the expected range.

All samples showed absorbance values less than the lowest positive standard (10 mIU/mL). This is explainable for the female samples by the idea that the LH surge window was missed for all twenty females on the day of collection. However, given the fact that the PdG ELISA results for these samples shows a large variety of concentrations, suggesting different times within the ovulation windows, this explanation is somewhat lacking.

As for the male samples, all were tested at 100 mIU/mL LH, and Urine 7 was spiked with up to 200 mIU/mL LH. The data from the previously run experiment showed that, while the male urine samples were reduced in signals relative to the standard curves, the high concentration samples showed much higher absolute absorbance values.

f. Preview of Duplex Strips with Twenty Female Samples

Purpose: The twenty female urine samples of part e of this Example will be tested at n=1 to quickly compare the duplex strip's LH test line values with the ELISA absorbance measured above in part e of this example.

The materials and equipment used in this study are shown below in TABLE 25

TABLE 25

| Assay components |
|---|
| LH/PdG duplex cassettes: |
| CN140 with 1 mg/mL PdG-BSA test line and |
| 2 mg/mL mAb 5301 anti-LH test line |
| 8980 conjugate pads sprayed with OD3 anti- |
| LH gold and OD2.5 anti-PdG gold |
| 8 μL of 0.5M Tris + 0.5% Tween-20 + |
| 0.5% casein spotted then dried in sample |
| Reagents |

| |
|---|
| Male urine samples from Lee Biosolutions (labeled U1-U3) |
| Male urine samples donated from DCN (labeled U4-U7) |
| ELISA standards from DRG LH ELISA |
| Female urine samples from Lee Biosolutions (labeled F1- |
| LH at 33 IU/mL in water, stored at −20° C. |
| DI Water (>18.0 MΩ) |

TABLE 25-continued

| Equipment |
|---|
| 96-well plates (flat bottom, cloudy polypropylene) |
| Kinematic cutter |
| Pipettes |

Experimental details are given below:

1. Bring samples to room temperature

2. Duplex cassette testing procedure a. Add 80 μL of urine sample to sample well b. Read on the Axxin Reader at 15 min 3. Samples (n=1)

a. Female samples run unspiked b. Male samples will be run unspiked and spiked with (25 and 100) mIU/mL LH Results are shown in FIG. 65. From the right three columns of FIG. 65, the current duplex strip's PdG test line is still correctly measuring PdG content in the twenty female urine samples. The PdG test line values are significantly lower due to 1) lower test line PdG-BSA concentration, 2) lower PdG gold, and 3) increased concentration of running buffer per strip compared to the original set.

As for the LH series, the following should be noted:

1. The ELISA standard for 10 mIU/mL (S1) is higher than nearly all LH test lines observed in any strip-based LH assay prepared thus far 2. The test line peak values generally match the ELISA absorbance values.

3. The maximum test line signal for LH is actually fairly high, suggesting that the LH being measured is not low in urine.

Figure 66:
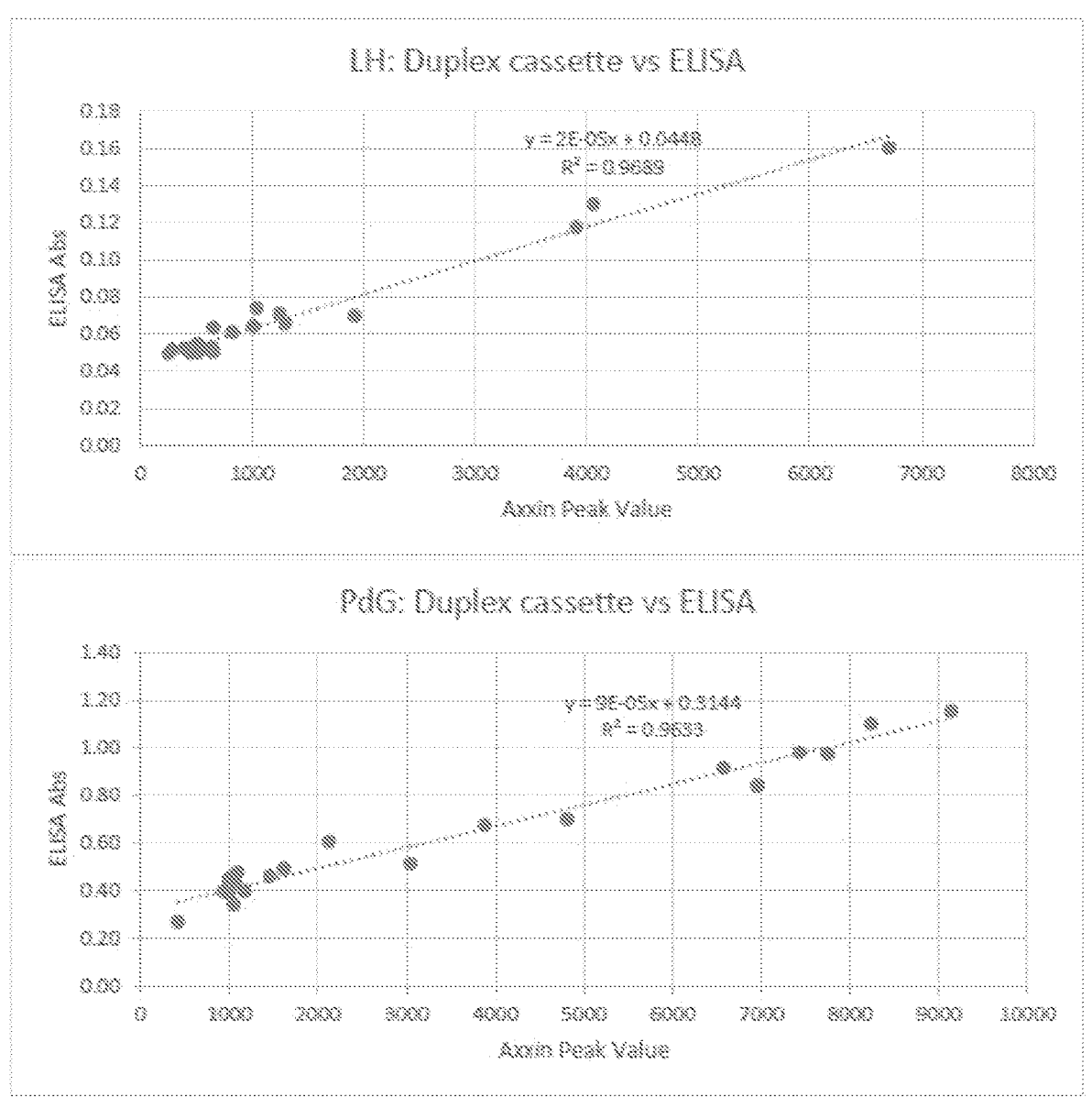
FIG. 66 shows LH and PdG Axxin peak value correlations with their respective ELISA measurements.

LH and PdG correlations with their respective ELISA's are shown in FIG. 66. Both LH and PdG ELISA absorbance values show a high degree of correlation with duplex test line peak values.

g. Full LH/PdG Duplex Cassette Testing with Twenty Female Samples

Purpose: The LH/PdG duplex cassettes were tested with higher replicate numbers using a series of spiked samples as well as twenty unspiked femlate urine samples.

The materials and equipment used in this study are shown below in TABLE 26.

TABLE 26

| Assay components |
|---|
| LH/PdG duplex cassettes: |
| CN140 with 1 mg/mL PdG-BSA test line and |
| 2 mg/mL mAb 5301 anti-LH test line |
| 8980 conjugate pads sprayed with OD3 anti- |
| LH gold and OD2.5 anti-PdG gold |
| 8 μL of 0.5M Tris + 0.5% Tween-20 + |
| 0.5% casein spotted then dried in sample |
| Reagents |

| |
|---|
| Male urine samples from Lee Biosolutions (labeled U1-U3) |
| Male urine samples donated from DCN (labeled U4-U7) |
| ELISA standards from DRG LH ELISA |
| Female urine samples from Lee Biosoluions (labeled F1- |
| LH at 33 IU/mL in water, stored at −20° C. |
| DI Water (>18.0 MΩ) |

TABLE 26-continued

| Equipment |
| --- |
| 96-well plates (flat bottom, cloudy polypropylene) |
| Kinematic cutter |
| Pipettes |

The experimental methods used in this study are described below:

1. Bring samples to room temperature
2. Duplex cassette testing procedure
   a. Add 80 μL of urine sample to sample well
   b. 30 sec between cassettes
   c. Read on the Axxin Reader at 15 min
3. Sample sets a. Female samples (n=4)
   b. Male samples U1-U6 will be run unspiked and spiked with 100 mIU/mL LH (n=2)
   c. Male sample U6 will be run spiked at 200 mIU/mL (n=3)
   d. Male sample U7 will be run with the following concentrations (n=3)
      i. +(0, 10, 20, 50, 75, 100) mIU/mL
   e. Four new samples will be run with n=3 (named U8-U11, though whether they are male or female is unknown)
4. Sample preparation Results of the twenty female samples run are shown in FIG. 67. Four cassettes were not quantified due to human error in the measurement process. Results of the spiked and unspiked male urine samples are shown in FIG. 68 All seven male urine samples were run unspiked as well as spiked with 100 mIU/mL LH. Since the PdG amount is not changing within a urine sample, the PdG values of the four cassettes in each group are averaged together. In the first two male urine samples (U1 and U2), no significant change occurred in the LH peak value from the addition of LH. The remainder of samples showed significant increases in test line signal at the +100 mIU/mL level. The results obtained for spiked male samples are summarized in FIG. 69. U1 and U2 showed no increased signals when spiked with 100 mIU/mL LH. This may be a sampling error because U1 and U2 have shown responses to spiked LH in multiple experiments. U3 through U7 all show increased test line signal when run with spiked LH, although the initial test line signal values vary by a factor of up to 3. The four new samples showed different levels of LH test line intensity.

Figure 71:
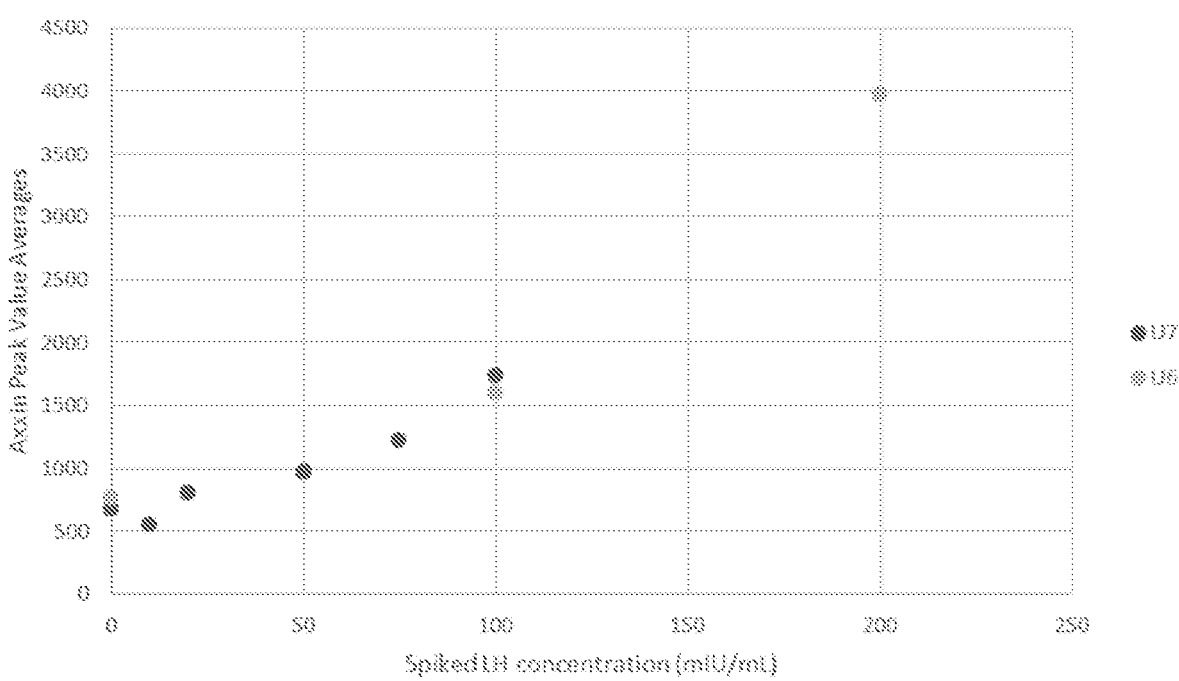
FIG. 71 shows a graph of Axxin peak value vs. LH concentration for two samples of male urine.

In addition to the (0, 100) mIU/mL samples shown in FIG. 69, U6 and U7 were run with larger ranges of spiked LH. The results of experiments with larger ranges of spiked LH are shown in FIG. 70. As can be seen in FIG. 71, the (0 and 100) mIU/mL samples align well for U6 and U7, with the additional U7 samples filling in the dynamic range appropriately. The 10 mIU/mL sample was not discernible from the unspiked condition.

Figure 73:
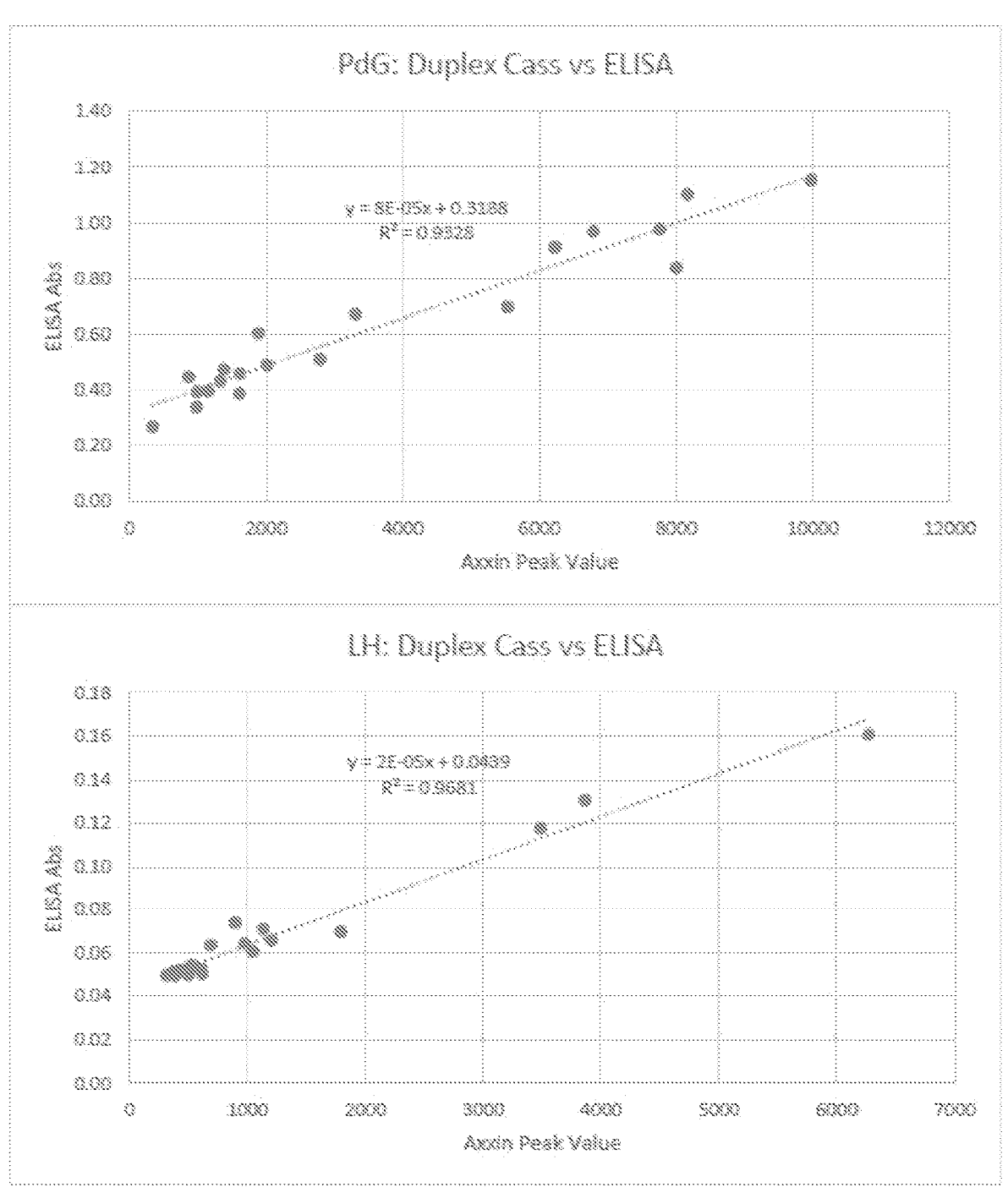
FIG. 73 shows an analysis of the correlation between Axxin peak values determined with duplex PdG/LH cassettes and measured ELISA absorbance values when each method is used to measure PdG or LH concentration.

FIG. 72 and FIG. 73 shows the correlations of PdG and LH test lines with their respective ELISA absorbance values. % CVs are added for the Axxin test line peak values. Graphs of the above data will be shown in the next two figures. Correlations seen in this study were very similar seen in the previous single strip experiment. Test line peaks for both assays are highly correlated with the ELISA absorbance values.

A summary of experiments comparing PdG and LH concentrations as measured with both the developed duplex strips and commercial ELISA kits is shown below in TABLE 27.

TABLE 27

| Assay | ELISA | Duplex Cassette | $R^2$ | Sample notes |
| --- | --- | --- | --- | --- |
| PdG | Sample absorbances within acceptable distance from standards | In line with ELISA Abs. | 0.93 | Good coverage across the dynamic range |
| LH | Sample absorbances greatly below expected, below lowest positive standard | In line with ELISA Abs. | 0.97 | Samples heavily skewed towards low concentrations |

Example 8: Custom Reader Development

Figure 74:
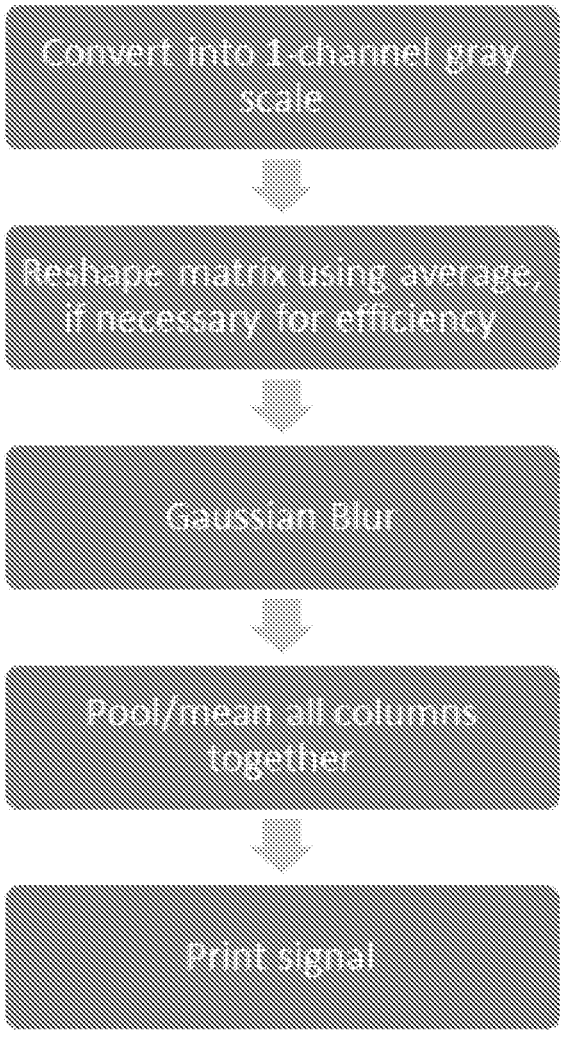
FIG. 74 shows the algorithm used by a developed custom lateral flow immunoassay strip reader.
Figure 75:
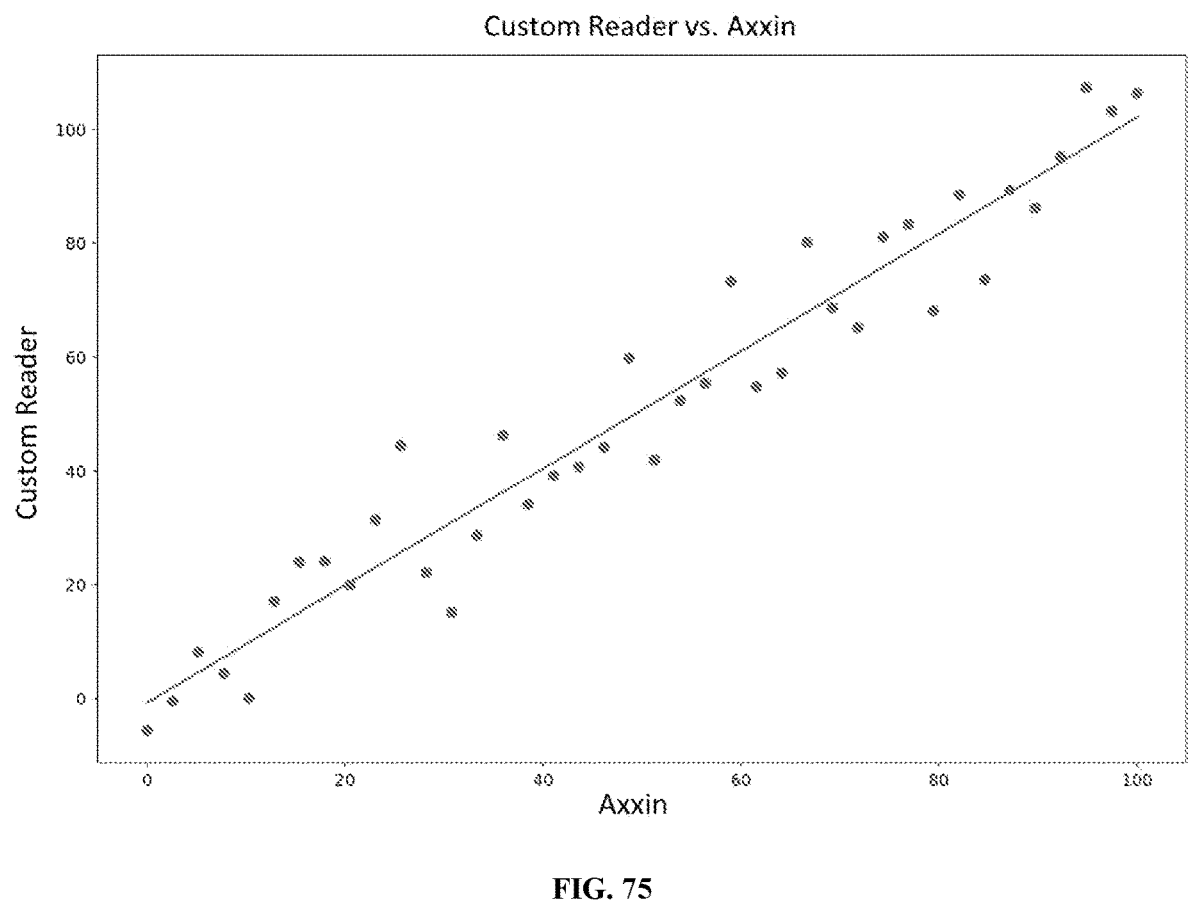

Though LFIA strips described in previous experiments were read with an Axxin reader, a custom reader has also been developed to measure test and control line signal. To measure signal the custom reader converts cropped regions of test strips into 3-channel RBG matrices. The algorithm shown in FIG. 74 is used to convert the 3-channel matrices into basic signal. When compared to readings obtained with the Axxin reader, readings obtained with the custom reader correlated strongly, as shown in FIG. 75

Example 9: Analysis and Performance

A person's health status can be classified using many objective and subjective features. Pain is quantified by scales of subjective measure where biomarkers in blood analysis are more objective, representing specific values as analyzed by commercial machinery. Modern statistical modeling and machine learning methods provide the tools necessary to utilize multiple feature types into a single analysis. In theory, if a dataset existed that represented the longitudinal detection of both subjective and objective features; we could leverage these types of analysis to classify individuals into categories of health status.

An example of this data set would be of only women and include: height, weight, age, gender, pregnancy status, length of current menstrual cycle, average length of menstrual cycle, estimated day of ovulation as a function of; day of last period and length of cycle, length of current period, length of average period, number of peak hormone level days, average number of peak hormone days, number of cycles collected, number of days of intercourse, period intensity, cervical fluid description, pain, cravings, digestion, hair, skin, stool, body temperature, exercise, sleep, sex drive, mental state, mood, motivation, productivity, social behavior, partying, energy, birth control use, medication use, hormone therapy use, ailments. These data include thousands of samples.

To clean and parse this information prior to analysis you must first eliminate samples in the data that have missing values for some of the features. Further, you would need to eliminate superfluous data that is not important to the hypothesis of being able to categorize objects by health status. This would mean eliminating identifying and demographic data. Finally, non-numerical data will be mapped to a numerical representation.

Once the dataset is reduced to a concise set of useful information it will need to be pre-processed to normalize all features onto a unified scale. A minimum to maximum normalization algorithm is used, where; the values of a numeric range of a feature of data, i.e. a property, are reduced to a scale between zero and one.

To categorize the data into individual health status', based on individual features, the data was loaded into a k-means machine learning algorithm. During unsupervised clustering the model clustered data that had not been previously labelled into clusters based on inherent commonalities in the input features. The result was clusters of objects based on similarities in their health status. The number of clusters was predetermined by visualizing the innate separation of the data and in this case was six.

Once the health status of the existing women is determined, it would be useful to be able to classify an unforeseen, new, woman. In order to do this, we leveraged another type of machine learning algorithm called a naïve Bayes multi-class classifier. The model was trained on the original, cleaned, dataset and also the health status categories as labelled by the k-means algorithm. The model was trained and tested by training on a randomly selected set of the data and then tested with the remainder. This technique was used in ten split combinations and repeated ten times, in a method known as k-fold cross validation.

Figure 76:
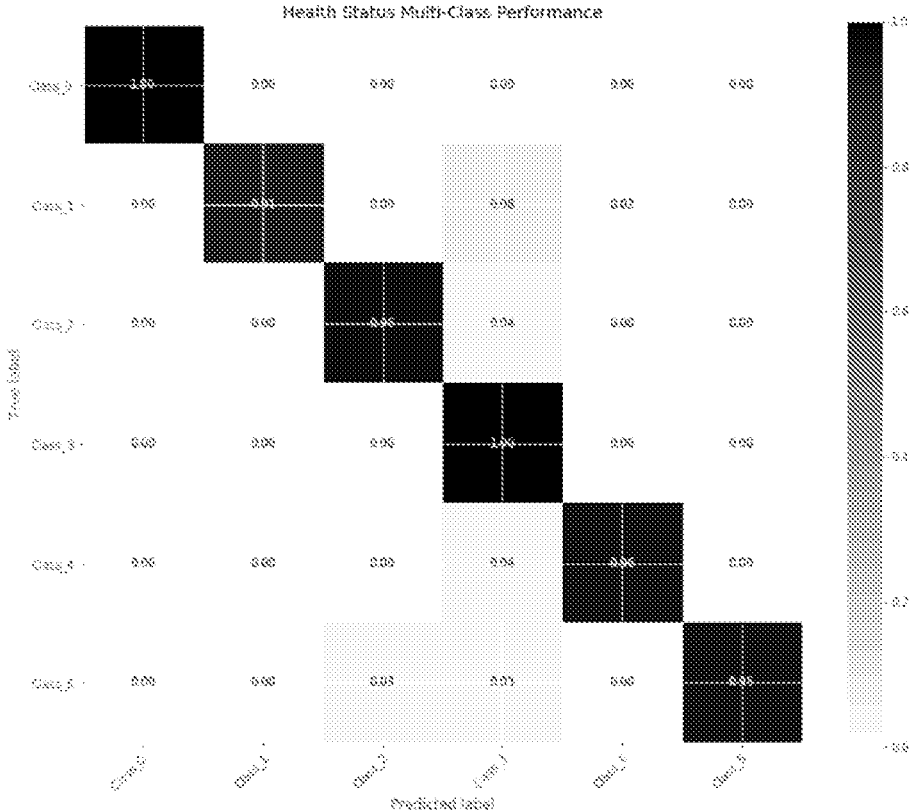
FIG. 76 shows a confusion matrix demonstrating the performance of a classification model.
Figure 77:
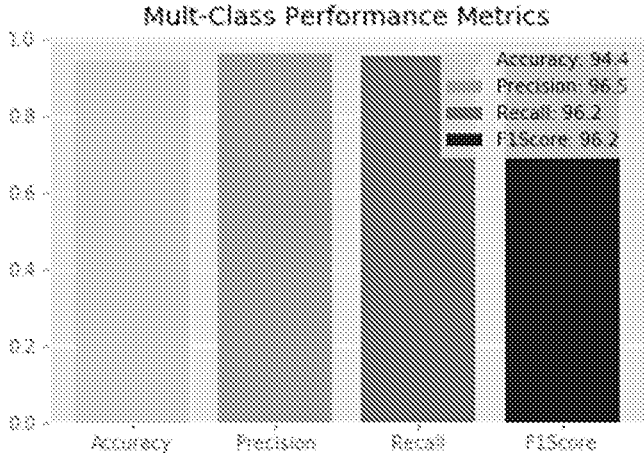
FIG. 77 shows the multi-class performance metrics of a classification model.

The performance of this model's ability to classify a woman into a specific health status was quantified by common performance metrics. The results can be observed in FIG. 76 and FIG. 77. The dataset can be publically available and can be downloaded at https://epublications-.marquette.edu/data_nfp/7/.

Example 10: Database and AI

Figure 78:
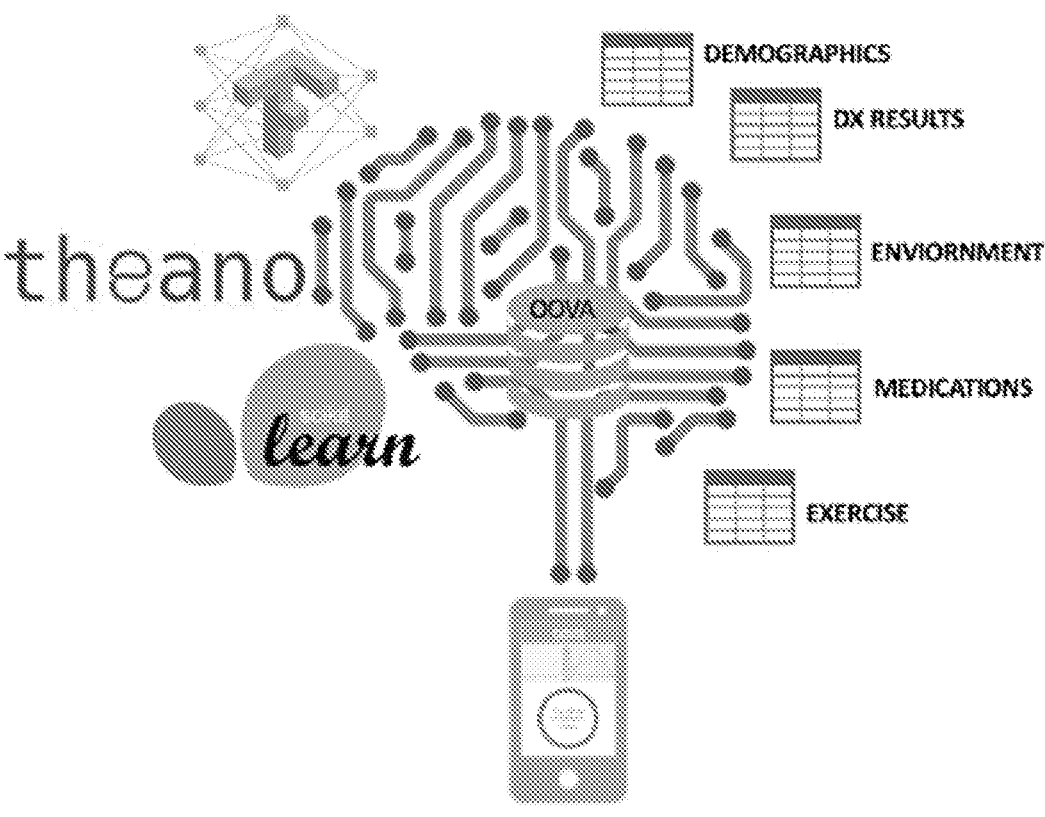
FIG. 78 shows a schematic of an exemplary back-end system for developing the fertility algorithm.

The data collected from users is stored in an extensive database. Information, such as patient demographics, image capture results, environment, medications, and exercise, are used to forecast the ovulatory window of a subject, and to provide the user with a full scope of the subject's fertility profile. FIG. 78 shows a schematic of an example back-end system for developing the fertility algorithm.

Example 11: Sample Tests Using External Optical Sensor or Smart Phone Camera

Figure 79:
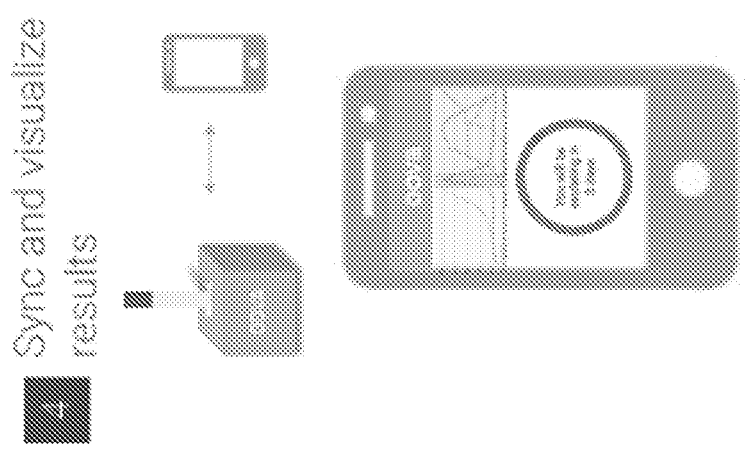
FIG. 79 shows the steps of quantifying an analyte using an optical sensor device.
Figure 79:
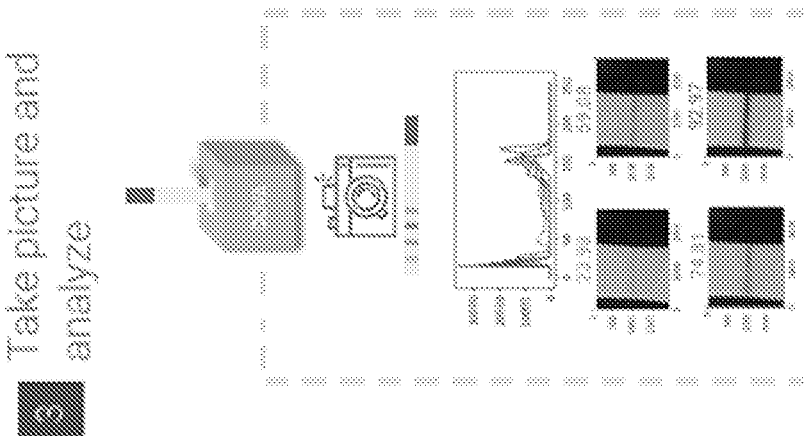
Figure 79:
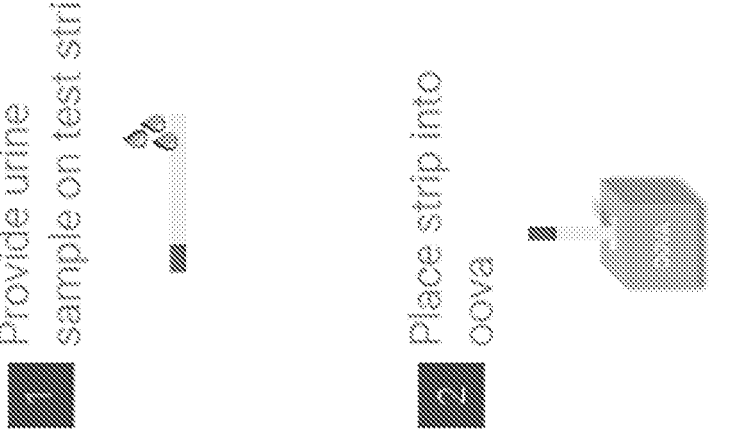

Sample analysis using optical sensor device: A urine sample is provided onto a test strip, and the strip is placed into an analytical device. After a specified amount of time, an optical sensor in the analytical device takes a picture of the test strip and analyzes the results. The results are automatically synced to a cloud-based data storage system, and visualized to the user on through a smartphone app. FIG. 79 shows the steps of quantifying an analyte using an optical sensor device.

Figure 80:
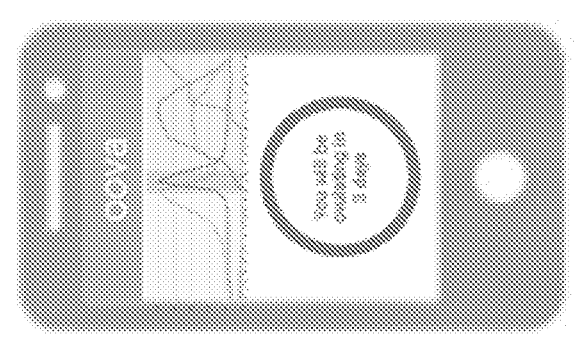
FIG. 80 shows the steps of quantifying an analyte using a smartphone camera.
Figure 80:
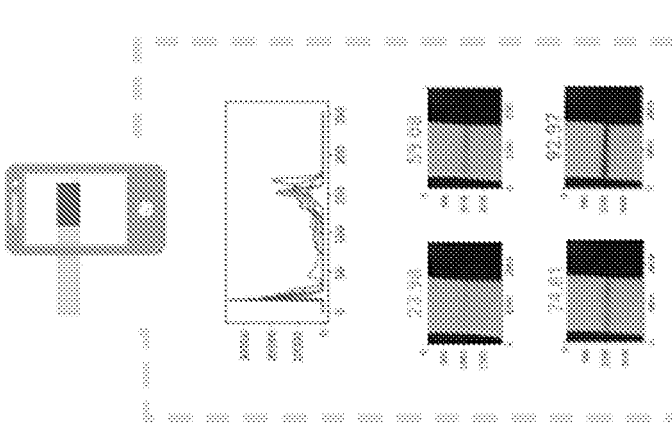
Figure 80:
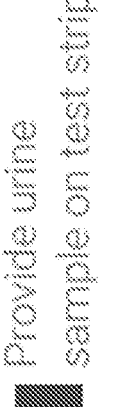
Figure 80:
Figure 80:

Sample analysis using a smartphone camera: A urine sample is provided onto a test strip. After a specified amount of time, an image of the strip is obtained using a smartphone camera. The results are analyzed. The results are automatically synced to a cloud-based data storage system, and visualized to the user through a smartphone app. FIG. 80 shows the steps of quantifying an analyte using a smartphone camera.

Example 12: Therapeutic Intervention Using Quantitative Hormone Measurements

Figure 81:
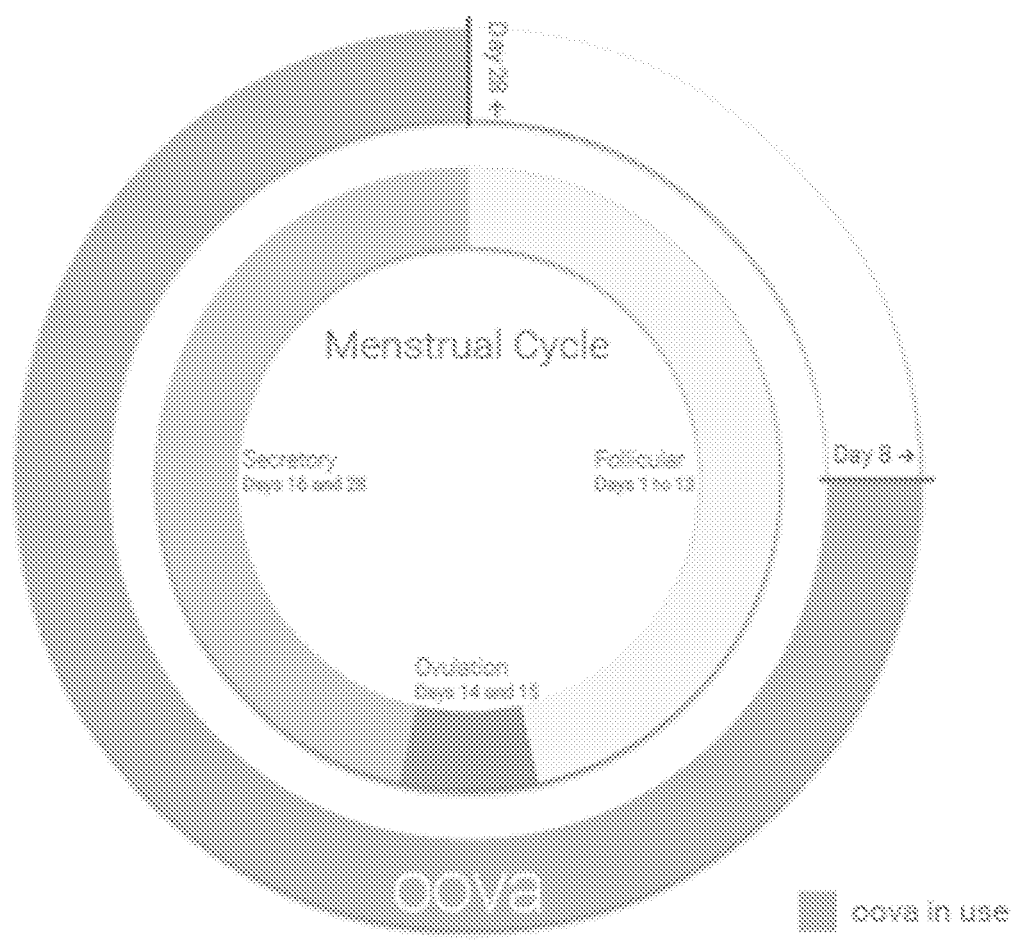
FIG. 81 illustrates an exemplary schedule depicting how a method or device described herein can be used to track a woman's menstrual cycle.

FIG. 81 illustrates the use of a method or device of the disclosure throughout a woman's menstrual cycle.

Conventional therapeutic intervention: Unable to conceive naturally for over 1 year, a woman is prescribed clomiphene citrate (Clomid®). The woman visits the clinic on day 3 of her menstrual cycle to get baseline hormone levels from a blood sample. On day 5 of her menstrual cycle, she visits the clinic to get a pelvic exam via ultrasound. On days 7, 8, 9, 10, and 11 of her menstrual cycle, she takes Clomid®. On day 12 of her menstrual cycle, the woman self-administers an hCG shot ("trigger shot") to induce ovulation. On days 13, 14, 15, 16, and 17, the woman visits the clinic for daily blood tests and/or ultrasound scans. On day 22 of her menstrual cycle, the woman visits the clinic to test her progesterone levels through a blood test to confirm ovulation. On day 27 of her menstrual cycle, the woman visits the clinic to confirm pregnancy through an hCG blood test.

Therapeutic intervention using methods of the disclosure: Unable to conceive naturally for over 1 year, a woman is prescribed clomiphene citrate (Clomid®). The woman visits the clinic on day 3 of her menstrual cycle to get baseline hormone levels from a blood sample. On day 5 of her menstrual cycle, she visits the clinic to get a pelvic exam via ultrasound. On day 1 of her menstrual cycle, the woman starts taking daily urine tests to monitor her hormone levels using a device and methods of the disclosure. On days 7, 8, 9, 10, and 11 of her menstrual cycle, she takes Clomid®. On day 12 of her menstrual cycle, the woman self-administers an hCG shot ("trigger shot") to induce ovulation. The woman continues to take daily urine tests to monitor her hormone levels, including her progesterone and hCG levels. The woman is able to monitor her LH, progesterone, estradiol, and hCG levels without visiting the clinic, resulting in real time monitoring and reduced monitoring costs.

Figure 82:
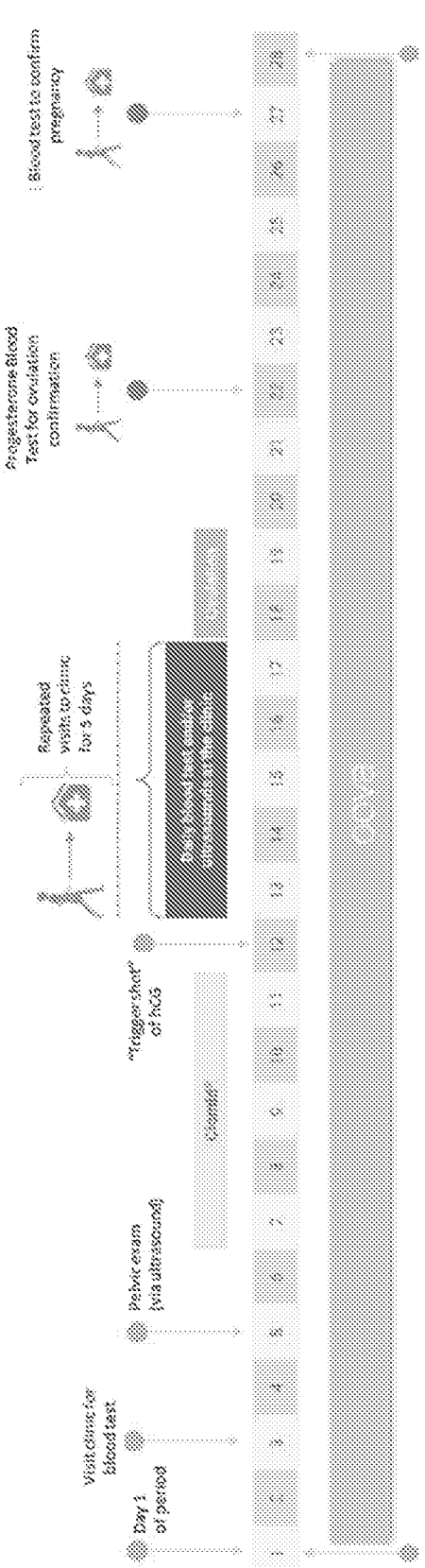
FIG. 82 illustrates a comparison of a conventional therapeutic intervention and a therapeutic intervention using methods of the disclosure.

FIG. 82 illustrates a comparison of a conventional therapeutic intervention and a therapeutic intervention using methods of the disclosure.

Example 13: In Vitro Fertilization Treatment Using Quantitative Hormone Measurements Conventional therapeutic intervention: A woman is undergoing in vitro fertilization (IVF) treatment and must obtain frequent measurements of her fertility hormones and metabolites to ensure a successful procedure. On days 5, 6, 7, 8, 9, 10, 11, 12, and 13 of her menstrual cycle, the woman self-injects fertility medications to stimulate her ovaries to release eggs, and also visits the clinic for daily blood tests to measure estrogen levels and ultrasounds. On day 14 of her menstrual cycle, the woman visits the clinic for egg retrieval. The retrieved eggs are fertilized in vitro. On day 17 of her menstrual cycle, the woman visits the clinic for a viable embryo to be transferred to her uterus. On days 17-27 of her menstrual cycle, the woman takes progesterone supplements to support her uterine lining and implantation. On day 28 of her cycle, the woman visits the clinic for an hCG blood test to confirm pregnancy. There is a delay from when the physician receives blood work and the woman receives her test results.

Therapeutic intervention using methods of the disclosure: A woman is undergoing in vitro fertilization (IVF) treatment and must obtain frequent measurements of her fertility hormones and metabolites to ensure a successful procedure. On days 5, 6, 7, 8, 9, 10, 11, 12, and 13 of her menstrual cycle, the woman self-injects fertility medications to stimulate her ovaries to release eggs, takes daily uterine tests using methods of the disclosure to measure estrogen levels, and visits the clinic for ultrasound scans of her ovaries. On day 14 of her menstrual cycle, the woman visits the clinic for egg retrieval. The retrieved eggs are fertilized in vitro. On day 17 of her menstrual cycle, the woman visits the clinic for a viable embryo to be transferred to her uterus. On days 17-27 of her menstrual cycle, the woman takes progesterone supplements to support her uterine lining and implantation. The woman continues to take daily urine tests using methods of the disclosure to monitor her hormone levels until she confirms pregnancy on day 28 of her menstrual cycle. There is no delay from when the physician receives blood work and the woman receives her test results.

Figure 83:
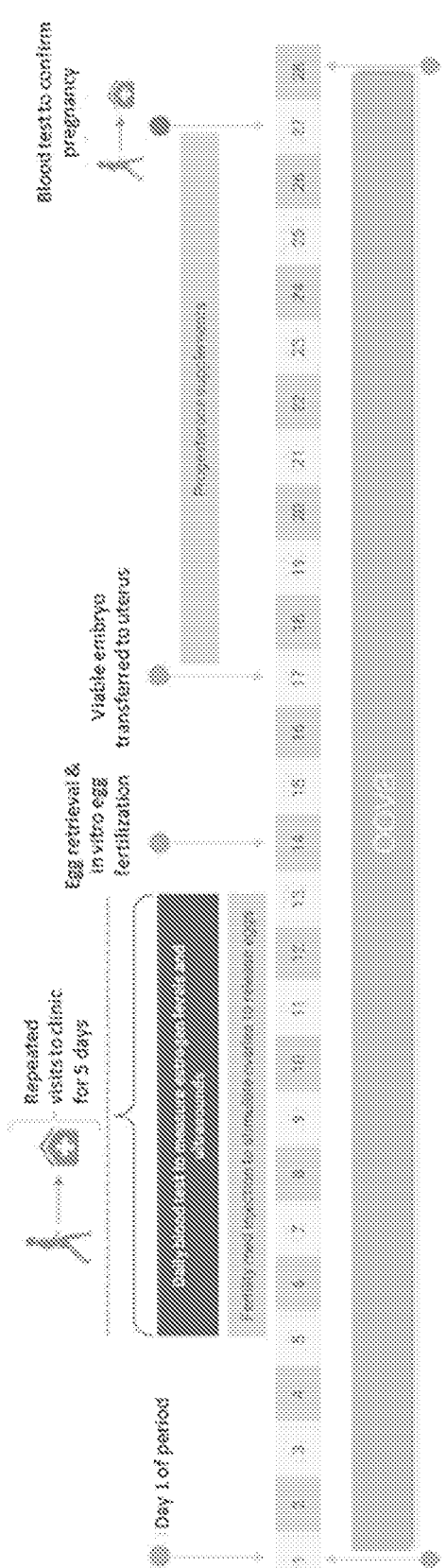
FIG. 83 illustrates a comparison of a conventional IVF process to an IVF process using methods of the disclosure.

FIG. 83 illustrates a comparison of the conventional IVF process to an IVF process that uses daily urine tests to quantify hormone levels.

Example 14: Alerting/Reporting System

During registration a mobile application captures critical information (including but not limited to): height, weight, age, and date of last menstrual cycle. This information is input into the machine learning pipeline and a woman is classified into one of six clusters.

Cluster 1 are women in their mid-20s, high BMI, experience a long cycle, have periods longer than 5 days, generally experience late ovulation, and have extended number of peak ovulatory days.

Cluster 2 are women in their mid to late 30s, have mid to high BMI, experience short or average cycle lengths, their period lasts around 5 days, have normal ovulation, and a normal number of peak ovulatory days.

Cluster 3 are women in their late 20s to early 30s, high BMI, experience short cycles, have a period that lasts around 5 days, experience early ovulation, and have a normal number of peak ovulatory days.

Cluster 4 are women in their mid-30s, have low to mid BMI, experience short cycles, have periods less than 5 days, have normal ovulation, and have a normal number of peak ovulatory days.

Cluster 5 are women in their mid 20s to mid 30s, low to mid BMI, experience long cycles, their period that lasts around 5 days, experience late ovulation, and a normal number of peak ovulatory days.

Cluster 6 are women in their early to mid 20s, low to average BMI, have an average cycle, normal period length, typical ovulation, and a normal number of peak ovulatory days.

The cluster a woman is classified into drives the type of information she will receive her reports.

Within the mobile application, a woman receives two levels of reporting. The first level is daily. Every day, after a woman scans her test strip, she is provided with a daily action plan. The daily action plan has a single action item in three unique categories: 1) Physical Health, 2) Nutritional Health, and 3) Mental Health. As a woman uses the test strips and mobile application, an artificial intelligence algorithm begins to learn her hormone profile more and more. Using all of the inputs, the algorithm is able to make the suggestions needed to help regulate her hormone levels.

The second level of reporting is a monthly report. The first piece of the monthly report includes recommendations. Based off of the data collected through the mobile application, the algorithm will make two recommendations: 1) Dietary supplements and 2) Diagnostic testing. Both of these recommendations are driven by the combination of the user's daily hormone levels and subjective tracking information captured in the mobile application.

The second piece of the monthly report dives deeper into a user's hormone profile and her results over the course of the month. The report shows how a user's hormone levels differ from the average woman and explain meaningful differences. The report also goes into more detail about why the report suggested certain things in her daily action plans that month. Finally, the explains trends observed in various input variables including but not limited to sleep, mood, and energy.

The hormone profile referred to above can play a role in inferring prenatal disease, newborn health status, medical adherence status, cancer, immune inflammatory disorder, neurological conditions, infectious diseases, and other analytes.

EMBODIMENTS

The following non-limiting embodiments provide illustrative examples of the disclosure, but do not limit the scope of the disclosure.

Embodiment 1. A computer implemented method comprising: (a) capturing, by a camera of a mobile telecommunications device, an image of a detection region on a substrate in contact with a biological sample from a subject, wherein the detection region comprises a detector that undergoes a change in a visible property of the detection region in response to contact with an analyte in the biological sample, wherein the analyte is associated with a health profile of the subject; (b) processing, by a processor of the mobile telecommunications device, pixel intensities of the image of the detection region on the substrate in contact with the biological sample, thereby quantifying an amount of the analyte in the detection region on the substrate to determine a concentration of the analyte in the biological sample, wherein the pixel intensities correspond to the visible property of the detector; and (c) providing, by the processor of the mobile telecommunications device, a report on the health profile of the subject based on the concentration of the analyte.

Embodiment 2. The computer-implemented method of embodiment 1, further comprising providing a recommendation corresponding to a therapy based on the report of the health profile of the subject.

Embodiment 3. The computer-implemented method of embodiment 1 or 2, further comprising providing an alert corresponding to the health profile of the subject.

Embodiment 4. The computer-implemented method any one of embodiments 1-3, wherein the detection region comprises a test area and a control area of the substrate.

Embodiment 5. The computer-implemented method of embodiment 4, wherein the test area comprises analyte-bound particles, and the control area comprises analyte-unbound particles.

Embodiment 6. The computer-implemented method of embodiment 4 or 5, wherein the test area comprises an analyte capture agent.

Embodiment 7. The computer-implemented method of embodiment 6, wherein the analyte capture agent is an antibody.

Embodiment 8. The computer-implemented method of embodiment 6 or 7, wherein the detector is a colloidal gold particle that is bound to the analyte capture agent.

Embodiment 9. The computer-implemented method of any one of embodiments 1-8, further comprising quantifying the amount of the analyte at a first time point and at a second time point.

Embodiment 10. The computer-implemented method of embodiment 9, further comprising comparing the amount of the analyte at the first time point and at the second time point, wherein the comparing provides an indication of a change in the concentration of the analyte.

Embodiment 11. The computer-implemented method of any one of embodiments 1-10, wherein the substrate is a lateral flow device.

Embodiment 12. The computer-implemented method of any one of embodiments 1-11, wherein the analyte is luteinizing hormone.

Embodiment 13. The computer-implemented method of any one of embodiments 1-11, wherein the analyte is pregnanediol glucuronide.

Embodiment 14. The computer-implemented method of any one of embodiments 1-13, wherein the health profile comprises an ovulation status.

Embodiment 15. The computer-implemented method of any one of embodiments 1-14, wherein the health profile comprises a newborn health status.

Embodiment 16. The computer-implemented method of any one of embodiments 1-15, wherein the health profile comprises a disease status.

Embodiment 17. The computer-implemented method of any one of embodiments 1-16, wherein the health profile comprises a medication adherence status.

Embodiment 18. The computer-implemented method of any one of embodiments 1-17, wherein the processing is in real-time.

Embodiment 19. The computer-implemented method of any one of embodiments 1-18, wherein the biological sample is urine.

Embodiment 20. The computer-implemented method of any one of embodiments 1-19, wherein the visible property is hue.

Embodiment 21. The computer-implemented method of any one of embodiments 1-19, wherein the visible property is saturation.

Embodiment 22. The computer-implemented method of any one of embodiments 1-19, wherein the visible property is value.

Embodiment 23. The computer-implemented method of any one of embodiments 1-19, wherein the visible property is lightness color space.

Embodiment 24. The computer-implemented method of any one of embodiments 1-23, wherein determining the concentration of the analyte in the biological sample is based on a training set of quantified concentrations of a plurality of analytes.

Embodiment 25. A computer program product comprising a non-transitory computer-readable medium having computer-executable code encoded therein, the computer-executable code adapted to be executed to implement a method comprising: (a) (a) providing an analyte processing and reporting system of a mobile telecommunications device, wherein the analyte processing and reporting system comprises: (i) an optical sensor module; (ii) a quantification module; and (iii) a visualization module; (b) capturing, by the optical sensor module, an image of a detection region on a substrate in contact with a biological sample from a subject, wherein the detection region comprises a detector that undergoes a change in a visible property of the detection region in response to contact with an analyte in the biological sample, wherein the analyte is associated with a health profile of the subject; (c) processing, by the quantification module, pixel intensities of the image of the detection region on the substrate in contact with the biological sample, thereby quantifying an amount of the analyte in the detection region on the substrate to determine a concentration of the analyte in the biological sample, wherein the pixel intensities correspond to the visible property of the detector; and (d) providing, by the visualization module, a report on the health profile of the subject based on the concentration of the analyte in the biological sample.

Embodiment 26. The computer program product of embodiment 25, wherein the processing is in real-time.

Embodiment 27. The computer program product of embodiment 25 or 26, further comprising providing, by the visualization module, a recommendation corresponding to a therapy based on the report of the health profile of the subject.

Embodiment 28. The computer program product of any one of embodiments 25-27, further comprising providing, by the visualization module, an alert corresponding to the health profile of the subject.

Embodiment 29. The computer program product of any one of embodiments 25-28, wherein the processing comprises processing pixel intensities over a first vector spanning a test area of the detection region and processing pixel intensities over a second vector spanning a control area of the detection region.

Embodiment 30. The computer program product of embodiment 29, wherein the processing comprises comparing pixel intensities of the test area and the control area.

Embodiment 31. The computer program product of embodiment 30, wherein the comparing comprises normalizing pixel intensities between the test area and the control area, thereby generating the concentration of the analyte in the biological sample.

Embodiment 32. The computer program product of any one of embodiments 25-31, further comprising quantifying, by the quantification module, the amount of the analyte at a first time point and at a second time point.

Embodiment 33. The computer program product of embodiment 32, wherein the first time point and the second time point are about 24 or fewer hours apart.

Embodiment 34. The computer program product of embodiment 32 or 33, further comprising comparing the amount of the analyte at the first time point and at the second time point, wherein the comparing provides an indication of a change in the concentration of the analyte.

Embodiment 35. The computer program product of any one of embodiments 25-34, wherein the health profile comprises an ovulation status.

Embodiment 36. The computer program product of any one of embodiments 25-35, wherein the health profile comprises a newborn health status.

Embodiment 37. The computer program product of any one of embodiments 25-36, wherein the health profile comprises a disease status.

Embodiment 38. The computer program product of any one of embodiments 25-37, wherein the health profile comprises a medication adherence status.

Embodiment 39. The computer program product of any one of embodiments 25-38, wherein the visible property is hue.

Embodiment 40. The computer program product of any one of embodiments 25-38, wherein the visible property is saturation.

Embodiment 41. The computer program product of any one of embodiments 25-38, wherein the visible property is value.

Embodiment 42. The computer program product of any one of embodiments 25-38, wherein the visible property is lightness color space.

Embodiment 43. The computer program product of any one of embodiments 25-42, wherein determining the concentration of the analyte in the biological sample is based on a training set of quantified concentrations of a plurality of analytes.

Embodiment 44. The computer-implemented method of any one of embodiments 1-11 or 14-24, wherein the analyte is progesterone.

What is claimed is:

1. A computer-implemented method, comprising:
(a) capturing, by a camera of a mobile telecommunications device, an image of a detection region on a substrate in contact with a biological sample from a subject, wherein the biological sample is urine, wherein the detection region comprises a detector that undergoes a change in a plurality of visible properties of the detection region in response to contact with an analyte in the biological sample, wherein the analyte is associated with a hormone profile of the subject, wherein the analyte is selected from the group consisting of: luteinizing hormone, progesterone or a metabolite thereof, estrogen or a metabolite thereof, and human chorionic gonadotropin;
(b) processing, by a processor of the mobile telecommunications device, pixel intensities of an RGB image of the detection region on the substrate in contact with the biological sample, wherein the processing is in real-time, wherein the processing comprises: processing the RGB image by a rule-based image processing algorithm, wherein the rule-based image processing algorithm processes the RGB image by:
1) colorspace conversion;
2) topological/morphological transformation;
3) declivity-based edge detection;
4) clustering using a Gaussian mixture models
5) normalization using adaptive histogram equalization; and
6) calibration using an information storage code,
thereby quantifying an amount of the analyte in the detection region on the substrate to determine a concentration of the analyte in the biological sample based on a training set of quantified concentrations of a plurality of analytes, wherein the pixel intensities correspond to the plurality of visible properties of the detector, wherein the visible properties are hue, saturation, value, and lightness color space;
c collecting, by a computing network connected to the mobile telecommunications device, the amount of the analyte;
d analyzing, by the computing network, the amount of the analyte, thereby generating analyzed data specific to the subject;
e generating, by the computing network, a report on the hormone profile specific to the subject based on the analyzing;
f providing, by the processor of the mobile telecommunications device, the report on the hormone profile of the subject.

2. The computer-implemented method of claim 1, further comprising providing a recommendation corresponding to a therapy based on the report of the hormone profile of the subject.

3. The computer-implemented method of claim 1, further comprising providing an alert corresponding to the hormone profile of the subject.

4. The computer-implemented method of claim 1, wherein the detection region comprises a test area and a control area of the substrate.

5. The computer-implemented method of claim 4, wherein the test area comprises analyte-bound particles, and the control area comprises analyte-unbound particles.

6. The computer-implemented method of claim 4, wherein the test area comprises an analyte capture agent.

7. The computer-implemented method of claim 6, wherein the analyte capture agent is an antibody.

8. The computer-implemented method of claim 6, wherein the detector is a colloidal gold particle that is bound to the analyte capture agent.

9. The computer-implemented method of claim 1, further comprising quantifying the amount of the analyte in the subject at a first time point and at a second time point.

10. The computer-implemented method of claim 1, wherein the substrate is a lateral flow device.

11. The computer-implemented method of claim 1, wherein the progesterone metabolite is pregnanediol glucuronide.

12. The computer-implemented method of claim 1, wherein the hormone profile comprises an ovulation status.

13. The computer-implemented method of claim 1, wherein the hormone profile comprises a disease status.

14. The computer-implemented method of claim 1, wherein the substrate comprises gold nanoparticles.

15. The computer-implemented method of claim 1, wherein the instructions for analyzing pixel intensities of the image comprise a morphological transformation.

16. The computer-implemented method of claim 1, wherein the instructions for analyzing pixel intensities of the image comprise a colorspace conversion.

17. The computer-implemented method of claim 1, wherein the instructions for analyzing pixel intensities of the image comprise clustering.

18. The computer-implemented method of claim 1, wherein the substrate comprises an orientation element.

19. The computer-implemented method of claim 1, wherein the detection region is determined according to the orientation element.

20. The computer-implemented method of claim 1, wherein the detection region comprises a second detector that undergoes a change in a visible property of the detection region in response to contact with a second analyte in the biological sample.

21. The computer-implemented method of claim 1, wherein the report is personalized to the subject.

22. The computer-implemented method of claim 1, further comprising identifying an ovulation status of the subject based on one or more algorithms.

23. The computer-implemented method of claim 1, further comprising automatically generating a message containing the subject's ovulation status and transmitting the message in real time.

24. The computer-implemented method of claim 1, further comprising automatically syncing and storing the analyzed data specific to the subject in the training set of quantified concentrations of a plurality of analytes.

\* \* \* \* \*